US008486623B2

(12) United States Patent
Monforte et al.

(10) Patent No.: US 8,486,623 B2
(45) Date of Patent: *Jul. 16, 2013

(54) RELEASABLE NONVOLATILE MASS-LABEL MOLECULES

(75) Inventors: Joseph A. Monforte, Berkeley, CA (US); Christopher H. Becker, Palo Alto, CA (US); Daniel J. Pollart, Menlo Park, CA (US); Thomas A. Shaler, Menlo Park, CA (US)

(73) Assignee: Sequenom, Inc., San Diego, CA (US)

( * ) Notice: Subject to any disclaimer, the term of this patent is extended or adjusted under 35 U.S.C. 154(b) by 765 days.

This patent is subject to a terminal disclaimer.

(21) Appl. No.: 11/583,587

(22) Filed: Oct. 19, 2006

(65) Prior Publication Data

US 2012/0046180 A1 Feb. 23, 2012

Related U.S. Application Data

(63) Continuation of application No. 10/202,189, filed on Jul. 22, 2002, now Pat. No. 7,132,519, which is a continuation of application No. 08/988,024, filed on Dec. 10, 1997, now Pat. No. 6,635,452.

(60) Provisional application No. 60/033,037, filed on Dec. 10, 1996, provisional application No. 60/046,719, filed on May 16, 1997.

(51) Int. Cl.
*C12Q 1/68* (2006.01)
*C07H 21/02* (2006.01)
*C07H 21/04* (2006.01)
*C07K 1/00* (2006.01)

(52) U.S. Cl.
USPC .......... 435/6.1; 536/23.1; 536/25.3; 530/300; 530/350

(58) Field of Classification Search
USPC .................. 435/6.1; 536/23.1, 25.3; 530/300, 530/350
See application file for complete search history.

(56) References Cited

U.S. PATENT DOCUMENTS

| | | | |
|---|---|---|---|
| 3,553,452 A | 1/1971 | Tiernan et al. |
| 3,776,700 A | 12/1973 | Gallant |
| 3,807,235 A | 4/1974 | Lefkovits |
| 3,931,516 A | 1/1976 | Fletcher et al. |
| 4,047,030 A | 9/1977 | Lobach |
| 4,139,346 A | 2/1979 | Rabbani |
| 4,178,359 A | 12/1979 | Mondabaugh et al. |
| 4,230,797 A | 10/1980 | Boguslaski et al. |
| 4,231,999 A | 11/1980 | Carisson et al. |
| 4,461,328 A | 7/1984 | Kenney |

(Continued)

FOREIGN PATENT DOCUMENTS

| | | |
|---|---|---|
| DE | 4431174 | 3/1996 |
| DE | 19617011 | 4/1996 |

(Continued)

OTHER PUBLICATIONS

Abrams et al., "Comprehensive Detection of Single Base Changes in Human Genomic DNA Using Denaturing Gradient Gel Electrophoresis and a GC Clamp", Genomics,7:463-475 (1990).

(Continued)

*Primary Examiner* — Jezia Riley
(74) *Attorney, Agent, or Firm* — Grant Anderson LLP

(57) ABSTRACT

Releasable tag reagents for use in the detection and analysis of target molecules, particular in mass spectrometric analyzes are provided. Also provided are methods of detection that employ releasable tag reagents.

27 Claims, 35 Drawing Sheets

U.S. PATENT DOCUMENTS

| | | |
|---|---|---|
| 4,515,781 A | 5/1985 | Torrence et al. |
| 4,554,839 A | 11/1985 | Hewett et al. |
| 4,582,789 A | 4/1986 | Sheldon, III et al. |
| 4,604,363 A | 8/1986 | Newhouse et al. |
| 4,625,112 A | 11/1986 | Yoshida |
| 4,629,689 A | 12/1986 | Diamond et al. |
| 4,650,750 A | 3/1987 | Giese |
| 4,663,944 A | 5/1987 | Bernius et al. |
| 4,683,195 A | 7/1987 | Mullis et al. |
| 4,683,202 A | 7/1987 | Mullis |
| 4,709,016 A | 11/1987 | Giese |
| 4,711,955 A | 12/1987 | Ward et al. |
| 4,733,073 A | 3/1988 | Becker et al. |
| 4,775,619 A | 10/1988 | Urdea |
| 4,779,467 A | 10/1988 | Rainin et al. |
| 4,800,159 A | 1/1989 | Mullis et al. |
| 4,806,546 A | 2/1989 | Carrico et al. |
| 4,818,681 A | 4/1989 | Dattagupta |
| 4,877,745 A | 10/1989 | Hayes et al. |
| 4,882,127 A | 11/1989 | Rosenthal et al. |
| 4,883,750 A | 11/1989 | Whiteley et al. |
| 4,920,264 A | 4/1990 | Becker |
| 4,925,629 A | 5/1990 | Schramm |
| 4,935,357 A | 6/1990 | Szybalski |
| 4,952,518 A | 8/1990 | Johnson et al. |
| 5,000,921 A | 3/1991 | Hanaway et al. |
| 5,003,059 A | 3/1991 | Brennan |
| 5,059,654 A | 10/1991 | Hou et al. |
| 5,064,754 A | 11/1991 | Mills |
| 5,075,217 A | 12/1991 | Weber |
| 5,106,575 A | 4/1992 | Nakamura et al. |
| 5,108,703 A | 4/1992 | Pfost et al. |
| 5,118,605 A | 6/1992 | Urdea |
| 5,118,937 A | 6/1992 | Hillenkamp et al. |
| 5,135,870 A | 8/1992 | Williams et al. |
| 5,143,451 A | 9/1992 | Millgard |
| 5,143,854 A | 9/1992 | Pirrung et al. |
| 5,149,625 A | 9/1992 | Church et al. |
| 5,164,594 A | 11/1992 | Thompson et al. |
| 5,174,962 A | 12/1992 | Brennan |
| 5,175,209 A | 12/1992 | Beattie et al. |
| 5,198,540 A | 3/1993 | Koster |
| 5,210,412 A | 5/1993 | Levis et al. |
| 5,221,518 A | 6/1993 | Mills |
| 5,237,016 A | 8/1993 | Ghosh et al. |
| 5,242,974 A | 9/1993 | Holmes |
| 5,262,128 A | 11/1993 | Leighton et al. |
| 5,288,644 A | 2/1994 | Beavis et al. |
| 5,300,774 A | 4/1994 | Buttrill, Jr. |
| 5,325,021 A | 6/1994 | Duckworth et al. |
| 5,338,688 A | 8/1994 | Deeg et al. |
| 5,350,676 A | 9/1994 | Oberhardt et al. |
| 5,360,819 A | 11/1994 | Giese |
| 5,364,759 A | 11/1994 | Caskey et al. |
| 5,364,760 A | 11/1994 | Chu et al. |
| 5,365,063 A | 11/1994 | Kaesdorf et al. |
| 5,369,004 A | 11/1994 | Polymeropoulos et al. |
| 5,376,355 A | 12/1994 | Turteltaub et al. |
| 5,378,602 A | 1/1995 | Polymeropoulos et al. |
| 5,399,857 A | 3/1995 | Doroshenko et al. |
| 5,403,711 A | 4/1995 | Walder et al. |
| 5,405,746 A | 4/1995 | Uhlen |
| 5,412,083 A | 5/1995 | Giese et al. |
| 5,427,929 A | 6/1995 | Richards et al. |
| 5,430,136 A | 7/1995 | Urdea et al. |
| 5,436,143 A | 7/1995 | Hyman |
| 5,439,649 A | 8/1995 | Tseung et al. |
| 5,459,039 A | 10/1995 | Modrich et al. |
| 5,464,985 A | 11/1995 | Cornish et al. |
| 5,468,610 A | 11/1995 | Polymeropoulos et al. |
| 5,496,562 A | 3/1996 | Burgoyne |
| 5,498,545 A | 3/1996 | Vestal |
| 5,503,980 A | 4/1996 | Cantor |
| 5,508,169 A | 4/1996 | Deugau et al. |
| 5,510,270 A | 4/1996 | Fodor et al. |
| 5,512,295 A | 4/1996 | Kornberg et al. |
| 5,512,439 A | 4/1996 | Hornes et al. |
| 5,514,548 A | 5/1996 | Krebber et al. |
| 5,516,931 A | 5/1996 | Giese et al. |
| 5,532,227 A | 7/1996 | Golub et al. |
| 5,538,897 A | 7/1996 | Yates, III et al. |
| 5,547,835 A | 8/1996 | Koster |
| 5,563,410 A | 10/1996 | Mullock |
| 5,580,434 A | 12/1996 | Robotti et al. |
| 5,580,733 A | 12/1996 | Levis et al. |
| 5,582,979 A | 12/1996 | Weber |
| 5,589,136 A | 12/1996 | Northrup et al. |
| 5,599,500 A | 2/1997 | Jones |
| 5,599,666 A | 2/1997 | Schumm et al. |
| 5,601,982 A | 2/1997 | Sargent et al. |
| 5,605,662 A | 2/1997 | Heller et al. |
| 5,605,798 A | 2/1997 | Koster |
| 5,607,912 A | 3/1997 | Samejima et al. |
| 5,609,907 A | 3/1997 | Natan |
| 5,622,824 A | 4/1997 | K oster |
| 5,625,184 A | 4/1997 | Vestal et al. |
| 5,627,369 A | 5/1997 | Vestal et al. |
| 5,633,496 A | 5/1997 | Sakairi et al. |
| 5,643,800 A | 7/1997 | Tarantino et al. |
| 5,650,489 A | 7/1997 | Lam et al. |
| 5,654,150 A | 8/1997 | King et al. |
| 5,661,028 A | 8/1997 | Foote |
| 5,663,242 A | 9/1997 | Ghosh et al. |
| 5,665,967 A | 9/1997 | Coxon et al. |
| 5,670,322 A | 9/1997 | Eggers et al. |
| 5,670,381 A | 9/1997 | Jou et al. |
| 5,674,686 A | 10/1997 | Schumm et al. |
| 5,677,195 A | 10/1997 | Winkler et al. |
| 5,688,642 A | 11/1997 | Chrisey et al. |
| 5,691,141 A | 11/1997 | Koster |
| 5,700,642 A | 12/1997 | Monforte et al. |
| 5,710,028 A | 1/1998 | Eyal et al. |
| 5,716,825 A | 2/1998 | Hancock et al. |
| 5,743,960 A | 4/1998 | Tisone |
| 5,756,050 A | 5/1998 | Ershow et al. |
| 5,762,876 A | 6/1998 | Lincoln et al. |
| 5,766,847 A | 6/1998 | Jackle et al. |
| 5,770,272 A | 6/1998 | Biemann et al. |
| 5,770,367 A | 6/1998 | Southern et al. |
| 5,770,860 A | 6/1998 | Franzen |
| 5,777,324 A | 7/1998 | Hillenkamp |
| 5,789,395 A | 8/1998 | Amin et al. |
| 5,807,522 A | 9/1998 | Brown et al. |
| 5,828,063 A | 10/1998 | Koster et al. |
| 5,830,655 A | 11/1998 | Monforte et al. |
| 5,846,717 A | 12/1998 | Brow et al. |
| 5,851,765 A | 12/1998 | Koster |
| 5,853,989 A | 12/1998 | Jeffreys et al. |
| 5,854,486 A | 12/1998 | Dreyfus |
| 5,864,137 A | 1/1999 | Becker et al. |
| 5,869,240 A | 2/1999 | Patterson |
| 5,869,242 A | 2/1999 | Kamb |
| 5,872,003 A | 2/1999 | Koster |
| 5,872,010 A | 2/1999 | Karger et al. |
| 5,885,775 A | 3/1999 | Haff et al. |
| 5,888,819 A | 3/1999 | Goelet et al. |
| 5,900,481 A | 5/1999 | Lough et al. |
| 5,925,520 A | 7/1999 | Tully et al. |
| 5,927,547 A | 7/1999 | Papen et al. |
| 5,928,906 A | 7/1999 | Koster et al. |
| 5,965,363 A | 10/1999 | Monforte et al. |
| 5,969,350 A | 10/1999 | Kerley et al. |
| 5,976,798 A | 11/1999 | Parker et al. |
| 5,985,356 A | 11/1999 | Schultz et al. |
| 5,989,871 A | 11/1999 | Grossman et al. |
| 5,994,065 A | 11/1999 | Van Ness |
| 6,001,567 A | 12/1999 | Brow et al. |
| 6,004,744 A | 12/1999 | Goelet et al. |
| 6,006,171 A | 12/1999 | Vines et al. |
| 6,022,688 A | 2/2000 | Jurinke et al. |
| 6,024,925 A | 2/2000 | Little et al. |
| 6,027,890 A | 2/2000 | Ness et al. |
| 6,040,193 A | 3/2000 | Winkler et al. |
| 6,043,031 A | 3/2000 | Koster et al. |
| 6,051,378 A | 4/2000 | Monforte et al. |
| 6,074,823 A | 6/2000 | Koster et al. |
| 6,090,558 A | 7/2000 | Butler et al. |

| | | | |
|---|---|---|---|
| 6,104,028 A | 8/2000 | Hunter et al. | |
| 6,110,426 A | 8/2000 | Shalon et al. | |
| 6,111,251 A | 8/2000 | Hillenkamp | |
| 6,121,048 A | 9/2000 | Zaffaroni et al. | |
| 6,133,436 A | 10/2000 | Koster et al. | |
| 6,136,269 A | 10/2000 | Winkler et al. | |
| 6,140,045 A | 10/2000 | Wohlstadter et al. | |
| 6,140,053 A | 10/2000 | Koster | |
| 6,146,854 A | 11/2000 | Koster et al. | |
| 6,194,144 B1 | 2/2001 | Koster | |
| 6,197,498 B1 | 3/2001 | Koster | |
| 6,207,370 B1 | 3/2001 | Little et al. | |
| 6,221,601 B1 | 4/2001 | Koster et al. | |
| 6,221,605 B1 | 4/2001 | Koster | |
| 6,225,061 B1 | 5/2001 | Becker et al. | |
| 6,225,450 B1 | 5/2001 | Koster | |
| 6,235,478 B1 | 5/2001 | Koster | |
| 6,238,871 B1 | 5/2001 | Koster | |
| 6,258,538 B1 | 7/2001 | Koster et al. | |
| 6,265,716 B1 | 7/2001 | Hunter et al. | |
| 6,268,131 B1 | 7/2001 | Kang et al. | |
| 6,268,144 B1 | 7/2001 | Koster | |
| 6,277,573 B1 | 8/2001 | Koster | |
| 6,300,076 B1 | 10/2001 | Koster | |
| 6,303,309 B1 | 10/2001 | Jurinke et al. | |
| 6,312,893 B1 | 11/2001 | Van Ness et al. | |
| 6,322,970 B1 | 11/2001 | Little et al. | |
| 6,576,426 B2 | 6/2003 | Southern et al. | |
| 6,613,508 B1 | 9/2003 | Ness et al. | |
| 6,623,928 B2 | 9/2003 | Van Ness et al. | |
| 2001/0055811 A1 | 12/2001 | Hillenkamp | |
| 2002/0005478 A1 | 1/2002 | Hillenkamp | |
| 2002/0009394 A1 | 1/2002 | Köster et al. | |
| 2002/0040130 A1 | 4/2002 | Braun | |
| 2002/0109085 A1 | 8/2002 | Hillenkamp et al. | |
| 2002/0119456 A1 | 8/2002 | Ness et al. | |

FOREIGN PATENT DOCUMENTS

| | | |
|---|---|---|
| DE | 4438630 | 5/1996 |
| DE | 19618032 | 5/1996 |
| DE | 19628178 | 7/1996 |
| DE | 19731479 | 1/1997 |
| DE | 19754978 | 12/1997 |
| EP | 175467 | 3/1986 |
| EP | 227772 | 6/1986 |
| EP | 329822 | 8/1988 |
| EP | 320308 | 12/1988 |
| EP | 360676 | 3/1990 |
| EP | 543550 | 11/1992 |
| EP | 593789 | 4/1994 |
| EP | 771019 | 10/1996 |
| GB | 2017105 | 3/1979 |
| GB | 2233654 | 7/1990 |
| GB | 2260811 | 4/1993 |
| GB | 2312782 | 11/1997 |
| GB | 2332273 | 6/1999 |
| JP | 63230086 | 9/1988 |
| JP | 2215399 | 8/1990 |
| JP | 4178359 | 6/1992 |
| WO | WO 85/02907 | 4/1985 |
| WO | WO 86/07612 | 12/1986 |
| WO | WO 97/06270 | 10/1987 |
| WO | WO 88/10315 | 12/1988 |
| WO | WO 89/03432 | 4/1989 |
| WO | WO 89/06700 | 7/1989 |
| WO | WO 89/12624 | 12/1989 |
| WO | WO 89/12694 | 12/1989 |
| WO | WO 90/01564 | 2/1990 |
| WO | WO 90/04649 | 3/1990 |
| WO | WO 90/08398 | 7/1990 |
| WO | WO 91/11533 | 8/1991 |
| WO | WO 91/15600 | 10/1991 |
| WO | WO 92/05287 | 2/1992 |
| WO | WO 92/13629 | 8/1992 |
| WO | WO 93/08305 | 10/1992 |
| WO | WO 93/09668 | 5/1993 |
| WO | WO 93/13220 | 7/1993 |
| WO | WO 93/23563 | 11/1993 |
| WO | WO 93/24834 | 12/1993 |
| WO | WO 94/16090 | 1/1994 |
| WO | WO 94/11530 | 5/1994 |
| WO | WO 94/16101 | 7/1994 |
| WO | WO 94/20978 | 9/1994 |
| WO | WO 94/21822 | 9/1994 |
| WO | WO 94/28418 | 12/1994 |
| WO | WO 95/07361 | 3/1995 |
| WO | WO 95/13381 | 5/1995 |
| WO | WO 95/13538 | 5/1995 |
| WO | WO 95/15400 | 6/1995 |
| WO | WO 95/04160 | 9/1995 |
| WO | WO 95/25737 | 9/1995 |
| WO | WO 95/31429 | 11/1995 |
| WO | WO 0683234 | 11/1995 |
| WO | WO 96/10648 | 4/1996 |
| WO | WO 96/14406 | 5/1996 |
| WO | WO 96/15262 | 5/1996 |
| WO | WO 96/17080 | 6/1996 |
| WO | WO 96/29431 | 9/1996 |
| WO | WO 96/30545 | 10/1996 |
| WO | WO 96/32504 | 10/1996 |
| WO | WO 96/37630 | 11/1996 |
| WO | WO 97/08306 | 3/1997 |
| WO | WO 97/33000 | 3/1997 |
| WO | WO 97/19110 | 5/1997 |
| WO | WO 97/27327 | 7/1997 |
| WO | WO 97/27331 | 7/1997 |
| WO | WO 97/37041 | 10/1997 |
| WO | WO 97/40462 | 10/1997 |
| WO | WO 97/42348 | 11/1997 |
| WO | WO 97/43617 | 11/1997 |
| WO | WO 98/03257 | 1/1998 |
| WO | WO 98/11249 | 3/1998 |
| WO | WO 98/54751 | 3/1998 |
| WO | WO 98/20019 | 5/1998 |
| WO | WO 98/20020 | 5/1998 |
| WO | WO 98/20166 | 5/1998 |
| WO | WO 98/23284 | 6/1998 |
| WO | WO 98/26095 | 6/1998 |
| WO | WO 98/33052 | 7/1998 |
| WO | WO 98/33808 | 8/1998 |
| WO | WO 98/35609 | 8/1998 |
| WO | WO 98/24935 | 11/1998 |
| WO | WO 99/05319 | 2/1999 |
| WO | WO 99/05323 | 2/1999 |
| WO | WO 99/12040 | 3/1999 |
| WO | WO 99/31278 | 6/1999 |
| WO | WO 99/55718 | 11/1999 |
| WO | WO 99/57318 | 11/1999 |
| WO | WO 00/51053 | 8/2000 |
| WO | WO 00/56446 | 9/2000 |
| WO | WO 00/60361 | 10/2000 |

OTHER PUBLICATIONS

Abstract: Patent abstracts of Japan, 016/485 (c-0993), (1992).

Adler et al., "Cell Membrane Coating with Glutaraldehyde: Application to a Versatile Solid-Phase Assay for Thyroid Membrane Proteins and Molecules Interacting with Thyroid Membranes", Anal. Biochem., 148:320-327 (1985).

Agrawal (Ed.), "Protocols for Oligonucleotides and Analogs. Methods in Molecular Biology", Humana Press, Totowa, NJ, 20:143-164 (1993).

Agrawal et al., "Oligodeozynucleoside Methylphosphonates: Synthesis and Enzymic Degradation", Tetrahedron Lett., 28:3539-3542 (1987).

Alford et al., "Rapid and Efficient Resolution of Parentage by Amplification of Short Tandem Repeats", Am. J. Hum. Genet., 55:190-195 (1994).

Allcock et al., Contemporary Polymer Chemistry, Prentice-Hall, Inc., Englewood Cliffs, NJ, 1981.

Anker et al., "Tetranuleotide Repeat Polymorphism at the Human Thyroid Peroxidase (hTPO) Locus", Hum. Mol. Genet., 1:137 (1992).

Arlinghaus et al., "Multiplexed DNA Sequencing and Diagnostics by Hybridization with Enriched Stable Isotope Labels", Anal. Chem., 69:1510-1517 (1999).

Arnott et al., "Construction and Performance of a Laser Desorption/Ionization TOF Mass Spectrometer System: Applications to Problems in Peptide, Protein, and DNA Structural Analysis", Presented at: Proceedings of the 40th ASMS Conference on Mass Spectrometry and Allied Topics, Washington, D.C., pp. 328-329, May 31-Jun. 5, 1992.

Atherton et al., Solid Phase Peptide Synthesis, IRL, Oxford, 1989.

Ausubel et al., Current Protocols in Molecular Biology, John Wiley & Sons, New York, 1997.

Bahr et al., "Analysis of Biopolymers by Matrix-Assisted Laser Desorption/Ionization (MALDI) Mass Spectrometry", Fresenius J. Anal. Chem., 348:783-791 (1994).

Bai et al., "Matrix-Assisted Laser Desorption/Ionization Mass Spectrometry of Restriction Enzyme-Digested Plasmid DNA Using an Active Nation Substrate", Rapid Commun. in Mass Spectrometry, 8:687-691 (1994).

Bai et al., "Procedures for Detection of DNA by Matrix-Assisted Laser Desorption/Ionization Mass Spectrometry Using a Modified Nafion Film Substrate", Rapid Commun. in Mass Spectrometry, 9:1172-1176 (1995).

Bannwarth et al., "Laboratory Methods, A System for the Simultaneous Chemical Synthesis of Different DNA Fragments on Solid Support", DNA, 5:413-419 (1986).

Bannwarth, W., "Gene Technology a Challenge for the Chemist," Chimica, 41:302-317 (1987).

Bannwarth, W., "Solid-Phase Synthesis of Oligodeoxynucleotides Containing Phosphoramidate Internucleotide Linkages and Their Specific Chemical Cleavage", Helvetica Chimica Acta, 71:1517-1527 (1988).

Barinaga, M., "Protein Chemists Gain a New Analytical Tool", Science, 246:32-33 (1989).

Barlos et al., "Darstellung Geschutzyer Peptid-Fragmente Unter Einsatz Substituierter Triphenylmethyl-Harze", Tetrahedron Lett., 30:3943-3946 (1989).

Batista-Viera et al., "A New Method for Reversible Immobilization of Thiol Biomolecules Based on Solid-Phase Sound Thiolsulfonate Groups", App. Biochem. Biotech., 31:175-195 (1991).

Becker et al., "Genetic Analysis of Short Tandem Repeat Loci by Time of Flight Mass Spectrometry", Seventh International Symposium on Human Identification, pp. 158-162 (1996).

Belanger et al., "Molecular Mass and Carbohydrate Structure of Prostate Specific Antigen: Studies for Establishment of an International PSA Standard", Prostate, 27(4):187-197 (1995).

Benner et al., "DNA Base-Pair Substitutions Detected in Double-Stranded DNA with Matrix-Assisted Laser Desorption/Ionization Time-of-Flight Mass Spectrometry", Eur. Mass Spectrum, pp. 479-785 (1995).

Benner et al., "Identification of Denatured Double-Stranded DNA by Matrix-Assisted Laser Desorption/Ionization Time-of-Flight Mass Spectrometry", Rapid Commun. in Mass Spectrom., 9:537-540 (1995).

Bergh et al., "Complete Sequencing of the p53 Gene Provides Prognostic Information in Breast Cancer Patients, Particularly in Relation to Adjuvant Systemic Therapy and Radiotherapy"Nature Medicine, 1:1029-1034 (1995).

Bevan et al., "The Analysis of Oligonucleotides and Their Phosphoramidate Analogues by LSIMS Mass Spectrometry", Presented at: The 13th ASMS Conference on Mass Spectrometry and Allied Topics, pp. 983-984, May 19-24, 1991.

Bischoff et al., "Introduction of 5'-Terminal Functional Groups into Synthetic Oligonucleotides for Selective Immoblilization", Anal. Biochem., 164:336-344 (1987).

Braun et al., "Detecting CFTR Gene Mutations by Using Primer Oligo Base Extension and Mass Spectrometry", Clin. Chem., 43:1151-1158 (1997).

Braun et al., "Improved Analysis of Microsatellites Using Mass Spectrometry", Genomics, 46:18-23 (1997).

Bruce et al., "Bio-Affinity Characterization Mass Spectrometry", Rapid Comm. Mass Spec., 9:644-650 (1995).

Brummel et al., "A Mass Spectrometric Solution to the Address problem of Combinatorial Libraries", Science, 264:399-402 (1994).

Brummel et al., "Evaluation of Mass Spectrometric Methods Applicable to the Direct Analysis of Non-Peptide Bead-Bound Combinatorial Libraries", Anal. Chem., 68:327-242 (1996).

Buchet et al., "Gas Chormatography Determination of the Urinary Metabolites of Trichlorethylene: Trichloracetic Acid and Trichlorethanol," Arch. Mal. Prof. Med. Trav., 35:395-402 (1974).

Burbaum et al., "A Paradigm for Drug Discovery Employing Encoded Combinatorial libraries," Proc. Natl. Acad. Sci. USA, 92:6027-6031 (1995).

Busch et al., "Mass Spectrometry of Large, Fragile, and Involatile Molecules", Science, 218:247-254 (1982).

Butler et al., "High-throughput STR Analysis by Time-of-Flight Mass Spectrometry", Proceedings of the Second European Symposium on Human Identification 1998, Promega Coprporation, in press, (1998).

Butler et al., "Rapid and Automated Analysis of Short Tandem Repeat loci Using Time-of-Flight mass Spectrometry", Proceedings of the Eighth International Symposium on Human Indetification 1997, Promega Corporation, pp. 94-101 (1998).

Butler et al., "Reliable Genotyping of Short Tandem Repeat Loci without an Allelic Ladder Using Time-of-Flight Mass Spectrometry", Int. J. Leg. Med., in press, (1998).

Chait et al., "Weighing Naked Proteins: Practical, High-Accuracy Mass Measurement of Peptides and Proteins", Science, 257:1885-1894 (1992).

Chang et al., "Detection of ?F508 Mutation of the Cystic Fibrosis Gene by Matrix-Assisted Laser Desorption/Ionization Mass Spectrometry", Rapid Commun. in Mass Spectrometry, 9:772-774 (1995).

Chee, M., "Enzymatic Multiplex DNA Sequencing", Nucl. Acids Res., 19(12):3301-3305 (1991).

Church et al., "Multiplex DNA Sequencing," Science, 240:185-188 (1988).

Collins et al,. "Altered Transcription of the c-abl Oncogene in K-562 and Other Chronic Myelogenous Leukemia Cells", Science, 225:72-74 (1984).

Collins et al., "A DNA Polymorphism Discovery Resource for Research on Human Genetic Variation", Genome Res., 8:1229-1231 (1998).

Copley et al., "Exonuclease Cycling Assay: An Amplified Assay for the Detection of Specific DNA Sequences", Biotech., 13:888-892 (1992).

Corey, et al., "A Total Synthesis of (±)-Fumagillin", J. Am. Chem. Soc., 94:2549-2550 (1972).

Cormier et al., "Synthesis of Hexanucleotide Analogues Containing Disopropylsilyl Internucleotide Linkages", Nucl. Acids Res., 16:4583-4594 (1988).

Cosstick et al., "Solid Phase Synthesis of Oligonucleotides Containing 3'Thiothymidine", Tetrahedron Lett., 30(35):4693-4696 (1989).

Cosstick et al., "Synthesis and Phosphorus-Sulfur Bond Cleavage of 3'-Thiothymidyly(3'-5') Thymidine," J. Chem. Soc., Chem. Comm., pp. 992-993 (1988).

Cosstick et al., "Synthesis and Properties of Dithymidine Phosphate Analogues Containing 3'-Thiothimidine" Nucl. Acid Res., 18:829-835 (1990).

Crain et al., "Applications of Mass Spectrometry to the Characterization of Oligonucleotides and Nucleic Acids", Curr. Opin. Biotechnol., 9:25-34 (1998).

Crain P.F., "Nucleic Acids: Overview and Analytical Strategies", In: Mass spectrometry in Biomolecular Sciences, Caprioli et al., Eds., Kluwer Academic Publishers, Netherlands, pp. 351-379 (1996).

Dale et al., "The Synthesis and Enzymatic Polymerization of Nucleotides Containing Mercury: Potential Tools for Nucleic Acid Sequencing and Structural Analysis", Proc. Natl. Acad. Sci. USA, 70:2238-2242 (1973).

Daley et al., "Transformation of an Interleukin 3-Dependent Hematopoietic Cell Line by the Chronic Myelogenous Leukemia-Specific P210ber/abl Protein", Proc. Natl. Acad. Sci. USA, 85:9312-9316 (1988).

Derwent# 007678032, WPI Acc No. 88-311964/198844, citing Japanese Patent No. JP 63230086 A, "Carrier Immobilising Physiological Active Substance—Comprises Binding Chain-Form Disulphide cpd. Via Epoxy gp. with Latex Contg. Polymer Particles", 1988.

Derwent# 008221915, WPI Acc. No. 90-108916/199015, citing European Patent No. EP 0360676 A, "Size Analysis of Biological Mol. Fragments—by Mass Spectrometry, Esp. In Nulceic Acid Sequencing", 1990.

Derwent# 008246197, WPI Acc. No. 1990-133198/199018, citing PCT Patent No. WO 9004649 A, "Nucleic Acid Sequencing-Involving Amplification-Denaturation Cycles in Presence of Deoxy-Nucleoside Alpha-Thio-Triphosphate", 1990.

Derwent# 008415766, WPI Acc. No. 90-302767/199040, citing Japanese Patent No. JP 2215399 A, "Method for Detecting DNA—Includes Denaturing to Single Strand, Combining with DNA Primer Having Corresp. Base Sequence Forming Replicator etc.", 1990.

Derwent# 009135586, WPI Acc. No. 1992-263024/199232, citing Japanese Patent No. JP 4178359 A, "New Anti-Inflammatory Tetracylcine Derivs.—for Treating Articular Rheumatism, Osteoarthritis, Reiter's Syndrome, Lyme Disease, etc.", 1992.

Derwent# 010643408, WPI Acc. No. 1996-140362/199615, citing German Patent No. DE 4431174 A, "Detecting Tumour Specific mRNA by Conversion to cDNA and Amplification—Provides Early, Sensitive and Specific Diagnosis and Monitoring, Partic. by Analysis of Blood or Sputum," 1996.

Derwent# 010725941, WPI Acc. No. 1996-222896/199623, citing German Patent No. DE 4438630 A, "Amplification of Non-Characterized DNA Fragments-Using Only a Single Primer, with Formation of Hairpin Loops During a Second Strand Synthesis", 1996.

Derwent# 011458787, WPI Acc. No. 1997-436694/199741, citing German Patent No. DE 19628178 C, "Loading Matrix-Assisted Laser Desorption-Ionisation Sample Plate for Mass Spectrometric Analysis—Using Simple Multi-Pipette to Prepare Tens of Thousands of Samples Rapidly and Reliably for e.g. Biochemical and Genetic Investigations Optionally Using Electrophoretic Concentration and Delivery Technique", 1997.

Derwent#012012061, WPI Acc. No. 1998-428971/199837, citing German Patent No. DE19731479 A, "Device for Analysis of Target Chemcicals has Light Emitting Array—with Chemical Binder Elements Attached to Capture Target Chemicals which Change Emitted Light Pattern Accordingly", 1998.

Doktycz et al., "Analysis of Polymerase Chin Reaction-Amplified DNA Products by Mass Spectrometry Using Matrix-Assisted Laser Desorption and Ekectrospray: Current Status", Anal. Biochem., 243:55-65 (1995).

Dubovsky et al., "Sets of Short Tandem Repeat Polymorphisms for Efficient Linkage Screening of the Human Genome", Hum. Mol. Genet., 4:449-452 (1995).

Duchateau et al., "Selection of Buffers and of an Ion-Pairing Agent for Thermospray Liquid Chromatography-Mass Spectrometric Analysis of Ionic Compounds", J. Chrom., 552:605-612 (1991).

Eckstein, F., (Ed.), Oligonucleotides and Analogues: A Practical Approach Oxford:Oxford University Press, pp. 56-57, 137-139, 256-259 (1991).

Edmonds et al., "Electrospray Ionization Mass Spectrometry and Tandem Mass Spectrometry of Small Oligonucleotides", Presented at: 37th ASMS Conferences on Mass Spectrometry and Allied Topics, Miami Beach, Florida, pp. 844-845, May 21-26, 1989.

Edwards et al., "DNA Typing and Genetic Mapping with Trimeric and Tetrameric Tandem Repeats", Hum. Mol. Genet., 49:746-756 (1991).

Elov et al. "Synthesis of RNA Using T7 RNA Polymerase and Immobilized DNA in a Stream Type Reactor", Bioorganicheskaia Khimia, 17(6):789-794 (1991).

Fang et al., "Simultaneous Analysis of Mutant and Normal Alleles for Multiple Cystic Fibrosis Mutations by the Ligase Chain Reaction", Human Mutation, 6:144-151 (1995).

Feng et al., "The RNA Component of Human Telomerase", Science, 269(5228):1236-1241 (1995).

Fenn et al., "Electrospray Ionization for Mass Spectrometry Large Biomolecules", Science, 246:64-71 (1989).

Fitzgerald et al., "Basic Matrices for the Matrix-Assisted Laser Desorption/Ionization Mass Spectrometry of Proteins and Oligonucleotides", Anal. Chem., 65:3204-3211 (1993).

Fitzgerald et al., "The Analysis of Mock DNA Sequencing Reactions Using Matrix-Assisted Laser Desorption/Ionization Mass Spectrometry", Rapid Comm. Mass Spec., 7:895-897 (1993).

Fodor et al., "Light-Directed, Spatially Addressable Parallel Chemical Synthesis", Science, 251:767-773, (1991).

Foster, et al., "Naming Names in Human Genetic Variation Research", Genome Res., 8:755-757 (1998).

Fregeau et al., "DNA Typing with Fluorescently Tagged Short Tandem Repeats: A Sensitive and Accurate Approach to Human Identification", Bio Tech., 15:100-119 (1993).

Freier et al., "Deconvolution of Combinatorial Libraries for Drug Discovery: A Model System", J. Med. Chem., 38:344-352 (1995).

Freifelder, Physical Biochemistry Applications to Biochemistry and Molecular Biology, 2nd ed. Wm. Freeman & Co., New York, NY, 1982.

Frohman, M.A., "Cloning PCR Products", The Polymerase Chain Reaction, Mullis, K.B. (Eds.), Birkhauser Boston, pp. 14-37 (1994).

Gale et al., "An 8-kilobase abl RNA Transcript in Chronic Myelogenous Leukemia", Proc. Natl. Acad. Sci. USA, 81:5648 (1984).

George et al., "Macromolecule Sequencing and Synthesis", Schlesinger (Ed.), pp. 127-149 (1988).

Ghosh et al., "Convalent Attachment of Oligonucleotides to Solid Supports", Nucl. Acids Res., 15:5353-5372 (1987).

Gimon et al., "Are Proton Transfer Reactions of Excited States Involved in UV Laser Desorption Ionization", Organic Mass Spec., 27:827-830 (1992).

Gingeras et al., "Hybridization Properties of Immobilized Nucleic Acids", Nucl. Acids Res., 15:5373-5390 (1987).

Glazer et al., "Stable Dye-DNA Intercalation Complexes as Reagents for High-Sensitivity Fluorescence Detection", Nature, 359:859-861 (1992).

Goldkorn et al., "A Simple and Efficient Enzymatic Method for Covalent Attachment of DNA to Cellulose: Application for Hybridization-Restriction Analysis and for in Vivo Synthesis of DNA Probes", Nucl. Acids Res., 14(22):9171-9191 (1986).

Green, N. M., In: Advances in Protein Chemistry, Avidin (Ed.), Academic Press, New York, N.Y., U.S.A., pp. 29, 85-133 (1975).

Gromova, E. S., "DNA Duplexes with Phosphoamide Bonds: the Interaction with EcoRII and Ssoll Restriction Endonucleases," Bioorg. Khim, 13:269 (1987).

Gyllensten, U. B., "PCR and DNA Sequencing", Bio Tech., 7:700-708 (1989).

Haag et al., "Rapid Identification and Speciation of Haemophilus Bacteria by Matrix-Assisted Laser Desorption/Ionization Time-of-Flight Mass Spectrometry", J. Mass Spec., 33(8):750-756 (1998).

Hammond et al., "Evaluation of 13 Short Tandem Repeat Loci for Use in Personal Identification Applications",Am. J. Hum. Genet., 55:175-189 (1994).

Hata et al., "A New Method for the Synthesis of 5'-Aminonucleosides and Their Phosphoramidate Derivatives", Chem. Lett., 601-604 (1976).

Hauge et al., "A Study of the Origin of 'Shadow Bands' Seen When Typing Dinucleotide Repeat Polymorphisms by the PCR™", Hum. Mol. Genet., 2:411-415 (1993).

Hayes et al., "Dual Analyte Immunoassay for Proteins Using Releasable Metal Ions as Labels (Albumin, Immunoglobin G)", Dissertation Abstracts International, 53(9B):4624 (1992).

Hearne et al., "Tetranucleotide Repeat Polymorphism at the HPRT Locus", Nucl. Acids Res., 19:5450 (1991).

Hegner et al., "Immobilizing DNA on Gold Via Thiol Modification for Atomic Force Microscopy Imaging in Buffer Solutions", FEBS Lett., 336:452-456 (1993).

Hegner et al., "Ultralarge Atomically Flat Template-Stripped Au Surfaces for Scanning Probe Microscopy", Surface Science, 291:39-46 (1993).

Herpich et al., "HPLC of Nucleic Acid Components with Violatile Mobile Phases I. Fast Nucleotide Separations Using Annomnium Carbonate and Ammonium Bicarbonate Gradients", J. High Resolution Chromatography,15:41 (1992).

Hettich et al., "Determination of Oligonucleotide Sequences and Modifications by Laser Desorption Fourier Transform Mass Spectrometry", Abst. Pap. Am. Chem. Soc., 200:1-2, Abstract 105 (1990).

Hillenkamp et al., "Laser Desorption Mass Spectrometry Part 1: Basic Mechanisms and Techniques", In: Mass Spectrometry in the Biological Sciences: A tutorial, pp. 165-179 (1992).

Hillenkamp et al., "Matrix Assisted UV-Laser Desorption/Ionization: A New Approach to Mass Spectrometry of Large Biomolecules", Biological Mass Spectrometry, A. L. Burlingame and J. A. McCloskey (Eds.), Elsevier Science Publishers, B. V., Amsterdam, pp. 49-61 (1989).

Hillenkamp, R., "Laser Desorption Mass Spectrometry: Mechanisms, Techniques and Applications", Adv. Mass Spec., 11A:354-362 (1988).

Hobbs, J. B., "Nulceotides and Nucleic Acids", Oranophosphorous Chem., 21:201-321 (1990).

Holland et al., "Detection of Specific Polymerase Chain Reaction Product by Utilizing the 5' ? 3' Exonuclease Activity of Thermus Aquaticus DNA polymerase", Proc. Natl. Acad. Sci. USA, 88:7276-7280 (1991).

Holmes et al., "The Use of Light-Directed Combinatorial Peptide Synthesis in Epitope Mapping", Biopolymers (Peptide Science), 37:199-211 (1995).

Huang et al., "Chinese Population Data on Three Tetrameric Short Tandem Repeat Loci-HUMTH01, TPOX, and CSF1PO- Derived Using Multiplex PCR and Manual Typing", Forensic Sci. Int., 71:131-136 (1995).

Hunter et al., "Cryogenic Frozen Solution Matrices for Analysis of DNA by Time-of-Flight Mass Spectrometry", Anal. Chem., 69:3608-3612 (1997).

Huppert et al., "Laser Studies of Proton Transfer", Adv. Chem. Phys., 47:643-679 (1981).

Innis et al., PCR Protocols, Academic Press, Inc., San Diego, CA, 1990.

Jacobson et al., "Applications of Mass Spectrometry to DNA Sequencing", GATA, 8(8):223-229 (1991).

Jensen et al., "Characterization of Peptide-Oligonucleotide Heteroconjugates by Mass Spectrometry", Nucl. Acids Res., 24:3866-3872 (1996).

Ji et al., "Two-Dimensional Electrophoretic Analysis of Proteins Expressed by Normal and Cancerous Human Crypts: Application of Mass Spectrometry to Peptide-Mass Fingerprinting", Electrophoresis, 15:391-405 (1994).

Jonkman et al., "Low-Temperature Positive Secondary Ion Mass Spectrometry of Neat and Argon-Diluted Organic Solids", Anal. Chem., 50:2078-2082 (1978).

Jurinke et al., "Analysis of Ligase Chain Reaction Products Via Matrix-Assisted Laser Desorption/Ionization Time-of-Flight Mass Spectrometry", Analytical Biochemistry, 237:174-181 (1996).

Karas et al., "Matrix- Assisted Laser Desorption Ionization Mass Spectrometry", Mass Spectrom. Rev., 10:335-357 (1991).

Karas et al., "Matrix Laser Desorption of Very Large Organic Molecules", In: Mass Spectrometry of Large Non-volatile Molecules for Marine Organic Chemistry, Hilf, E.R. and Tuszynski, W., (Eds.), World Scientific Publishers, Singapore, (1990) pp. 103-113.

Kayser et al., "Evaluation of Y-Chromosomal STRs: A Multicenter Study", Int. J. Leg. Med., 110:125-133 (1997).

Khrapko et al., "A Method for DNA Sequencing by Hybridization with Oligonucleotide Matrix", J. DNA Sequencing and Mapping, 1:375-388 (1991).

Kimpton et al., "A Further Tetranucleotide Repeat Polymorphism in the vWF Gene", Hum. Mol. Genet., 1:287 (1992).

Kimpton et al., "Automated DNA Profiling Employing Multiplex Amplification of Short Tandem Repeat Loci", PCR™ Meth. Appl., 3:13-22 (1993).

Kimpton et al., "Validation of Highly Discriminating Multiplex Short Tandem Amplification Systems for Individual Identification", Electrophoresis, 17:1283-1293 (1996).

Kirpekar et al., "Matrix Assisted Laser Desorption/Ionization Mass Spectrometry of Enzymatically Synthesized RNA Up to 150 kDa", Nucleic Acids Research, 22(19):3866-3870 (1994).

Koole et al., "A Novel Synthetic Approach to Phosphate-Methylated DNA Oligomers Using 9-fluorenylmethoxycarbonyl (Fmoc) as Temporary Base Amino Protecting Group", Proc. K. Ned. Akad. Wet., B91:205-209 (1988).

Köster et al., "Oligonucleotide Synthesis and Multiplex DNA Sequencing Using Chemiluminescent Detection," Nucl. Acids Res., Symposium Series, 24:318-321 (1991).

Kremsky et al., "Immobilization of DN Via Oligonucleotides Containing an Aldehyde or Carboxylic Acid Group at the 5' Terminus", Nucl. Acids Res., 15:2891-2909 (1987).

Krishnamurthy et al., "Biomolecules and Mass Spectroscopy", J. Natural Toxins 6(2):121-162 (1997).

Krishnamurthy, et al., "Rapid Identification of Bacteria by Direct Matrix Assisted Laser Desorption/Ionization Mass Spectrometric Analysis of Whole Cells", Rapid Comm. Mass Spec., 10(15):1992-1996 (1996).

Kuimelis et al., "Cleavage Properties of an Oligonucleotide Containing a Bridged Internucleotide 5'-phosphorothioate RNA Linkage", Nucleic Acids Research, 23:4753-4760 (1995).

Kusakawa et al., "Rapid and Reliable Protocol for direct Sequencing of Material Amplified by the Polymerase Chain Reaction", Bio Tech., 9:66-72 (1990).

Kwoh et al., "Transcription-Based Amplification System and Detection of Amplified Human Immunodeficiency Virus Type 1 with a Bead-Based Sandwich Hybridization Format", Proc. Natl. Acad. Sci. USA., 86:1173-1177 (1989).

Lagerstrom et al., "Capture PCR: Efficient Amplification of DNA Fragments Adjacent to a Known Sequence in Human YAC DNA," PCR Methods and Applications, 1:111-119 (1991).

Langer et al., "Enzymatic Synthesis of Biotin-Labeled Polynucleotides: Novel Nucleic Acid Affinity Probes", Proc. Natl. Acad. Sci. USA, 78:6633-6637 (1981).

Lareu et al., "A Highly Variable STR at the D12S391 Locus", Int. J. Leg. Med., 109:134-138 (1996).

Lay, Jr. et al., "Detection and Characterization of DNA Adducts at the Femtomole Level by Desorption Ionization Mass Spectrometry" Environ. Health Perspect., 99:191-193 (1993).

Lee et al., "Allelic Discrimination by Nick-Translation PCR with Fluorogenic Probes", Nucl. Acids Res., 21:3761-3766 (1993).

Lee et al., "Comparison on Short Tandem Repeat (STR) Detection Using Silver, Fluorescence and Matrix Assisted Laser Desorption Ionization Time-of-Flight Mass Spectrophotometry (MALDITOF-MS)", Proceedings of the Sixth International Symposium of Human Identification, published by Promega Corp., 1995.

Lee et al., "DNA Sequencing with Dye-Labeled Terminators and T7 DNA Polymerase: Effect of Dyes and dNTPs on Incorporation of Dye Terminators and Probability Analysis of Termination Fragments", Nucleic Acids Research, 20(10):2471-2483 (1992).

Leonard et al, "High-Resolution Structure of Mutagenic Lesion in DNA", Proc. Nat. Acad. Sci. Biochem., 87:9573-9576 (1990).

Liang et al., "The Use of 2-Hydroperoxytetrahydrofuran as a Reagent to Sequence Cytosine and to Probe Non-Watson-Crick DNA Structures", Nucleic Acids Research, 23(4):713-719 (1995).

Limbach et al., "Characterization of Oligonucleotides and Nucleic Acids by Mass Spectrometry", Curr. Opin. Biotech., 6:96-102 (1995).

Little et al., "MALDI on a Chip: Analysis of Arrays of Low-Femtomole to Subfemtomole Quantities of Synthetic Oligonucleotides and DNA Diagnostic Products Dispensed by a Peizoelectric Pipet", Anal. Chem., 69:4540-4546 (1997).

Little et al., "Mass Spectrometry from Miniaturized Arrays for Full Comparative DNA Analysis", Nature Med., 3(12):1413-1416 (1997).

Liu et al., "Rapid Screening of Genetic Polymorphisms Using Buccal Cell DNA with Detection by Matrix-Assisted Laser Desorption/Ionization Mass Spectrometry", Rapid Commun. in Mass Spectrometry, 9:735-743 (1995).

Liu et al., "Use of Nitrocellulose Film Substrate in Matrix-Assisted Laser Desorption/Ionization Mass Spectrometry for DNAa Mapping and Screening", Anal. Chem., 67:3482-3490 (1995).

Loboda et al., "Extraction Pulse Generator for Time-of-Flight Mass Spectrometry", Rev. Sci. Instrum., 66:4740-4741 (1995).

Longo et al., "Use of Uracil DNA Glycosylase to Control Carry-Over Contamination in Polymerase Chain Reactions", Gene, 93:125-128 (1990).

Lubman et al., "Linear Mass Reflectron with a Laser Photoionization Source for Time-of-Flight Mass Spectrometry", Anal. Chem., 55:1437-1440 (1983).

Lygo et al., "The Validation of Short Tandem Repeat (STR) Loci for Use in Forensic Casework", Intl. J. Leg. Med., 107:77-89 (1994).

Mag et al., "Synthesis and Selective Cleavage of an Oligodeoxynucleotide Containing a Bridged Internucleotide 5'-Phosphorothioate Linkage", Nucleic Acids Research, 19(7):1437-1441 (1991).

Martin et al., "Measuring Diversity: Experimental Design of Combinatorial Libraries for Drug Discovery", J. Med. Chem., 38:1431-1436 (1995).

Maskos et al., "Oligonucleotide Hybridizations on Glass Supports: A Novel Linker for Oligonucleotide Synthesis and Hybridization Properties of Oligonucleotides Synthesis In Situ", Nuc. Acids Res., 20(7):1679-1684 (1992).

Matthews et al., "Analytical Strategies for the Use of DNA Probes", Anal. Biochem., 169:1-25 (1988).

McBride et al., "An Investigation of Several Deoxynucleoside Phosphoramidites Useful for Synthesizing Deoxyoligonucleotides", Tetrahedron Lett., 24:245-248 (1983).

McNeal et al., "A New Method for the Analysis of Fully Protected Oligonucleotides by 252Cf-Plasma Desorption Mass Spectrometry. 3. Positive Ions", J. Am. Chem. Soc., 104:981-984 (1982).

Miller et al., "Syntheses and Properties of Adenine and Thymine Nucleoside Alkyl Phosphotriesters, the Neutral Analogs of Dinucleoside Monophosphates", J. Am. Chem. Soc., 93:6657-6665 (1971).

Mizusawa et al., "Improvement of the Dideoxy Chain Termination Method of DNA Sequencing by Use of Deoxy-7-Deazaguanosine Triphosphate in Place of dGTP", Nucleic Acids Research., 14(3):1319-1324 (1986).

Moalem et al., "Cluster Formation in the Vapor Produced by Laser Pulsing of the Y1Ba2Cu3O7 Superconducting Solid", J. Vacuum Sci. Technol., 10:3292-3299 (1992).

Mock et al., "Sample Immobilisation Protocols of Matrix Assisted Laser Desorption Mass Spectrometry", Presented at: Proceedings of the 40th ASMS Conference on Mass Spectrometry and Allied Topics, Washington, D.C., pp. 1921-1922, May 31-Jun. 5, 1992.

Moody et al., "Regiospecific Inhibition of DNA Dupication by Antisense Phosphate-methylated Oligonucleotides", Nucl. Acids Res., 12:4769-4782 (1989).

Musser et al., "Sensitivity Enhancement for Static and Continuous Flow FAB/MS Analysis of Nucleotides by Quarternary Amine Surfactants", Presented at: The 39th ASMS Conference on Mass Spectrometry and Allied Topics, pp. 374-375, May 19-24, 1991.

Nadji et al., "Photochemically and Photoenzymatically Cleavable DNA", J. Am. Chem. Soc., 114:9266-9269 (1992).

Naito et al., "Detection of Tyrosine Hydroxylase mRNA and Minimal Neuroblastoma Cells by the Reverse Transcription-Polymerase Chain Reaction", Eur. J. Cancer, 27:762-765 (1991).

Nakamaye et al., "Direct Sequencing of Polymerase Chain Reaction Amplified DNA Fragments Through the Incorporation of Deozynucleoside athiotriphosphates", Nucl. Acids Res., 16(21):9947-9959 (1988).

Nelson et al., "Detection of Human IgM at m/z⁻1 Mda", Rapid Commun. in Mass Spectrom., 9:7 (1995).

Nelson et al., "Volatization of High Molecular Weight DNA by Pulsed Laser Ablation of Frozen Aqueous Solutions", Science, 246:1585-1587 (1989).

Newman et al., "Incorporation of a Complete Set of Deoxyadenosine and Thymidine Analogues Suitable for the Study of Protein Nucleic Acid Interactions into Oligodeoxynucleotides", Biochemistry, 29:9891-9901 (1990).

Nordhoff et al., "Matrix-Assisted Laser Desorption/Ionization Mass Spectrometry of Nucleic Acids with Wavelengths in the Ulraviolet and Infrared", Rapid Commun. in Mass Spectrom., 6:771-776 (1992).

O'Donnell-Maloney et al., "The Development of Microfabricated Arrays for DNA Sequencing and Analysis", TIBTECH, 14:401-407 (1996).

Ogilvie et al., "Synthesis of a Thymidine Dinucleotide Analogue Containing an Internucleotide Silyl Linkage", Tetrahedron Lett., 26:4159-4162 (1986).

Ohlmeyer et al., "Complex Synthetic Chemical Libraries Indexed with Molecualr Tags", Proc. Natl. Acad. Sci. USA, 90:10922-10926 1993.

Okano et al., DNA Probe Assay Based on Exonuclease III Digestion of Probes Hybridized on Target DNA, Anal. Biochem., 228:101-108 (1995).

Olsen et al., "Direct Sequencing of Polymerase Chain Reaction Products", Methods in Enzymol., 218:79-92 (1993).

Olsen et al., "The Ribosomal Database Project", Nucl. Acids Res., 20:2199-2200 (1992).

Olsson, Isolation and Characterization of a Tumor Necrosis Factor Binding Protein from Urine, (XP000937599), Eur. J. Haematol., 42:270-275 (1989).

Ordoukhanian et al., "Design and Synthesis of a Versatile Photocleavable DNA Building Block. Application to Phototriggered Hybridization", J. Am. Chem. Soc., 117:9570-9571 (1995).

Orita et al., "Detection of Polymorphisms of Human DNA by Gel Electrophoresis as Single-Strand Conformation Polymorphisms", Proc. Natl, Acad. Sci. USA, 86:2766-2770 (1989).

Overberg et al., "Laser Desorption Mass Spectrometry, Part II Performance and Applications of Matrix-Assisted Laser Desorption/Ionization of Large Biomolecules", In: Mass Spectrometry in the Biological Sciences: A Tutorial, Gross, Ed., Kluwer Academic Publishers, Netherlands, pp. 181-197, 1992.

Palejwala et al., "Quantitative Multiplex Sequence Analysis of Mutational Hot Spots. Frequency and Specificity of Mutations Induced by a Site-Specific Ethenocytosine in M13 Viral DNA", Biochem., 32:4105-4111 (1993).

Parr et al., "Matrix-Assisted Laser Desorption/Ionization Mass Spectrometry of Synthetic Oligodeoxyribonucleotides", Rapid Commun. in Mass Spectrom., 6:369-372 (1992).

Pasini et al., "RET Mutations in Human Disease", Trends in Genetics, 12(4):138-144 (1996).

Pease et al., "Light-Generated Oligonucleotide Arrays for Raid DNA Sequence Analysis", Proc. Natl. Acad. Sci., USA, 91:5022-5026 (1994).

Pei et al., "A combinatorial Approach Toward DNA Recognition", Science, 253:1408-1411 (1991).

Pieles et al., "Matrix-assisted laser desorption ionization time-of-flight mass spectrometry: a powerful tool for the mass and sequence analysis of natural and modified oligonucleotides", Nucleic Acids Res., 21(14):3191-3196 (1993).

Podhajska et al., "Conversion of the FoklEndonuclease to a Universal Restriction Enzyme: Cleavage of Phage M13mp7 DNA at Predetermined Sites", Gene, 40:175-182 (1985).

Polymeropoulos et al., "Dinucleotide Repeat Polymorphism at the Human CTLA4 Gene", Nucl. Acids. Res., 19:4018 (1991).

Polymeropoulos et al., "Dinucleotide Repeat Polymorphism at the Human Non-Histone Chromosomal Protein HMG14 Gene", Nucl. Acids. Res., 19:3753 (1991).

Polymeropoulos et al., "Tetranucleotide Repeat Polymorphism at the Human c-fes/fps Proto-Oncogene (FES)", Nucl. Acids. Res., 19:4018 (1991).

Polymeropoulos et al., "Tetranucleotide Repeat Polymorphism at the Human Coagulation factor XlIIsubuint Gene (F13A1)", Nucl. Acids Res., 19:4306 (1991).

Polymeropoulos et al., "Tetranucleotide Repeat Polymorphism at the Human Met-tRNA-i Gene 1 (TRMI)", Nucl. Acids Res., 19:4306 (1991).

Polymeropoulos et al., "Tetranucleotide Repeat Polymorphism at the Human Tyrosine Hydroxylase Gene (TH)", Nucl. Acids Res., 19:3753 (1991).

Puers et al., "Allele Ladder Characterization of the Short Tandem Repeat Polymorphism Located in the 5' Flanking Region to the Human Coagulation Factor XIII A Subunit Gene", Genomics, 23:260-264 (1994).

Puers et al., "Identification of Repeat Sequence Heterogeneity at the Polymorphic Short Tandem Repeat Locus HUMTH01[AATG]n and Reassignment of Alleles in Population Analysis by Using a Locus-Specific Allele Ladder", Am. J. Hum. Genet., 53:953-958 (1993).

Richterich et al., "Cytosine Specific DNA Sequencing with Hydrogen Peroxide", Nucleic Acids Research, 23(23):4922-4923 (1995).

Roewer et al., "Simple Repeat Sequence on the Human Y Chromosome Are Equally Polymorphic as Their Autosomal Counterparts", Hum. Genet., 89:389-394 (1992).

Ross et al., "Analysis of DNA Fragments from Conventional and Microfabricated PCR Devices Using Delayed Extraction MALDI-TOF Mass Spectrometry", Anal. Chem., 70:2067-2073 (1998).

Ross et al., "Analysis of Short Tandem Repeat Polymorphisms in Human DNA by Matrix-Assisted Laser Desorption/Ionization Mass Spectrometry", Anal. Chem., 69:3966-3972 (1997).

Ruckman et al., "Laser-Induced Ion Mass Analysis: A Novel Technique for Solid-State Examination", Vacuum, 34:911-924 (1984).

Saenger, Principles of Nucleic Acid Structure, Spring-Verlag, NY, 1983.

Saha et al., "Diisopropylsilyl-Linked Oligonucleotide Analogs: Solid-Phase Synthesis and Physicochemical Properties", J. Org. Chem., 58:7827-7831 (1993).

Saiki et al., "Genetic Analysis of Amplified DNA with Immobilized Sequence-Specific Oligonucleotide Probes", Proc. Natl. Acad. Sci., 86:6230-6234 (1989).

Saleeba et al., "Chemical Cleavage of Mismatch to Detect Mutations", Methods Enzymology, 217:286-295 (1993).

Salerno et al., "Covalent Modification with Concomitant Inactivation of the cAMP-Dependant Protein Kinase by Affinity Labels Containing only 1-amino Acids", J. Biol. Chem., 268:13043-13049 (1993).

Sambrook et al., Molecular Cloning: A Laboratory Manual, 2d Ed., Cold Spring Harbor Laboratory Press, Cold Spring Harbor, NY. 1989.

Sandaltzopoulos et al., "Solid-Phase DNase I Footprinting", Biochemica, 4:25-27 (1995).

Sanger et al., "A Rapid Method for Determining Sequences in DNA by Primed Synthesis with DNA Polymerase", J. Molecular Biol., 94:441-448 (1975).

Sarkar et al., "Human Genetic Bi-allelic Sequences (HGBASE), a Database of Intra-genic Polymorphisms", 93(5):693-694 (1998).

Schena et al., "Quantitative Monitoring of Gene Expression Patterns with a Complementary DNA Mircoarray", Science, 270:467-470 (1995).

Schmidt et al., "Phylogenetic Identification of Uncultured Pathogens Using Ribosomal RNA Sequeneces", Methods in Enzymol., 235:205-222 (1994).

Seckinger et al., "Purification and Biologic Characterization of a Specific Tumor Necrosis Factor Alpha Inhibitor", (XP000673302 ISSN: 0021-9258) J. Biochem., 264(20):11966-11973 (1989).

Sedlak, "Gene Trace Systems Bests its Future in Genomics on TOF Mass Spectroscopy", Genetic Engineering News, 16(21), (1996) (website: http://www.genetrace.com).

Seliger et al., "Oligonucleotide Analogues with Dialkyl Silyl Internucleoside Linkages", Nucleosides Nucleotides, 6:483-484 (1987).

Senft, V., "Simple Determination of Trichloroacetic Acid in Urine Using Head Space Gas Chromatography: A Suitable Method for Monitoring Exposure to Trichloroethylene", J. Chromatography, 337:126-130 (1985).

Shaler et al., "Effect of Impurities on the Matrix-Assisted Laser Desorption Mass Spectra of Single-Stranded Oligodeoxynucleotides", Anal. Chem., 68(3):576-579 (1996).

Shaw et al., "Oligonucleoside Boranophosphate (Borane Phosphonate)", In: Methods in Molecular Biology, vol. 20: Protocols for Oligonucleotides and Analogs, S. Agrawal (Ed.), Humana Press, Inc., Totowa, NJ, chapter 11, 224-243 (1993).

Siegert et al., "Matrix-assisted Laser Desorption/Ionization Time-of-Flight Mass Spectrometry for the Detection of Polymerase Chain Reaction Products Containing 7-Deazapurinr Moieties", Anal. Biochem., 230:205-214 (1995).

Silveira et al., "PCR with Detachable Primers", Nucl. Acids Res., 23(6):1083-1084 (1995).

Siuzdak, G., "The Emergency of Mass Spectrometry in Biochemical Research", Proc. Natl. Acad. Sci. USA, 91:11290-11297 (1994).

Sloop et al.,"Synthesis of 3-(triethylstanny)-propanoic Acid: An Organotin Mass Label for DNA", Bioconjugate Chemistry, 4:406-409 (1993).

Smith, A.J., "DNA Sequence Analysis by Primed Synthesis," Methods in Enzymology 65:560-580 (1980).

Soukup et al., "Preparation of Oligonucleotide—Biotin Conjugates with Cleavable Linkers", Bioconjugate Chem., 6:135-138 (1995).

Southern et al., "Analyzing and Comparing Nucleic Acid Sequences by Hybridization to Arrays of Oligonucleotides: Evaluation Using Experimental Models," Genomics, 13:1008-1017 (1992).

Spengler et al., "Laser Mass Analysis in Biology", Ber. Bunsenqes Phys. Chem., 93(3):396-402 (1989).

Spengler et al., "Molecular Weight Determination of Underivatized Oligodeoxyribonucleotides by Positive-Ion Matrix-Assisted Ultraviolet Laser-Desorption Mass Spectrometry", Rapid Commun. Mass Spectrom., 4:99-102 (1990).

Sproat et al., "The Synthesis of Protected 5'-amino-2',5'-dideoxyribounucleoside-3'-( )-phosphoramidites; Applications of 5'-amino-oligodeoxyribonucleotides", Nucl. Acids Res., 15:6181-6196 (1987).

Sproat et al., "The Synthesis of Protected 5'-mercapto-2',5'-dideoxyribounucleoside-3'-()-phosphoramidites; uses of 5'-mercapto-oligodeoxyribonucleotides", Nucl. Acids Res., 15:4837 (1987).

Stahl et al., "Solid Phase DNA Sequencing Using the Biotin-Avidin System", Nucleic Acids Research, 16(7):3025-3038 (1988).

Stemmler et al., "Matrix-Assisted Laser Desorption/Ionization Fourier-Transform Mass Spectrometry of Oligodeoxyribonucleotides", Rapid Comm. Mass Spec., 7:828-836 (1993).

Stults et al., "Characterization of Oligodeoxynucleotide Conjugates by Electrospray Ionization Mass Spectrometry", Presented at: Proceedings of the 39th ASMS Conference on Mass Spectrometry and Allied Topics, Nashville, Tennessee, pp. 1161-1162, May 19-24, 1991.

Stults et al., "Improved Electrospray Ionization of Synthetic Oligodeoxynucleotides", Rapid Commun. Mass Spectrom., 5:359-363 (1991).

Syvanen et al., "Detection of Point Mutations by Solid-Phase Methods", Human Mutation, 3(3):172-179 (1994).

Szczylik et al., "Selective Inhibition of Leukemia Cell Proliferation by BCR-ABL antisense Oligodeoxynucleotides", Science, 253:562-565 (1991).

Szylbalski, "Universal Restriction Endonucleases: Designing Novel Cleavage Specificities by Combining Adapter Oligodeoxynucleotide and Enzyme Moieties", Gene, 40:169-173 (1985).

Tanaka et al., "Protein and Polymer Analyses up to m/z 100 000 by Laser Ionization Time-of-Flight Mass Spectrometry", Rapid Commun. in Mass Spectrometry, 2:151-153 (1988).

Tang et al., "Detection of 500-Nucleotide DNA by Laser Desorption Mass Spectrometry", Rapid Commun. in Mass Spectrometry, 8(9):727-730 (1994).

Tang et al., "Laser Mass Spectrometry of Oligonucleotides with Isomer Matrices", Rapid Comm. Mass Spec., 7:435-439 (1993).

Tang et al., "Laser Mass Spectrometry of Polydeoxyribothymidylic Acid Mixtures", Rapid Commun. Mass Spectrom., 7:63-66 (1993).

Tang et al., "Mass Spectrometry of Laser-Desorbed Oligonucleotides", Rapid Comm. Mass Spec., 6:365-368 (1992).

Tang et al., "Matrix-Assisted Laser desorption/Ionization of Restriction Enzyme-Digested DNA", Rapid Commun. in Mass Spectrometry, 8:183-186 (1994).

Taranenko et al., "Matrix-Assisted Laser Desorption/Ionization for Short Tandem Repeat Loci", Rapid Comm. Mass Spec., 12:413-418 (1998).

Tas et al., "Characterization of Virus Infected Cell Cultures by Pyrolysis/Direct Chemical Ionization Mass Spectrometry", Biomed. Environ. Mass Spec., 18(9):757-760 (1989).

The Utah Marker Development Group, "A Collection of Ordered Tetranucleotide-Repeat Markers from the Human Genome", Am. J. Hum. Genet., 57:619-628 (1995).

Tomasz et al., "On the Stability of Phosphodiester-amide Internucleotide Bond", Tetrahedron Lett., 22:3905-3908 (1981).

Tong et al., "Solid Phase Purification in Automated DNA Sequencing", J.DNA Sequencing and Mapping, 4:151-162 (1993).

Tong et al., "Solid-Phase Method for the Purification of DNA Sequencing Reactions", Anal. Chem., 64:2672-2677 (1992).

Trainor, "DNA Sequencing, Automation, and the Human Genome", Anal. Chem., 62:418-426 (1990).

Uhlmann et al., "Antisense Oligonucleotides: A New Therapeutic Principle", Chemical Reviews, 90(4):543-584 (1990).

Van Ness et al., "A Versatile Solid Support System for Oligodeoxynucleotide Probe-Based Hybridization Assays", Nucl. Acids Res., 19:3345-3350 (1991).

Walker et al., "Isothermal in vitro Amplification of DNA by a Restriction enzyme/DNA Polymerase System", Proc. Natl. Acad. Sci. USA, 89:392-396 (1992).

Wang et al., "2-Phosphoglycolate and Glycolate-Electophore Detection, Including Detection of 87 Zeptomoles of the Latter by Gas Chromatography-Electron-Capture Mass Spectrometry", J. Chromatography A, 721:289-296 (1996).

Wang et al., "DNA Sequencing from Single Phage Plaques Using Solid-Phase Magnetic Capture", BioTech., 18(1):130-135 (1995).

Watson et al., "Recombinant DNA", Second ed., Scientific American, Inc., Chapter 27, pp. 539-566 (1992).

Weber et al., "Abundant Class of Human DNA Polymorphisms which can be Typed Using the Polymerase Chain Reaction"Am. J. Hum. Genet., 44:388-396 (1989).

Welham et al., "The Rapid Identification of Intact Microorganisms by Matrix-Assisted Laser Desorption/Ionization Time-of-Flight Mass Spectrometry", Pharm. Pharmacol. Comm., 4(2):81-87 (1998).

Wenz et al., "High-Precision Genotyping by Denaturing Capillary Electrophoresis", Genome Res., 8:69-80 (1998).

Wu et al., "Matrix-Assisted Laser Desorption Time-of-Flight Mass Spectrometry of Oligonucleotides Using 3-Hydroxypicolinic Acid as an Ultraviolet-sensitive Matrix", Rapid Commun. in Mass Spectrometry, 7:142-146 (1993).

Wu et al., "The Ligation Amplification Reaction (LAR)—Amplification of Specific DNA Sequences Using Sequential Rounds of Template-Dependent Ligation", Genomics, 4:560-569 (1989).

Wu et al., "Time-of-Flight Mass Spectrometry of Underivatized Single-Stranded DNA Oligomers by Matrix-Assisted Laser Desorption", Anal. Chem., 66:1637-1645 (1994).

Yamamoto et al., "One-step Synthesis of 5'-Aziod-nucleosides", J. Chem. Soc., Perkin Trans. 1, 1:306-310 (1980).

Youil et al., "Screening for Mutations by Enzyme Mismatch Cleavage with T4 Endonuclease VII", Proc. Natl. Acad. Sci. USA, 92:87-91 (1995).

Youngquist, et al., "Matrix-Assisted Laser Desorption Ionization for Rapid Determination of the Sequences of Biologically Active Peptides Isolated from Support-Bound Combinatorial Peptide Libraries", Rapid Comm. Mass Spec., 8:77-81 (1994).

Zhang et al., "Single-Base Mutational Analysis of Cancer and Genetic Diseases Using Membrane Bound Modified Oligonucleotides", Nucl. Acids Res., 19:3929-3933 (1991).

Ziegle et al., "Application of Automated DNA Sizing Technology for Genotyoing Microsatellite Loci", Genomics, 14:1026-1031 (1992).

Mass Spec

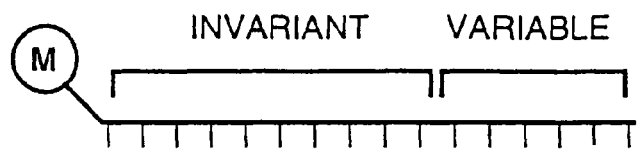
FIG. 3A
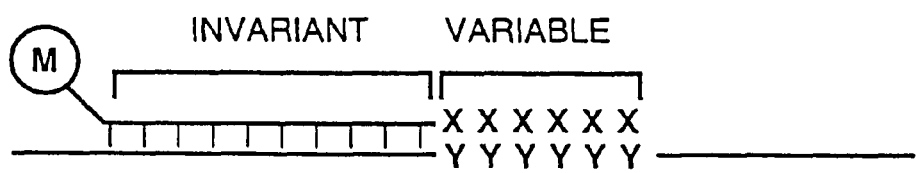
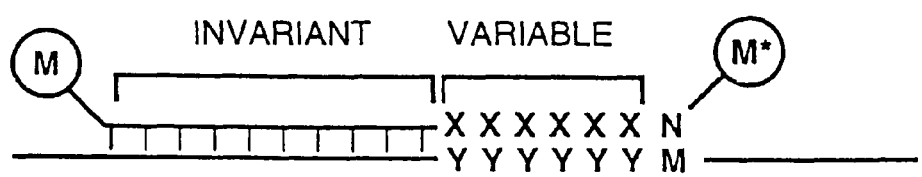
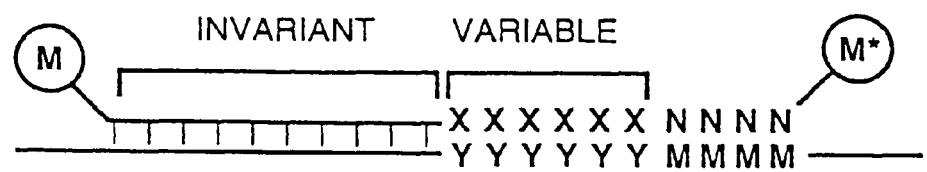
FIG. 3B

A 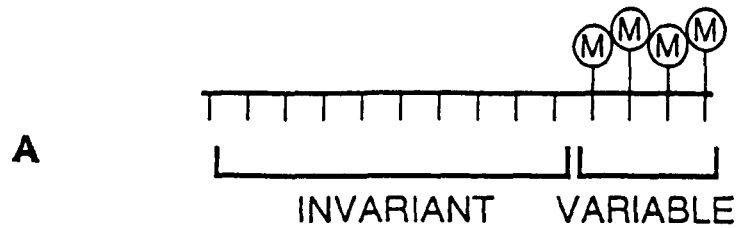
INVARIANT   VARIABLE
B 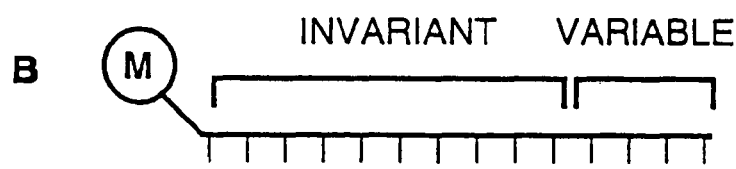
INVARIANT   VARIABLE
C
| Mass label | Sequence |
|---|---|
| 1 | ANNN |
| 2 | CNNN |
| 3 | GNNN |
| 4 | TNNN |
| 5 | NANN |
| 6 | NCNN |
| 7 | NGNN |
| 8 | NTNN |
| 9 | NNAN |
| . | . . . |
| 15 | NNNG |
| 16 | NNNT |
Examples
| Sequence | Combinatorial Label |
|---|---|
| ACAT | 1,6,9,16 |
| GGTC | 3,7,12,14 |
| CATG | 2,5,12,15 |
FIG. 4A

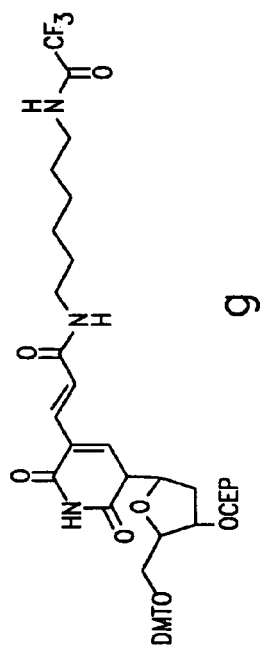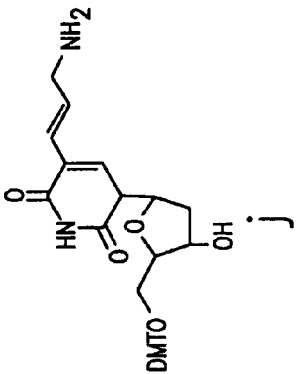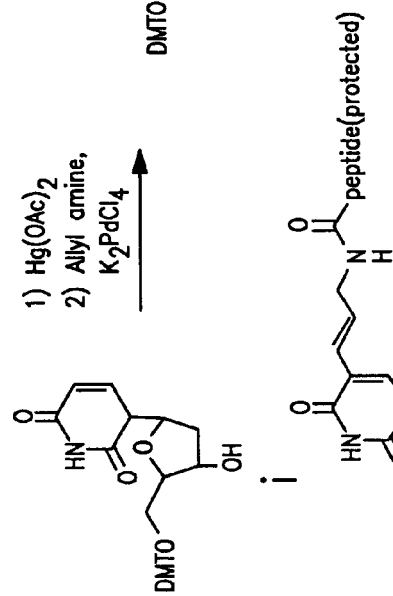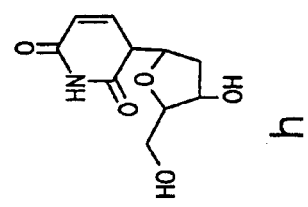
FIG. 6C
FIG. 6B

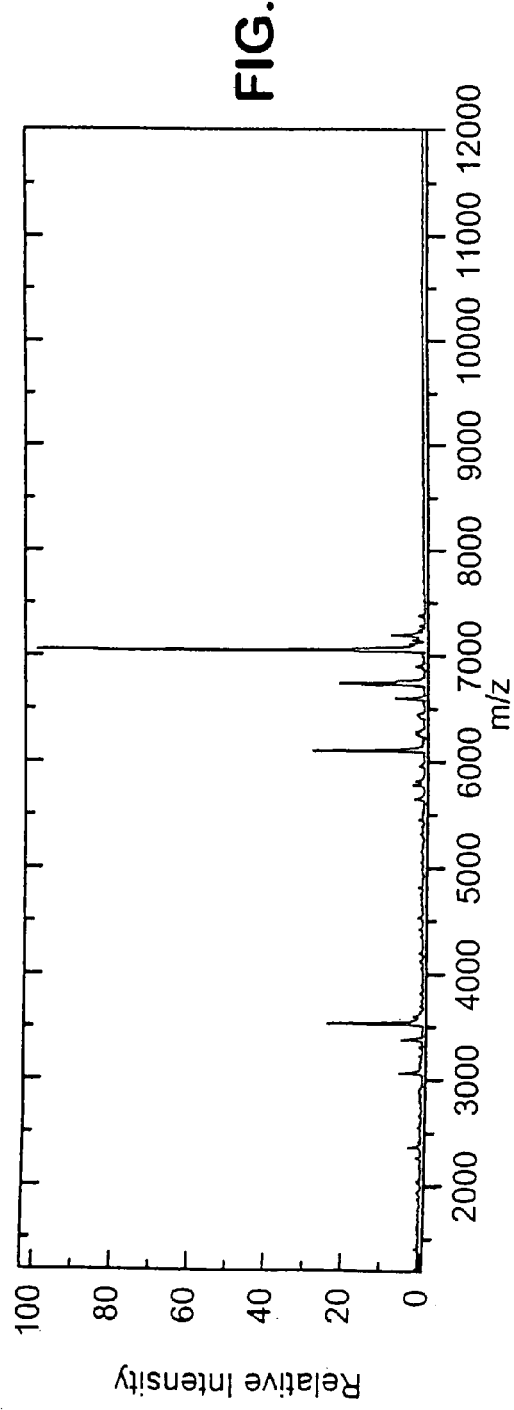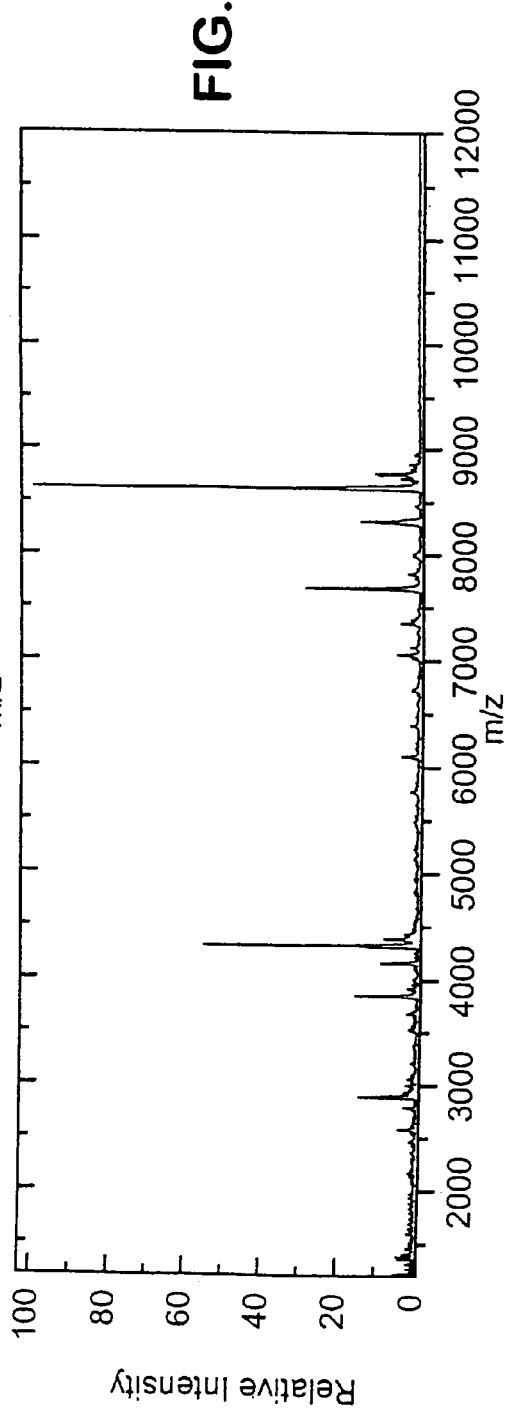

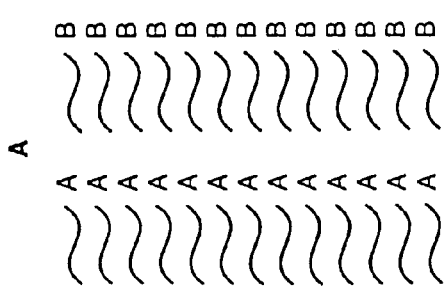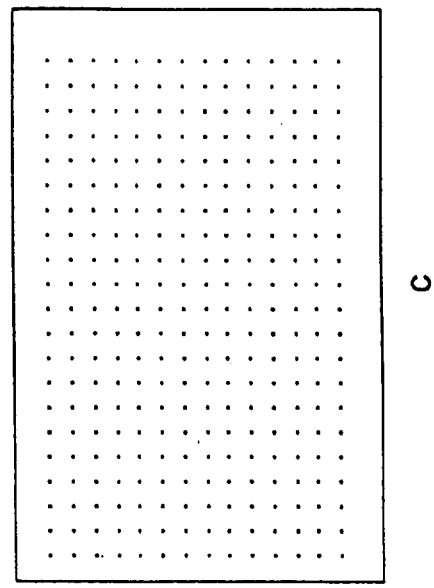
FIG. 10A

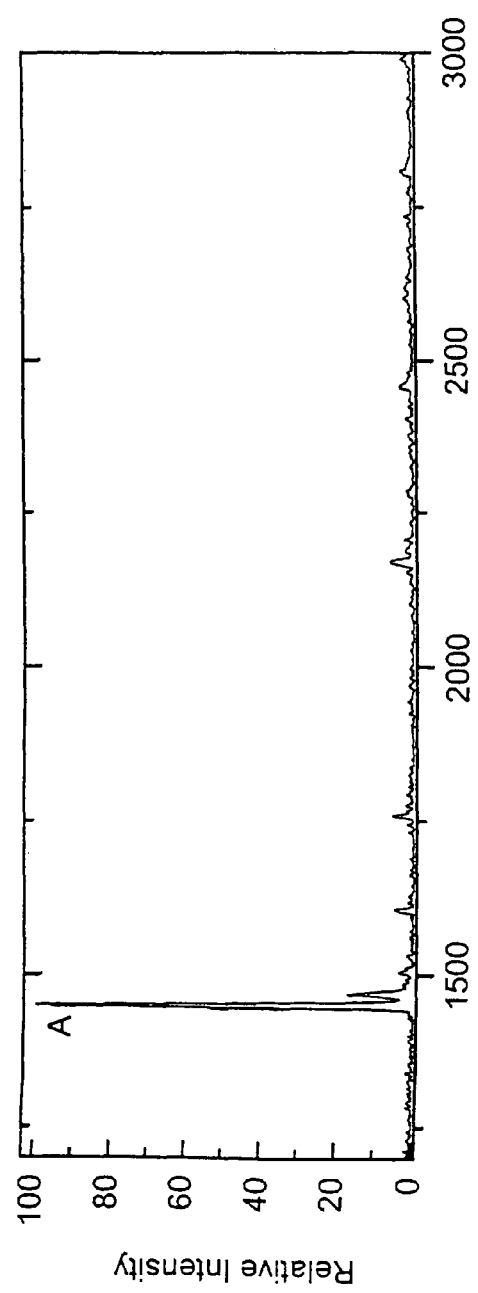
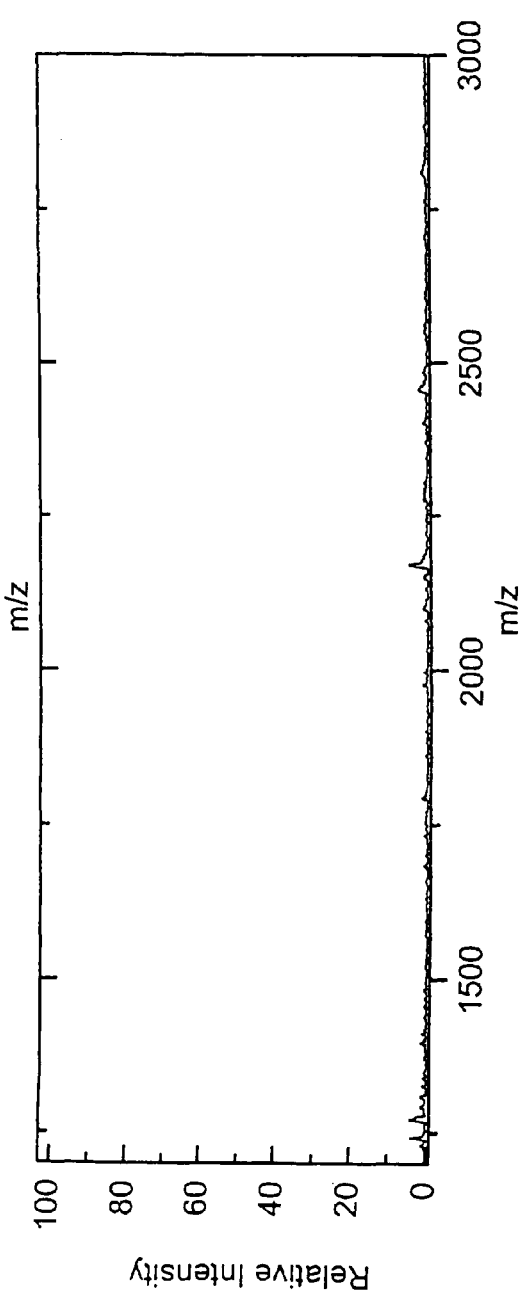
FIG. 17A
FIG. 17B

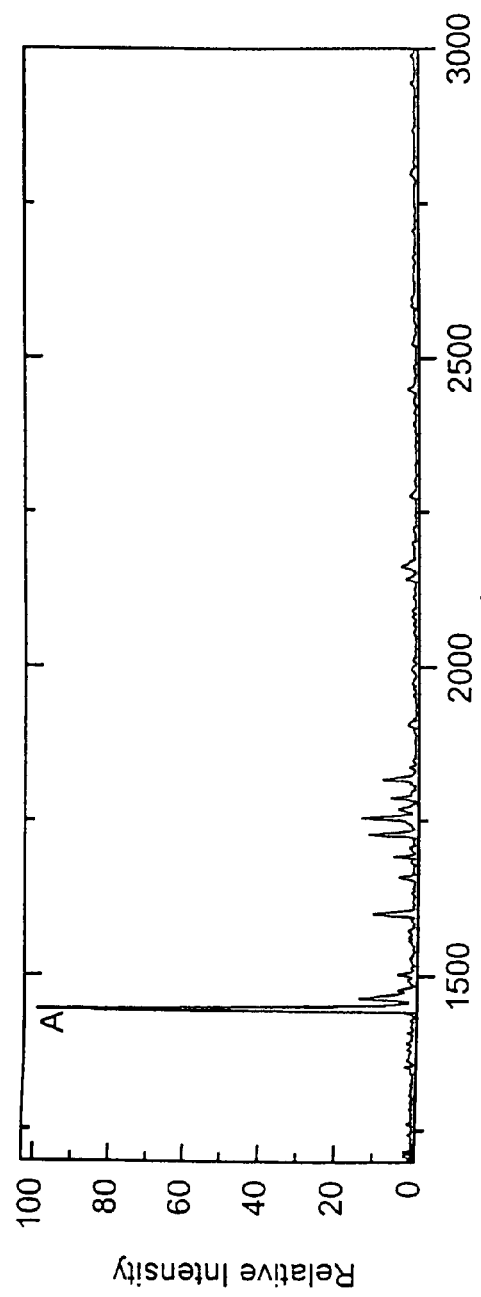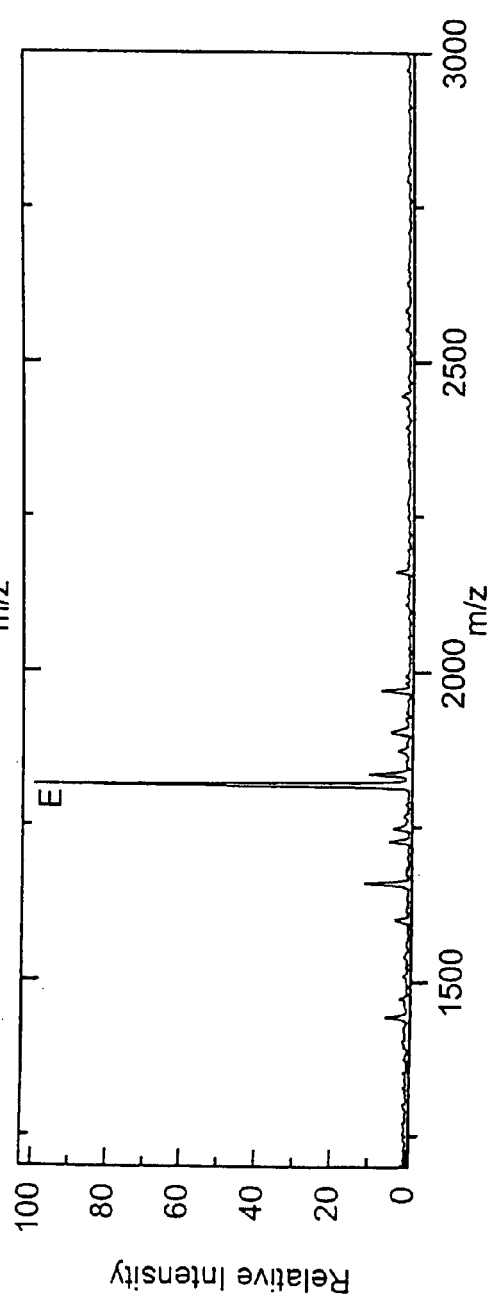
FIG. 20A
FIG. 20B

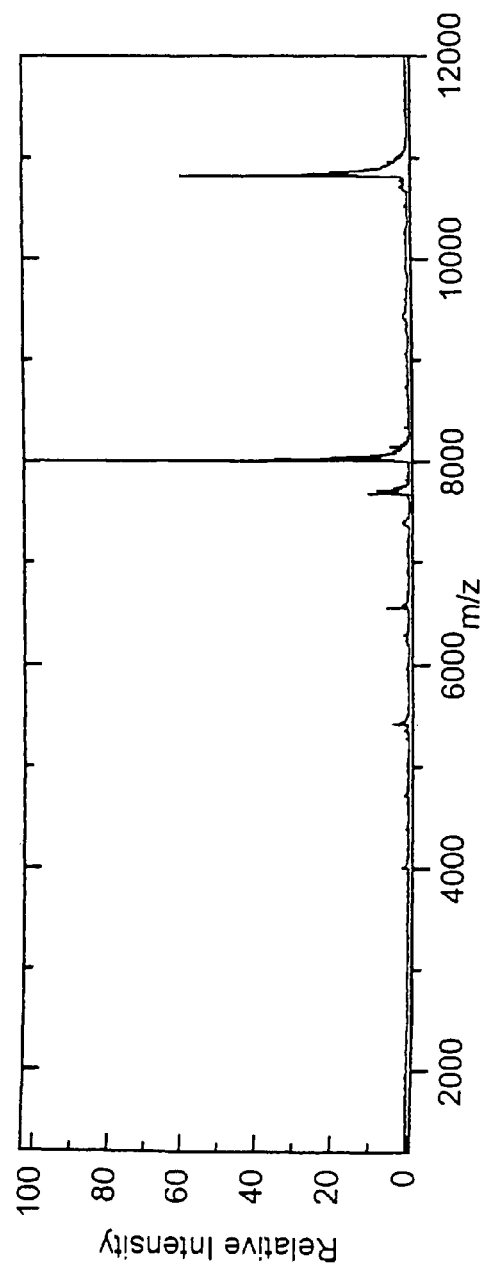
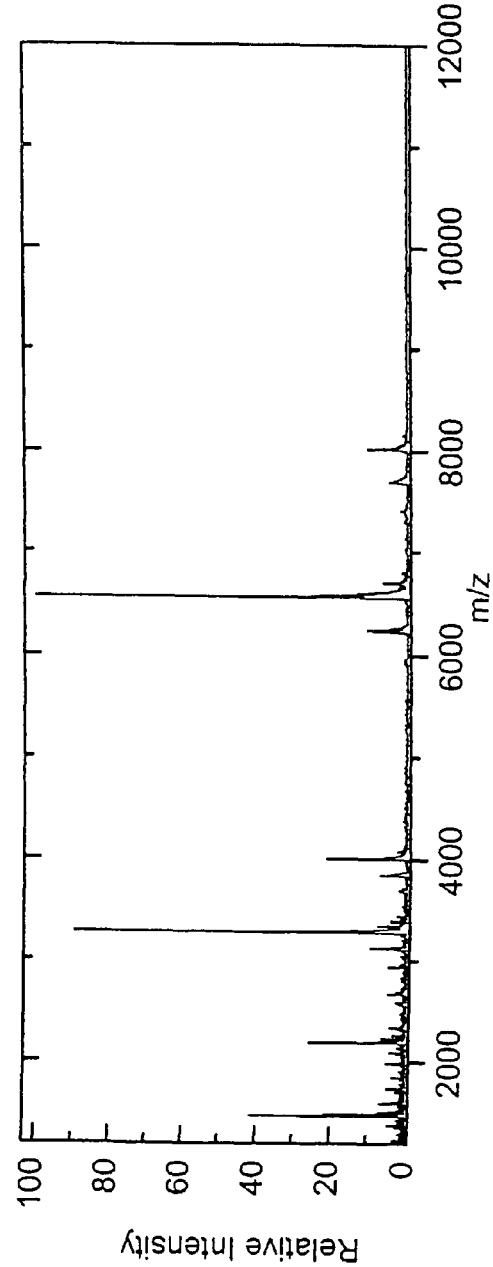
FIG. 21A
FIG. 21B

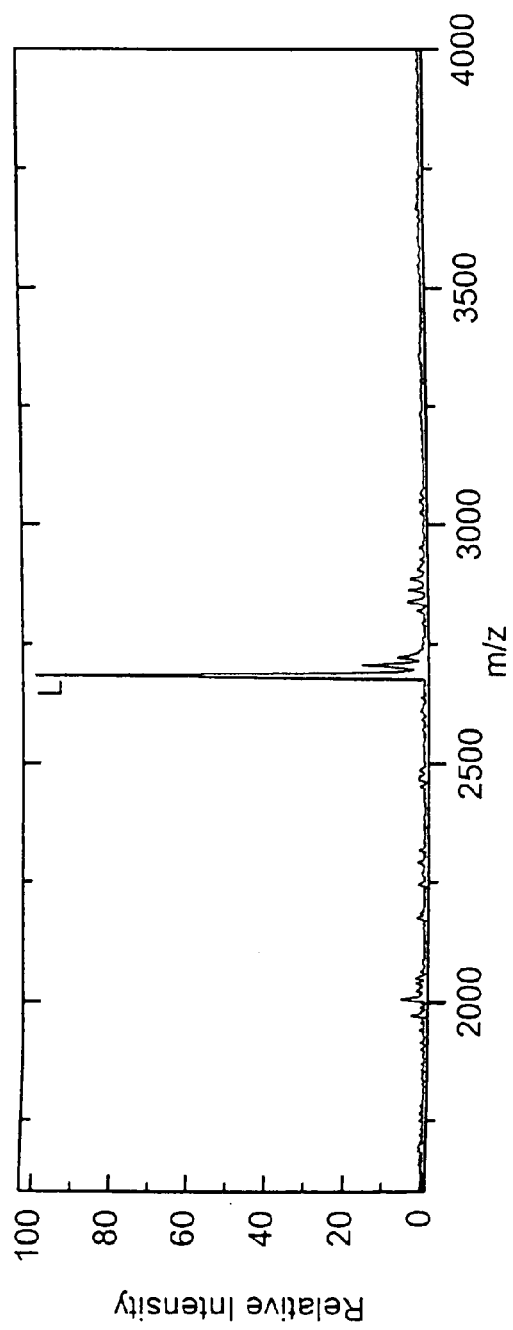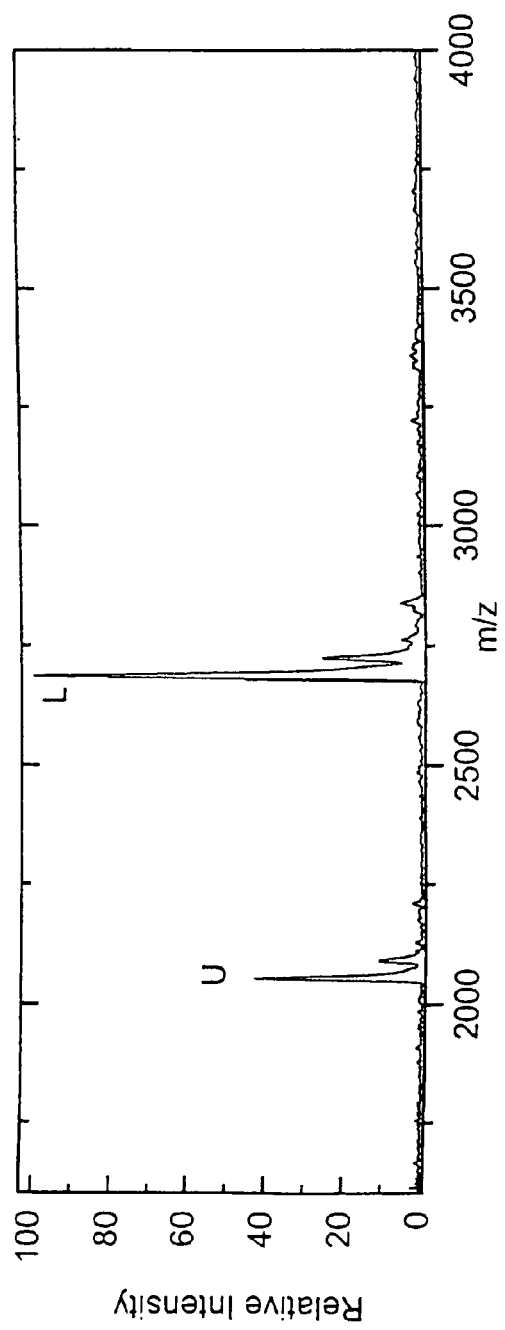
FIG. 22A
FIG. 22B

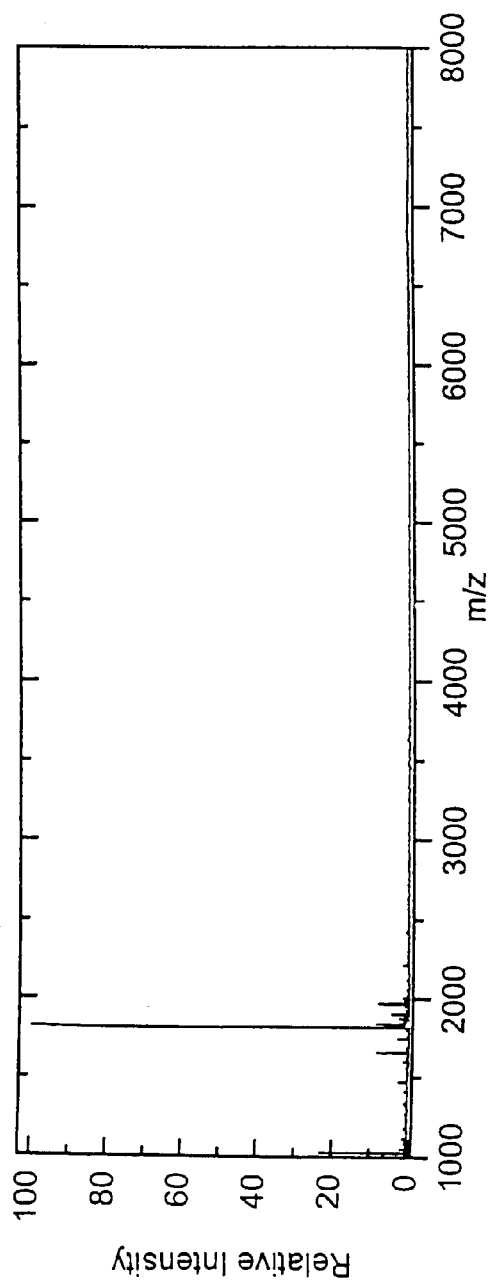
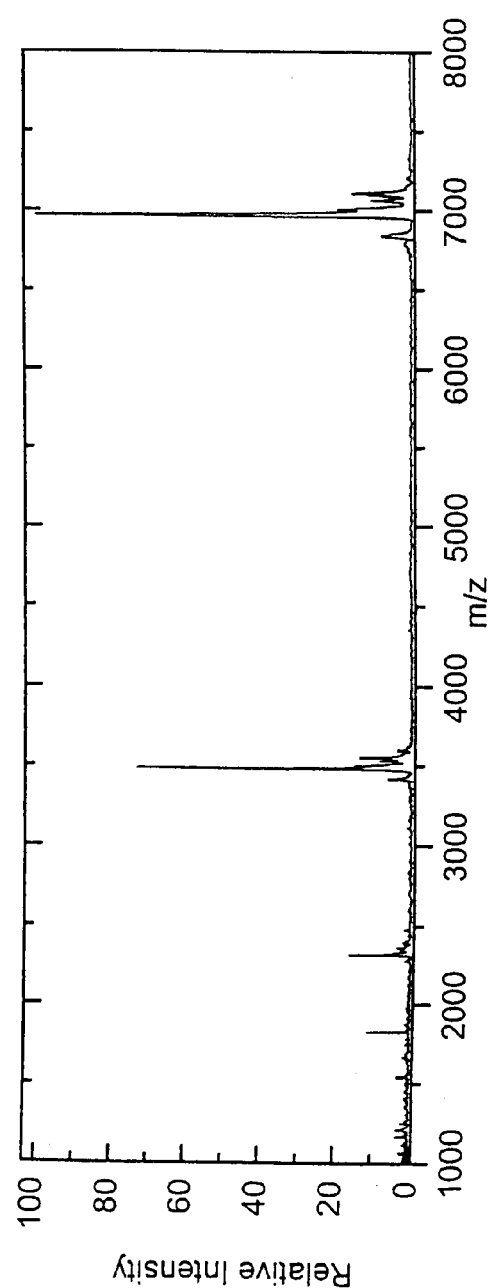
FIG. 23A
FIG. 23B

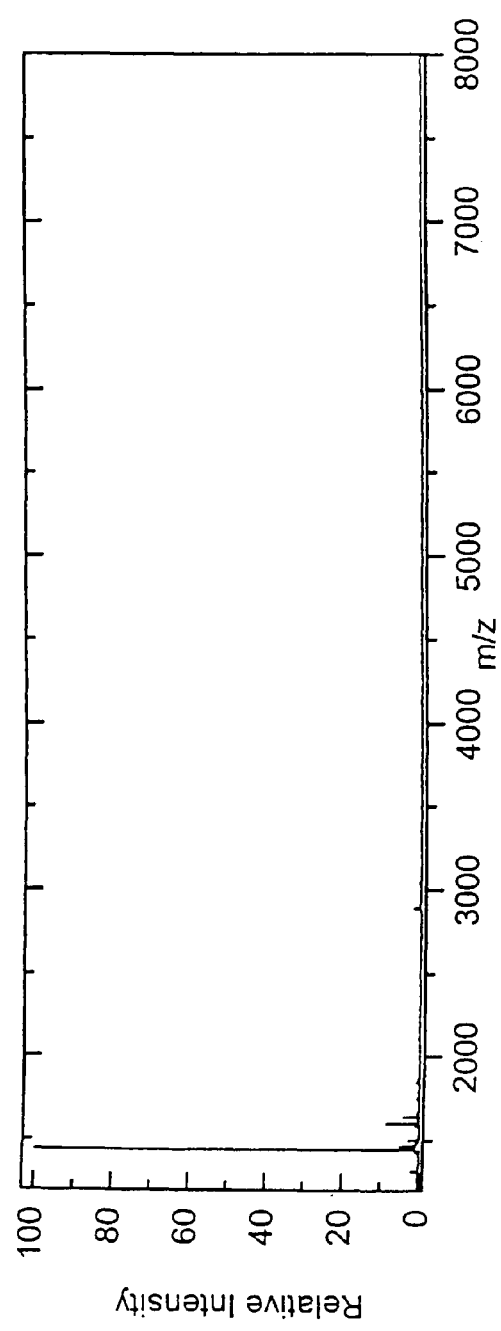
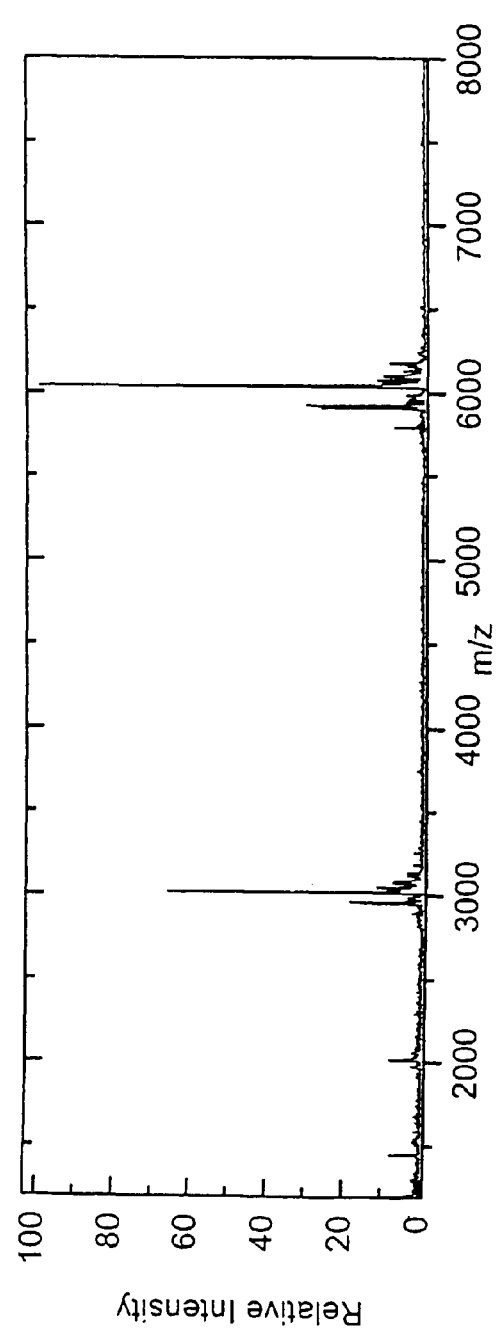
FIG. 23C
FIG. 23D

Mass Spec

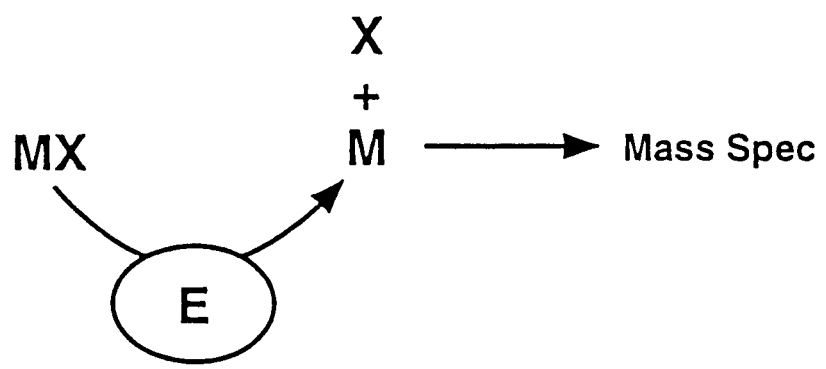
Examples
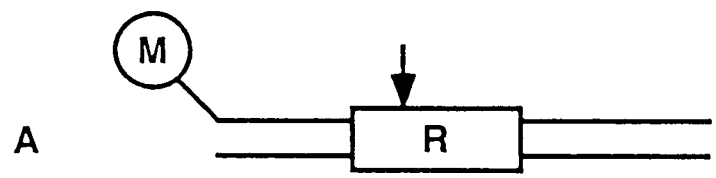
A
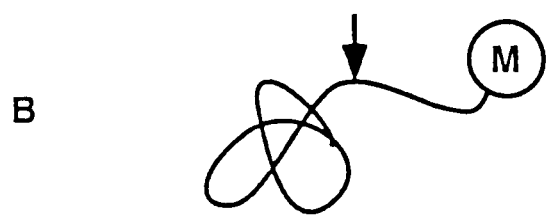
B
FIG. 26

RELEASABLE NONVOLATILE MASS-LABEL MOLECULES

RELATED APPLICATION

This application is a continuation of U.S. application Ser. No. 10/202,189, filed Jul. 22, 2002, now U.S. Pat. No. 7,132,519 to Monforte, Joseph A., Becker, Christopher H., Pollart, Daniel J., and Shaler, Thomas A., entitled "Releasable Nonvolatile Mass-Label Molecules," which is a continuation of U.S. application Ser. No. 08/988,024, filed Dec. 10, 1997 now U.S. Pat. No. 6,635,452. Benefit of priority under 35 U.S.C. §119(e) is also claimed to U.S. provisional application Ser. No. 60/033,037, filed Dec. 10, 1996, and Ser. No. 60/046,719, filed May 16, 1997. The subject matter of each of these applications is incorporated by reference in its entirety.

The government may own rights in subject matter herein pursuant to Cooperative Agreement No. 70NANB5H1029 from the United States Department of Commerce, Advanced Technology Program.

BACKGROUND OF THE INVENTION

1. Field of the Invention

The present invention relates generally to the field of chemical analysis. More particularly, it concerns a new class of nonvolatile, releasable tag reagents for use in the detection and analysis of target molecules i.e., mass spectrometry.

2. Description of Related Art

Chemical labels, otherwise known as tags or signal groups, are widely used in chemical analysis. Among the types of molecules used are radioactive atoms, fluorescent reagents, luminescent reagents, metal-containing compounds, electron-absorbing substances and light absorbing compounds. Chemical signal groups can be combined with reactivity groups so that they might be covalently attached to the target, the substance being detected. In many cases, however, chemical moieties present on the target may interfere with the detection of the signal group or not allow for measurement of the signal group in an optimal detection environment.

Indirect detection of the target is oftentimes, therefore, preferred. For example, the signal group may be the product of the degradation of the target or a derivative of the target (Bueht et. al., 1974; Senft, 1985; U.S. Pat. No. 4,650,750; U.S. Pat. No. 4,709,016; U.S. Pat. No. 4,629,689). Volatile releasable tag compounds that can be analyzed using various forms of electron-attachment mass spectrometry, often with gas chromatography-mass spectrometry (GC-MS), have been described (Wang et al., 1996; U.S. Pat. No. 5,360,819; U.S. Pat. No. 5,516,931). Despite the broad range of volatile mass labels reported, a transition from liquid to gas phase is required for analysis which places significant synthetic and size parameters on the label. Isotopic mass labels have also been described, such as using tin or sulfur isotopes, with various mass spectrometric sampling approaches (Arlinghaus et al. 1997; U.S. Pat. No. 5,174,962). The isotopic labeling often limits the extent of multiplexing and provides a more complex analysis requirement.

Mass spectral analysis of signal groups involves none of the concerns related to radioactive signal groups, such as their short half-lives and their safety and disposal issues. Another key advantage to detection of signal groups via mass spectrometry is that it allows a great ability to multiplex, to detect for more than one signal group in a complex mixture, and therefore more than one target at a time. Brummel et al. (1994; 1996) have demonstrated the use of mass spectrometry in the direct analysis of combinatorial libraries of small peptides. However, use of this technology is limited to analysis of the entire reacting compound by mass spectrometry.

Detection of multiple fluorescent labels has been used to analyze nucleic acid sequences. Nucleic acid hybridization probes are modified to contain fluorescent chromophores that when excited by light emit a unique color spectrum signature. In fluorescence based sequencing systems, four different chromophores can be multiplexed within a sample and individually detected with the aid of software deconvolution. The practical upper limit for fluorescence multiplexing is likely to be around 10 different labels due to the broad overlapping spectrum produced by existing fluorescent chromophores. Clearly the development of nonvolatile releasable mass labels, detectable over the usable range of a mass spectrometer, would represent a significant advantage by permitting the multiplexing of tens, hundreds and perhaps even thousands of different mass labels that can be used to uniquely identify each desired target.

At present, while tools are available through which target molecules may be detected, there remains a need for further development of these systems in order to analyze a large number of targets simultaneously. This will allow for the systematic analysis of target molecules with predetermined properties and functions.

SUMMARY OF THE INVENTION

It is, therefore, a goal of the present invention to provide compositions and methods relating to the use of release tag compounds for detection and analysis of target molecules.

The present invention relates to the use of nonvolatile, releasable tag compounds, containing releasable mass labels, in chemical analysis, and to the use of these reagents in conjunction with probes which react with or bind noncovalently to a molecule whose presence is to be detected. The releasable tag reagents thus may indirectly detect target molecules, including biomolecular targets. The mass label may be released from the probe following reaction with or binding of the probe to the target and detected by mass spectrometry. The mass value of the label identifies and characterizes the probe and, therefore, the target molecule. In the case of a mass-labeled oligonucleotide probe used to target a polynucleotide, the detection of mass-labels rather than the nucleic acid probes or the nucleic acid targets themselves means that biochemical analysis procedures can be greatly simplified. The need for slow, laborious, costly, and/or complex solid-phase and/or solution-phase cleanup and desalting procedures can be minimized or even, eliminated.

Therefore, in accordance with the present invention, there is provided a release tag compound comprising Rx, Re and M, wherein Rx is a reactive group, Re is a release group, and M is a mass label detectable by mass spectrometry. As used herein the term "a" encompasses embodiments wherein it refers to a single element as well as embodiments including one or more of such elements. For example, the phrase "a reactive group: may refer to a single reactive group, but also encompasses embodiments including more than one reactive group.

Although the mass label may typically be a synthetic polymer or a biopolymer or some combination thereof, in some embodiments, the mass label may generally be any compound that may be detected by mass spectrometry. In particular embodiments, the mass label may be a biopolymer comprising monomer units, wherein each monomer unit is separately and independently selected from the group consisting essentially of an amino acid, a nucleic acid, and a saccharide with amino acids and nucleic acids being preferred monomer units. Because each monomer unit may be separately and independently selected, biopolymer mass labels may be polynucleic acids, peptides, peptide nucleic acids, oligonucleotides, and so on.

As defined herein "nucleic acids" refer to standard or naturally-occurring as well as modified/non-natural nucleic acids, often known as nucleic acid mimics. Thus, the term "nucleotides" refer to both naturally-occurring and modified/non-naturally-occurring nucleotides, including nucleoside tri, di, and monophosphates as well as monophosphate monomers present within polynucleic acid or oligonucleotide. A nucleotide may also be a ribo; 2'-deoxy; 2',3'-deoxy as well as a vast array of other nucleotide mimics that are well-known in the art. Mimics include chain-terminating nucleotides, such as 3'-O-methyl, halogenated base or sugar substitutions; alternative sugar structures including nonsugar, alkyl ring structures; alternative bases including inosine; deaza-modified; chi, and psi, linker-modified; mass label-modified; phosphodiester modifications or replacements including phosphorothioate, methylphosphonate, boranophosphate, amide, ester, ether; and a basic or complete internucleotide replacements, including cleavage linkages such as photocleavable nitrophenyl moieties. These modifications are well known by those of skill in the art and based on fundamental principles as described Saenger (1983), incorporated herein by reference.

Similarly, the term "amino acid" refers to naturally-occurring amino acid as well as any modified amino acid that may be synthesized or obtained by methods that are well known in the art.

In another embodiment, the mass label may be a synthetic polymer, such as polyethylene glycol, polyvinyl phenol, polyproplene glycol, polymethyl methacrylate, and derivatives thereof. Synthetic polymers may typically contain monomer units selected from the group consisting essentially of ethylene glycol, vinyl phenol, propylene glycol, methyl methacrylate, and derivatives thereof. More typically the mass label may be a polymer containing polyethylene glycol units.

The mass label is typically detectable by a method of mass spectrometry. While it is envisioned that any known mass spectrometry method may be used to detect the mass labels of the present invention, methods such as matrix-assisted laser-desorption ionization mass spectrometry, direct laser-desorption ionization mass spectrometry (with no matrix), electrospray ionization mass spectrometry, secondary neutral mass spectrometry, and secondary ion mass spectrometry are preferred.

In certain embodiments the mass label has a molecular weight greater than about 500 Daltons. For some embodiments, it may be preferred to have nonvolatile (including involatile) mass labels, however, for other embodiments volatile mass labels are also contemplated.

As defined herein, the term "reactive group" refers to a group capable of reacting with the molecule whose presence is to be detected. For example, the reactive group may be a biomolecule capable of specific molecular recognition. Biomolecules capable of specific molecular recognition may typically be any molecule capable of specific binding interactions with unique molecules or classes of molecules, such as peptides, proteins, polynucleic acids, etc.

Thus, reactive groups disclosed herein for use with the disclosed methods encompass polypeptides and polynucleic acids. As used herein, polypeptides refer to molecules containing more than one amino acid (which include native and non-native amino acid monomers. Thus, polypeptides includes peptides comprising 2 or more amino acids; native proteins; enzymes; gene products; antibodies; protein conjugates; mutant or polymorphic polypeptides; post-translationally modified proteins; genetically engineered gene products including products of chemical synthesis, in vitro translation, cell-based expression systems, including fast evolution systems involving vector shuffling, random or directed mutagenesis, and peptide sequence randomization. In preferred embodiments polypeptides may be oligopeptides, antibodies, enzymes, receptors, regulatory proteins, nucleic acid-binding proteins, hormones, or protein product of a display method, such as a phage display method or a bacterial display method. More preferred polypeptide reactive groups are antibodies and enzymes. As used herein, the phrase "product of a display method" refers to any polypeptide resulting from the performance of a display method which are well known in the art. It is contemplated that any display method known in the art may be used to produce the polypeptides for use in conjunction with the present invention.

Similarly, "polynucleic acids" refer to molecules containing more than one nucleic acid. Polynucleic acids include lengths of 2 or more nucleotide monomers and encompass nucleic acids, oligonucleotides, oligos, polynucleotides, DNA, genomic DNA, mitochondrial DNA (mtDNA), copy DNA (cDNA), bacterial DNA, viral. DNA, viral RNA, RNA, message RNA (mRNA), transfer RNA (tRNA), ribosomal RNA (rRNA), catalytic RNA, clones, plasmids, M13, P1, cosmid, bacteria artificial chromosome (BAC), yeast artificial chromosome (YAC), amplified nucleic acid, amplicon, PCR product and other types of amplified nucleic acid. In preferred embodiments, the polynucleic acid may be an oligonucleotide.

In still further embodiments, Rx is an oligonucleotide having one or more nucleotides or oligonucleotide is added after hybridization of Rx to a complementary nucleic acid sequence. The term complementary generally refers to the formation of sufficient hydrogen bonding between two nucleic acids to stabilize a double-stranded nucleotide sequence formed by hybridization of the two nucleic acids.

Typically, nucleotides may be added by a polymerase while oligonucleotides may be added by a ligase. However, it is also contemplated that other methods of adding nucleotides and oligonucleotides known by those of skill in the art may also be employed. In further embodiments, it is provided that the nucleotide added after hybridization may have a chain terminating modification, for example, the added nucleotide may be a chain terminating dideoxy nucleotide.

Embodiments are also provided wherein the added nucleotide or oligonucleotide further comprise a functional group capable of being immobilized on a solid support, for example, a biotin or digoxigenin. Generally, this functional group or binding group or moiety is capable of attaching or binding the tag compound to the solid support. This binding moiety may be attached to the added nucleotide or oligonucleotide directly through an intervening linking group or by specific hybridization to an intermediary oligonucleotide which is itself bound to a solid support. Binding moieties include functional groups for covalent bonding to a solid support, ligands that attach to the solid support via a high-affinity, noncovalent interaction (such as biotin with streptavidin), a series of bases complementary to an intermediary oligonucleotide which is itself attached to the solid support, as well as other means that are well-known to those of skill in the art, such as those described in PCT WO 96/37630, incorporated herein by reference.

In other embodiments, the reactive group may contain a nuclease blocking moiety. These moieties serve to block the digestion of the oligonucleotide by the nuclease, such as an exonuclease. Typical nuclease blocking moieties thus include phosphorathioate, alkylsilyldiester, boranophosphate, methylphosphonate, and peptide nucleic acid.

The mass label is linked, or attached, to the reactive group via a releasable attachment. Thus, typically the mass label is released from all or a part of the reactive group prior to mass spectral analysis as contemplated by the various methods described herein. This releasable attachment typically occurs through the use of a release group which may be the linkage between the mass label and the reactive group or which may comprise a portion or all of the reactive group or which may be contained within the reactive group.

The release group may be any labile group providing for such a releasable attachment. The release group may thus be a chemically cleavable linkage or labile chemical linkage. Such linkages may typically be cleaved by methods that are well known to those of skill in the art, such as by acid, base, oxidation, reduction, heat, light, or metal ion catalyzed, displacement or elimination chemistry. In a particular embodiment, the chemistry cleavable linkage comprises a modified base, a modified sugar, a disulfide bond, a chemically cleavable group incorporated into the phosphate backbone, or a chemically cleavable linker. Some examples of these linkages are described in PCT WO 96/37630, incorporated herein by reference. As used herein, "chemically cleavable linkers" are moieties cleavable by, for example, acid, base, oxidation, reduction, heat, light, metal ion catalyzed, displacement or elimination chemistry.

Chemically cleavable groups that may be incorporated into the phosphate backbone are well known to those of skill in the art and may include dialkoxysilane, 3'-(S)-phosphorothioate, 5'-(S)-phosphorothioate, 3'-(N)-phosphoroamidate, or 5'-(N)-phosphoroamidate. In further embodiments the chemically cleavable linkage may be a modified sugar, such as ribose. Alternatively, the linkage may be a disulfide bond.

In still yet another embodiment, Re is contained within Rx. In this case, the release of Re may be activated by a selective event. In particular embodiments, the selective release is mediated by an enzyme such as an exonuclease specific for double-stranded or single-stranded DNA. When it is said that Re is contained within Rx, it will generally be understood that the reactive group contains within its structure the particular release group which will cause the mass label to disconnect from the tag compound in that particular embodiment.

Thus, release groups encompassed by the invention also include groups or linkages cleavable by an enzyme. Enzymatically-cleavable release groups include phosphodiester or amide linkages as well as restriction endonuclease recognition sites.

Preferred embodiments encompass release groups cleavable by nucleases. These nucleases may typically be an exonuclease or a restriction endonuclease. Typical exonucleases include exonucleases specific for both double-stranded and single-stranded polynucleic acids. Additionally, restriction endonucleases encompassed by certain embodiments include Type IIS and Type II restriction endonucleases.

In other embodiments the release group may be cleavable by a protease. Typical proteases include endoproteinases.

Also provided are embodiments wherein Rx comprises a nucleoside triphosphate or is synthesized using mass-labeled nucleoside triphosphates. In another embodiment, Rx comprises a nucleoside phosphoramidite or is synthesized using mass-labeled nucleoside phosphoramidites.

In still further embodiments, mass-labeled probes are provided wherein at least one component is a nucleoside triphosphate. It is further contemplated that the labeled probes of the invention may include at least two unique mass-labels are incorporated.

Also provided are release tag compounds comprising Rx, Re and M, wherein Rx is a double-stranded oligonucleotide comprising a restriction endonuclease recognition site; Re is a release group comprising a phosphodiester linkage capable of being cleaved by a restriction endonuclease; and M is a mass label detectable by mass spectrometry. Rx may further include a modified nucleotide and the mass label may include a portion of Rx.

Double-stranded oligonucleotides as provided herein include not only two complementary strands hybridized to each other via hydrogen bonding interactions, but also include single strands of nucleotides wherein portions of the strand are single-stranded and portions are double-stranded. For example, portions or all of Rx may include a self-complementary oligonucleotide hairpin where part of Rx is complementary to another part of Rx. In this case, certain conditions allow the formation of a double-stranded duplex between these two portions of Rx. For purposes of certain embodiments of the present invention, it is not necessary that all of Rx need be double-stranded, release tag compounds containing single-stranded regions are also contemplated as being within this embodiment.

Release tag compound are also contemplated having Rx, Re and M, wherein: Rx is a double-stranded oligonucleotide; Re is a chemically cleavable release group and M is a mass label detectable by mass spectrometry. In this embodiment, Re is typically located within Rx. Cleavage at the chemically cleavable release group is generally inhibited in this aspect by the presence of a double-stranded oligonucleotide at the release group. Previously discussed chemically cleavable release groups, such as 3'-(S)-phosphorothioate, 5'(S)-phosphorothioate, 3'-(N)-phosphoroamidate, 5'-(N)-phosphoroamidate, or ribose, may be employed with these embodiments. In these embodiments, a portion of Rx may be rendered single-stranded at Re by hybridization of a portion of Rx to a target nucleic acid.

Also provides is a set of release tag compounds for detecting a particular target nucleic acid. In this aspect, the target nucleic acid typically contains more than one release tag compound. Each release tag compound includes the elements Rx, Re and M, where Rx is an oligonucleotide including a variable region and an invariant region; Re is a release group; and M is a mass label detectable by mass spectrometry. The invariant and variable regions react with the target nucleic acid. It will generally be understood by those of skill in the art that the term "set" refers to a group of two or more release tag compounds. Generally each member, i.e., each release tag compound of the group will be different from all other members of the group. That is, each member will include a different combination of reactive group release group and mass label.

Typically, the mass label of at least one member of the set may identify a specific sequence within the variable region. In some embodiments, the mass label for each member of the set may uniquely identify each different sequence within the variable region. In other embodiments, a combination of the mass labels of two or more release tag compounds may identify each different sequence within the variable region.

As previously discussed, Rx may further comprise a nucleotide or oligonucleotide added after hybridization to the target nucleic acid. In this aspect, the added nucleotide or oligonucleotide may further comprise Re' and M', where Re' is a release group; and M' is a mass label detectable by mass spectrometry. The added nucleotide or oligonucleotide may also contain a chain terminating moiety or a functional group capable of being immobilized on a solid support, such as biotin or digoxigenin.

Methods of producing a mass-labeled probe are provided, comprising combining nucleoside or amino acid monomers with at least one mass-labeled monomer under conditions to allow for polymerization.

Further embodiments are provided wherein the polymerization is mediated by an enzyme. Still further embodiments are provided wherein the polymerization is mediated by chemical synthesis. The preferred synthetic methods to prepare the compound of the present invention are essentially those for standard peptide and DNA synthesis.

For particular embodiments, synthesis in the solid phase is preferred to allow for a wide variety of compounds to be produced using combinatorial methods.

Additional embodiments are provided for a method of producing a mass-labeled probe, comprising the steps of (a) combining nucleoside monomers with at least one activated nucleoside monomer under conditions to allow for polymerization; and (b) adding a releasable, nonvolatile mass unit to said activated nucleoside monomer.

The present invention also provides embodiments which provide a method for detecting a target molecule. Generally, the method includes obtaining a plurality of probes, each probe including a reactive group, a release group and a mass label, as described. It is preferred that each probe within the plurality contains a unique mass-label. By "unique mass label" it is meant that each probe within the plurality will have a different mass label from all other probes in the plurality. A plurality will generally be understood to include two or more probes. Next, the target molecule is contacted with the plurality of probes under conditions suitable to allow for the formation of probe: target molecule complexes. The mass-label is released from the probe and the mass of the mass-label is determined. Typically, the mass is indicative of a specific target molecule. In this way, the target molecule can be identified according to the unique combination of mass-labels.

In another aspect, the invention provides a method for detecting a target molecule where the target molecule is amplified to produce an amplified target molecule. The amplified target molecule is then hybridized with a probe such as those described hereinabove to produce probe: amplified target molecule complexes. The mass label on the probe amplified target molecule complexes are then released and the mass of the mass label determined by mass spectrometry.

The target nucleic acid may be amplified by any method known by one of skill in the art, for example, polymerase chain reaction ("PCR"), with PCR being a preferred amplification method. The amplification may include a functional group capable of being immobilized on a solid support, such as biotin or digoxigenin. This functional group may be attached to an oligonucleotide primer incorporated into the amplified molecule during the amplification step or it may be attached to a nucleotide incorporated into the amplified target molecule during the amplification step.

Methods are also provided wherein the amplified target molecule is immobilized onto a solid support and any probe not part of a probe:amplified target molecule complex is removed by washing. It will be understood by those of skill in the art that the nature of the recognition of the target molecule by the reactive group will depend on the identity of the target molecule and the reactive group. For purposes of exemplification and not limitation, this recognition may encompass the formation of a double-stranded duplex by hybridization where the reactive group and target molecule are oligonucleotides. The mass label may be released enzymatically or chemically.

It is contemplated that useful enzymes for this embodiment will include nucleases, such as Type II and IIS restriction endonuclease and exonucleases. The envisioned exonucleases may be specific for double-stranded DNA, such as exonuclease III, T4 endonuclease VII, lambda exonuclease, and DNA polymerase. For these embodiments the release of the mass label may be triggered by the hybridization of the probe to the amplification product. In that embodiment the probe would be single-stranded and capable of hybridizing to the target whose presence was to be detected. The exonuclease may also be specific for single-stranded DNA.

chemically cleavable linkages may comprise a modified base, a modified sugar, a disulfide bond, a chemically cleavable group incorporated into the phosphate backbone, or a chemically cleavable linker and are typically cleaved by acid, base, oxidation, reduction, heat, light, or metal ion catalyzed, displacement or elimination chemistry.

Embodiments are provided wherein the reactive group further comprises a nucleotide or oligonucleotide added after hybridization to the amplification product, amplified target molecule or amplified nucleic acid molecule. These added nucleotides or oligonucleotides may optionally include a functional group capable of being immobilized on a solid support.

For embodiments employing immobilization onto a solid support, one will typically immobilize the reactive group onto the solid support after addition of the nucleotide or oligonucleotide then any probes having unbound reactive groups are removed prior to releasing the mass label of any probe belonging to a probe:amplified target molecule complex or probe:target molecule complex.

In these embodiments, the reactive and release groups may be the same or the release group may be contained within the reactive group. The probe may also comprise at least two unique mass labels.

Multiplexing methods are also provided wherein the target molecule is contacted with a plurality of probes. In these instances, each reactive group of the probe may be associated with a unique mass label or it may be associated with a unique set of mass labels. Thus, a target molecule may be detected by the mass spectral detection of a particular mass label or a particular set of mass labels. Where a set of mass labels is employed, the set of mass labels may be attached to the same probe. Alternatively, each member of the set may be attached to a different probe.

Also provided are methods for detecting mismatches wherein the amplified nucleic acid product comprises a double-stranded molecule containing a mismatch, and an exonuclease-blocking functionality at the 3' ends of the strands. Typically, this method may further comprise cleavage of at least one strand of the double-stranded molecule at the site of the mismatch; and selective releasing of the mass label. Selective releasing of the mass label may typically be accomplished by digestion of the cleaved strand by a 3' to 5' exonuclease, such as exonuclease III.

As used herein, the term "selective releasing" comprises to the releasing of a mass label from a probe which belongs to a probe:target molecule complex without releasing a mass label from a probe not belonging to such a complex without having to physically partition the two types of probes. However, some embodiments may include both selective releasing and physical partitioning. The described immobilization and washing techniques exemplify a method of physical partitioning.

The mismatch may be cleaved by an enzyme, such as mutHLS, T4 endonuclease VII, mutY DNA glycosylase, thymine mismatch DNA glycosylase, or endonuclease V. The mismatch may also be cleaved by a chemical, such as $OsO_4$, $HONH_2$, or $KMnO_4$.

The invention further provides a method for detecting a target molecule including the steps of: (a) obtaining a probe including a reactive group, a release group and a nonvolatile mass label; (b) contacting a target molecule with the probe to produce probe:target molecule complexes; (c) the selectively releasing the mass label from the probe:target molecule complexes to produce released mass labels; and (d) determining the mass of the released mass labels by mass spectrometry.

Typically, similar chemical and enzymatic release methods may be employed with these embodiments. Selective release of the mass label may also be accomplished by employing cleavage means that are inhibited by the presence of a double-stranded oligonucleotide at the said release group. As used in this context, "at said release group" means that base pairing is maintained on both sides of the release group by at least one nucleotide.

In this embodiment, contacting the probe with the target molecule typically results in the release group being present in a single-stranded region because one strand of the probe interacts with the target molecule, for example, by hybridizing to it.

Another aspect of the invention encompasses a method for multiplexing the detection of a target molecule including: (a) obtaining a plurality of probes, each probe including a reactive group, a release group and a mass label; (b) contacting the target molecule with the plurality of probes to produce probe:target molecule complexes; (c) releasing the mass label from any probe belonging to probe:target molecule complexes to produce released mass labels; and (d) determining the mass of any released mass label by mass spectrometry. In this aspect, each reactive group recognizing a specific target molecule is associated with a unique set of mass labels. It may often be preferred that a plurality of target molecules with the plurality of probes.

The members of the set of mass labels may be attached to the same probe or to different probes. Additionally, the same mass label may be a member of sets identifying more than one reactive group. Thus, in this embodiment the set of mass labels, and not the individual mass label, is unique to a particular reactive group. In this embodiment, probes having a reactive group that identifies a particular target may vary in release group and mass label as well as in other respects.

Immobilization and washing techniques may be employed with this embodiment and it may be preferred in some embodiments to immobilize a plurality of target molecules onto the solid support at spaced locations and to then contact them with the mass-labeled probes. Typical target molecules include a polynucleotide, an antigen, a ligand, a polypeptide, a carbohydrate, and a lipid.

In further embodiments it may be preferred to employ sets of mass labels wherein, a mass label member of the set represents a particular moiety or functionality or subset of the target molecule. For example, mass label A could correspond to a reactive group composed of $A'X_2 \ldots X_N$ functionalities where A can be anywhere in the reactive group and only represents A' and may or may not be structurally related to A' in any way. Thus, detecting mass label results in the detection of a target molecule that recognizes A', but does not necessarily identify anything else about that structure or composition of the target molecule.

Thus, methods are provided wherein the unique set of mass labels comprises a mass label that indicates the presence of a specified component within the reactive group. Further embodiments also include methods wherein the mass label indicates the presence of the specified component at a specified location within the reactive group. A reactive group comprising n specified components may be associated with a unique set of mass labels having n members where n may typically be from 1 to 1000. Generally, mass labels are individually attached to the reactive group and are identified intact.

A reactive group comprising n specified components may also be associated with a unique set of mass labels having y members wherein n is less than $y!/[x!(y-x)!]$; and wherein x comprises the number of mass labels per reactive group.

In some embodiments a plurality of probes may each comprise a known reactive group having a known set of mass labels and the plurality of probes may be prepared by combinatorial synthesis. The plurality of target molecules may also comprise a known chemical structure.

Also provided is a method of monitoring gene expression including (a) obtaining a plurality of probes, each including a reactive group, a release group and a mass label; (b) contacting a plurality of target nucleic acids with the plurality of proves to produce probe:target nucleic acid complexes; (c) selectively releasing the mass label from any probe belonging to a probe:target nucleic acid complexes to produce released mass labels; and (d) determining the mass of any released mass label by mass spectrometry.

Typically, the target nucleic acids may have sequences representative of the genes being expressed in a particular cell culture and are present in concentrations related to their MRNA abundance levels. The target nucleic acids may typically comprise mRNA or first-strand CDNA as well as amplified nucleic acid products.

Such amplified nucleic acid products may be produced using PCR, rtPCR, LCR, Qbeta Replicase, SDA, CPR, TAS, NASBA, or multiple rounds of RNA transcription of some combination thereof. Amplification may be used to selectively amplify a subset of the mBNA pool increasing detection signal for these gene products and reducing background from gene products outside of the amplified subset.

Another embodiment encompasses a method of monitoring gene expression including amplifying a subset of an MRNA pool to produce a plurality of amplified nucleic acid products; contacting a plurality of amplified nucleic acid products with a plurality of probes, each probe including a reactive group, a release group and a mass label to produce probe:amplified nucleic acid product complexes selectively releasing the mass label from any probe belonging to a probe: amplified nucleic acid produce complexes to produce released mass labels determining the mass of any released mass label by mass spectrometry.

For this embodiment, one more probes or amplified nucleic acid products may be capable of being immobilized onto a solid support.

Another aspect of the invention is a method for detecting a target molecule, including contacting a target molecule with a probe including a reactive group, a release group and a nonvolatile mass label to produce probe:target molecule complexes; releasing the mass label from any probe belonging to a complex to produce released mass labels; selectively desorbing the released mass label from the mass spectral matrix such that the probes not belonging to probe:target molecule complexes do not desorb; and determining the mass of the released mass label by mass spectrometry.

For these embodiments, the mass label should desorb more efficiently from the mass spectral matrix than the probe or the mass-labeled probe. Preferred mass spectral matrices include 2,5-dihydroxybenzoic acid, sinapinic acid, or alpha-cyano-4-hydroxycinammic acid.

A method for detecting a target molecule is also provided. This method includes amplifying one or more target nucleic acids to produce amplified nucleic acid products; incorporating one or more molecules including a reactive group, a release group and a nonvolatile mass label into the amplified nucleic acid product during the amplification process; selectively reldasing the mass labels incorporated into the amplified nucleic products to produce released mass labels; and determining the mass of the released mass labels by mass spectrometry.

Incorporated molecules may be oligonucleotide primers and nucleoside triphosphates and the amplified nucleic acid products are produced using PCR, rtPCR, LCR, Qbeta Replicase, SDA, CPR, TAS, NASBA, or multiple rounds of RNA transcription or some combination thereof. One or more second molecules, each including a functional group capable of being immobilized on a solid support, may also be incorporated into the amplified nucleic acid products. The functional group may also be used to bind the amplified nucleic acid products to a solid support, and separate incorporated mass labeled molecules from unincorporated mass labeled molecules. It may also be preferable to separate the amplified nucleic acid products from the unincorporated mass labeled molecules, for example, by binding the amplified nucleic acid products to a solid support or by hybridizing the amplified nucleic acid products to a polynucleotide bound to solid support. In the latter case, the bound polynucleotide may be an oligonucleotide, a polyribonucleotide, a plasmid, an M13, a cosmid, a P1 clone, a BAC or a YAC. A plurality of these polynucleotides may also be immobilized onto the solid support at spaced locations.

Also provided is a method for detecting the presence of a target nucleic acid molecule, said method comprising: obtaining a probe comprising a reactive group, a release group and a mass label; contacting the probe to a target nucleic acid molecule to produce probe:nucleic acid molecule complexes; mass modifying the probe:nucleic acid molecule complexes by attaching a nucleotide or oligonucleotide to the probe to produce mass modified mass labels; releasing the mass modified mass labels; and determining the mass of the mass-modified mass labels by mass spectrometry.

Another embodiment encompasses a method for detecting specific biomolecules in an enzyme-linked affinity assay comprising: obtaining a substrate; contacting a target molecule with an affinity ligand-enzyme conjugate to produce an affinity ligand-enzyme conjugate:target molecule complex with the substrate to produce a mass modified product; and determining the mass of the mass modified product by mass spectrometry.

As used herein, "affinity ligands" are groups, molecules, or moieties having an affinity for, or reacting with a particular target molecule, similar to the reactive groups employed with the mass label probes disclosed above. The affinity ligand may be a biomolecule capable of specific molecular recognition, such as a polypeptide or polynucleic acid. Preferred polypeptides include antibodies, enzymes, receptors, regulatory proteins, nucleic acid-binding proteins, hormones, and protein products of a display method, such as products of a phage display method or a bacterial display method.

The enzymes conjugated to these affinity ligands may be any enzyme that catalyze the conversion of the substrate to a product having a different mass, such as restriction endonucleases and proteases. Thus, the mass of the substrate has been modified in the production of the product by the enzyme. Affinity ligand-enzyme conjugates are molecules where the affinity ligand and enzyme have been attached by the formation of covalent or noncovalent interactions, including hydrogen bonds.

In some embodiments it may be preferable to employ a plurality of restriction endonucleases. In these cases, the various endonucleases may be conjugated to the affinity ligand to form several affinity ligand-enzyme conjugates which are then contacted with the target molecule. Similarly, it may be preferable to employ a plurality of affinity ligand-enzyme conjugates having different affinity ligands, enzymes, or both.

The substrate may be any molecule whose conversion to a mass-modified product is accomplished by the enzyme employed such as a polypeptide. For embodiments employing restriction endonucleases, it may therefore comprise a restriction site.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 2A:
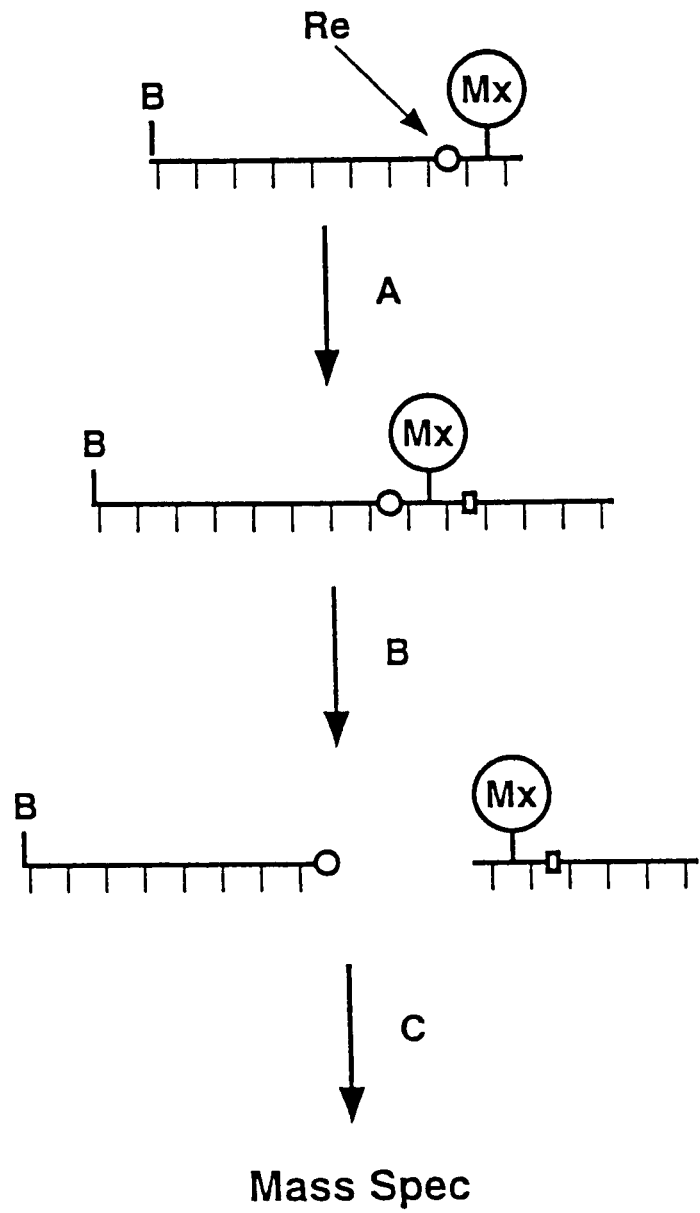
FIG. 2A and FIG. 2B show examples of a mass-labeled probe where the releasable group is contained within the reactive group and the released mass-label includes one or more monomers of the reactive group.

Shown in FIG. 2A is the use of the probe as an oligonucleotide primer that can be extended (Step A) by polymerase using nucleoside triphosphates, including deoxy and dideoxyribonucleotide or combinations thereof, or by ligase using oligonucleotides. Ligase may be used to attach oligonucleotides to the 5' as well as the 3' end. Nucleotides and oligonucleotides added as well as nucleotide monomers within the probe may optionally consist of modified nucleotides or non-natural, mimic nucleotides. Also shown is the optional use of a solid-phase binding group such as biotin (labeled B) that can be used to capture the extended mass-labeled primer prior to release of the mass-label product (Step B). Following release the mass-labeled product is analyzed by mass spectrometry (Step C). The non-reactive group component of the mass label is indicated by Mx, where the x signifies that this component may have a single molecular mass or it may represent a combination of 2 or more molecules of defined mass. The Mx component may be optionally contained fully within the reactive group and may be comprised of nucleotides or non-natural, mimic nucleotides. Determining the mass of the mass-label product provides the means for identifying the nucleotide composition and sequence of bases immediately adjacent to the probe.

Figure 2B:
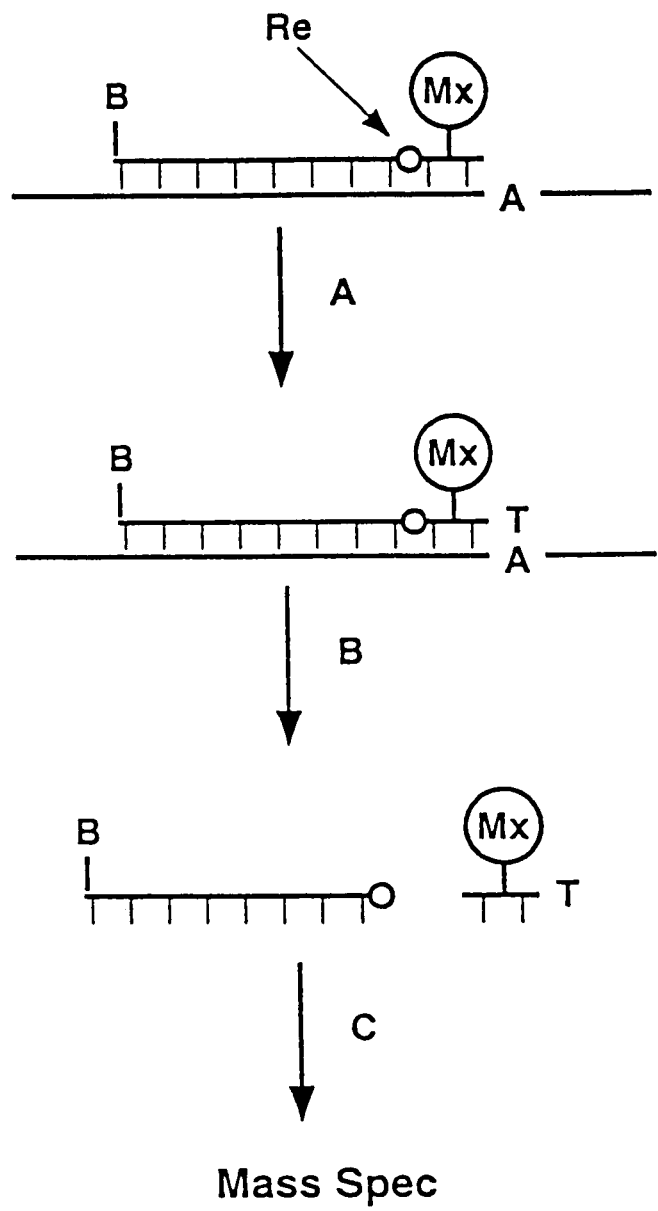

FIG. 2B illustrates the specific case where the mass-labeled probe functions as a primer to detect a single nucleotide polymorphism. In Step A, following hybridization to a template nucleic acid, a polymerase is used to add a single nucleotide chain terminator or mass-modified version thereof, selecting from the four possible bases. Following probe extension, the mass-labeled product is released (Step B) and analyzed by mass spectrometry (Step C). As in FIG. 2A, the probe optionally comprises a solid-phase binding group that may be used to bind and wash the probe prior to the releasing step. In this example a T chain terminator is added increasing the mass of the mass-label product by 298 Da, indicating the presence of an A within the template at the targeted position.

Figure 2C:
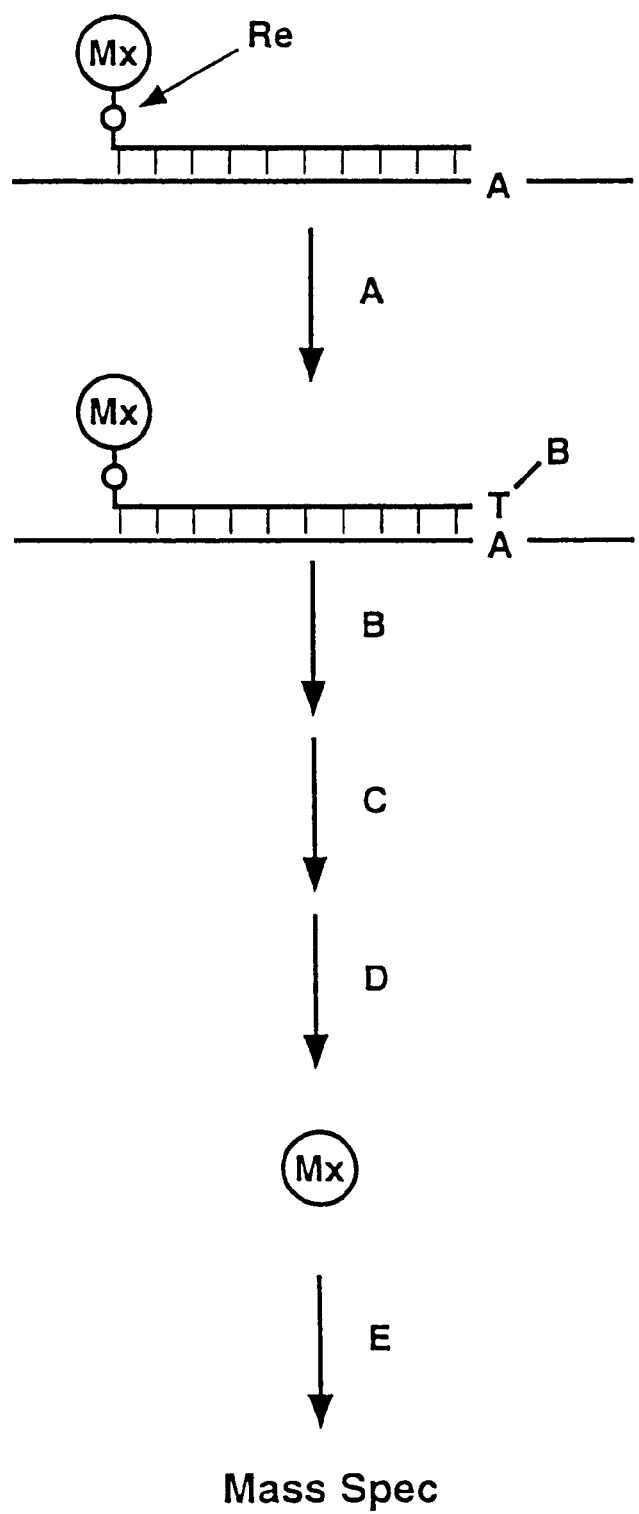

FIG. 2C illustrates a different embodiment for the use of a mass-labeled probe in the determination of single nucleotide polymorphisms. A mass-labeled probe is hybridized to a template and is extended by polymerase which incorporates a single chain-terminating nucleotide (Step A). The chain terminating nucleotide is modified to contain a solid-phase binding group such as biotin (labeled B) that is used to capture the extended mass-labeled primer prior to release of the mass-label product (Step D). In this particular illustration the probe is being used to identify whether or not an A nucleotide is present in the position adjacent to where the probe hybridizes. While the reaction may include all four chain terminating nucleotides, only the T chain terminator is modified to carry a solid-phase binding group. Therefore only if T incorporates, and A is present in the template, will the mass-labeled probe be modified and captured to the solid phase (Step B). Use of a washington step (Step C) prior to release (Step D) will remove any probes that have not incorporated T, removing their mass labels from the system. Only probes that were bound to the solid phase (Step B) will be detected in the mass spectrometer (Step E). The mass label is indicated by Mx, where the x signifies that this component may have a single molecular mass or it may represent a combination of 2 or more molecules of defined mass. A multiplex of many different probes is possible. The release group, Re, may be placed in the linker connecting the mass label to the probe, or at any position within the backbone of the probe. This methodology may be extended to cases where a combination of nucleotides and chain-terminating nucleotides are used, as well as oligonucleotides, where particular components are selected to contain a solid-phase binding group.

FIG. 3A and FIG. 3B illustrate a generalized scheme to produce a mixture of nucleic acid probes each with a unique single or combination of mass labels (FIG. 3A) and, in particular, a generalized scheme to incorporate mass-labeled nucleotides or oligonucleotides into a polynucleotide sequence using DNA polymerase (Step A) or ligase (Step B (FIG. 3B).

FIG. 3A illustrates a nucleic acid probe containing an invariant region and a variable region. The invariant region, which is optional, carries the same or near the same sequence for all probes within a family. The variable region contains all possible sequences or some subset thereof. As an example, if the variable region is 4 nucleotides in length 256 different probes can be made, if the variable region is 6 nucleotides in length 4096 different probe can be made. Associated with each probe sequence is a single or combination of mass labels. In either case, the mass labels chosen are unique to each sequence. In cases where combinations are used the mass labels (labeled M) may be single labels attached to different probes carrying the same sequence or multiple labels attached to a single probe, or some combination thereof.

FIG. 3B illustrates two embodiments where the mass-labeled family of probes may be used to screen a nucleic acid template. In addition to simple hybridization of the probe to template, the probes may be extended using either polymerase (Step A) or ligase (Step B). In either case nucleotides or oligonucleotides may be used that carry additional mass labels (labeled M*) identifying the sequence of the nucleic acid product being added, therefore enlarging the total template sequence determined per probe hybridization event. In a preferred embodiment the template is bound to the solid phase. Alternatively, the nucleotides or oligonucleotides added to the probe may contain a solid-phase binding group, enabling the isolation of the probe and attachment via solid-phase capture. As illustrated, X-Y represents Watson-Crick base pairing in the variable region of the probe, and N-M represents Watson-Crick base pairing in the added nucleotide or oligonucleotide sequence.

Figure 4B:
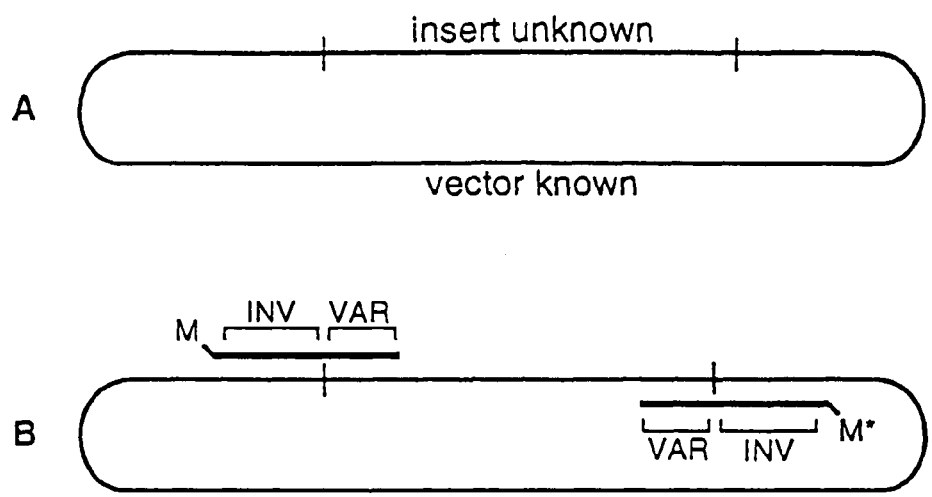
Figure 4C:
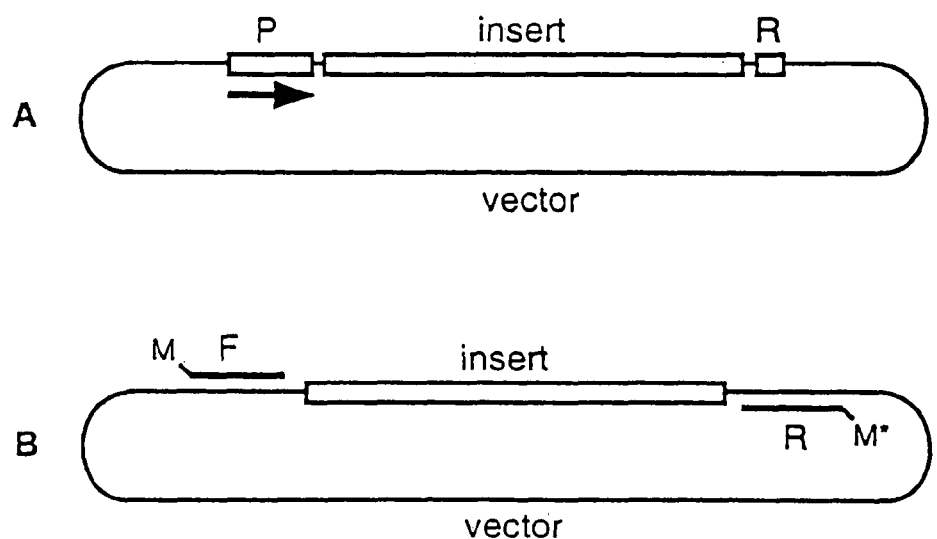

FIG. 4A, FIG. 4B, and FIG. 4C illustrate different combinatorial approaches to preparing mass labeled probes (FIG. 4A), using mass-labeled probes to screen a vector insert (FIG. 4B), and enzymatic methods, including transcription and PCR for the preparation of large mass-labeled polynucleotide probes (FIG. 4C).

FIG. 4A describes an example of how combinatorial labels may be used to label a complex set of oligonucleotides. The example describes a set of probes that have a variable region 4 nucleotides long comprising 256 possible sequence combinations. Variable regions shorter or longer are also possible. In the table and example list (C), it is shown how a set of 16 different mass labels may be used to create a mass label signature that is unique for all 256 combinations. Two different approaches may be used to creating the labeled probes, the first (A) being the use of 16 different phosphoramidites each containing a different mass label that are used according to the base and position of synthesis. This approach leads to a set of molecules each with 4 labels on them and is performed as a single reaction. Variants are possible where the synthesis is split into multiple pots and standard phosphoramidite are used in some positions to reduce the number of labels per molecule. The second combinatorial approach (B) is to presynthesize the 256 combinations in 16 different reactions prior to adding the mass labels, each of which is used to define one of the 4 bases in one of the 4 positions. Following oligonucleotide synthesis, each of the 16 different reactions is coupled to one of 16 different mass labels. The end product is that each probe in the pool contains only one specific mass label. The second approach offers greater flexibility for the placement and type of the mass label since it is not coupled directly to the oligonucleotide synthesis. Other labeling schemes can be envisioned when using the post oligonucleotide synthesis method especially when the oligonucleotide set is synthesized in a larger number of reactions, with ultimate flexibility if the 256 combinations are all synthesized separately. With either approach the synthesis may optionally include an invariant synthetic region as shown in FIG. 4A. The variable region may also include one or more discontinuous bases within the invariant region. These probes may be applied to screening for polymorphisms in diagnostic and genomic applications including single nucleotide polymorphisms where the variable region is only one nucleotide long.

FIG. 4B describes how the combinatorially labeled probes may be used to screen polymorphic sequences that are adjacent to the insert sequences within cloning vectors (A), including cDNA and genomic clones. The use of an invariant sequence within the probes allows the probes to be anchored at the junction between the known vector sequence and the unknown insert sequence with the invariant region of the probe hybridizing to the known sequence and the variable region selecting its complement in the unknown region (B). Methods utilizing these probes include simple hybridization to one or both of the clone insert ends, nucleotide or oligonucleotide extensions as described in FIG. 3B, and use of the probes for primer extension to make a single copy of the insert or for purposes of amplification. For a given insert sequence, use of forward and reverse probes in a PCR amplification would result in the selection of only one forward and one reverse probe out of the set to create the amplification product. This technique can be combined with a number of different selective mass label release methodologies to identify sequences.

FIG. 4C illustrates two different methods for creating mass-labeled polynucleotide probes by either transcription (A) or PCR amplification (B). Use of RNA transcription to synthesize mass-probes is limited to sequence regions that are downstream from a promoter sequence (labeled P). Typical synthetic procedures would utilize RNA polymerase and ribonucleoside triphosphates, including mass-labeled versions that may carry one or more mass labels. Shown in (A) is a transcription vector carrying a transcription promoter and a clone insert sequence to be transcribed downstream. The vector also carries one or more restriction sites (labeled R) that may optionally be cut to control the length of transcripts. Virtually any amplification technique may be used to create mass-labeled probes including PCR, as is shown in (B). PCR amplification requires the use of two opposing primers to enable exponential amplification of the sequence located between them. One or more mass labels may be placed on one or both of the primers or optionally incorporated through the use of mass-labeled nucleoside triphosphates.

Figure 5A:
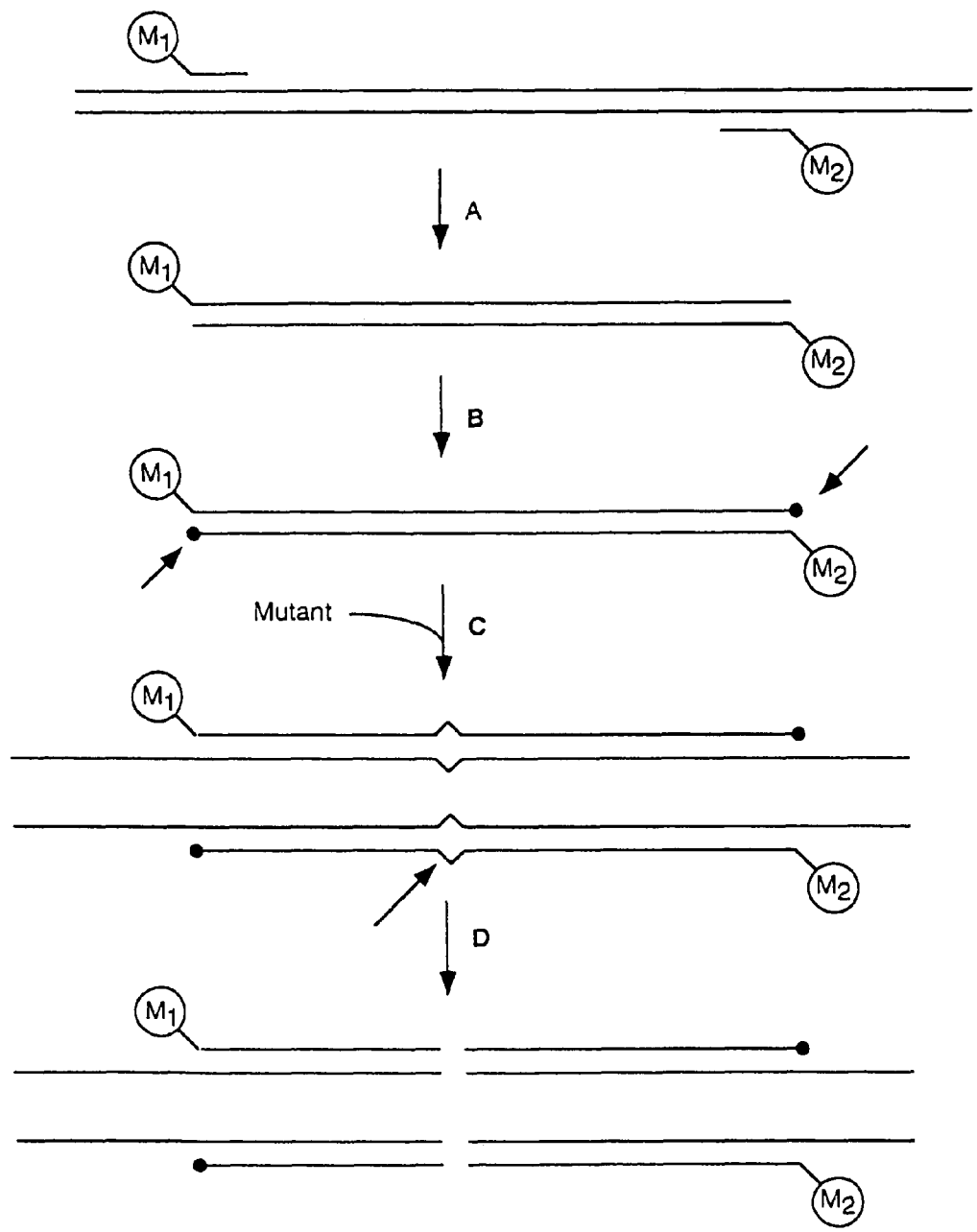
Figure 5B:
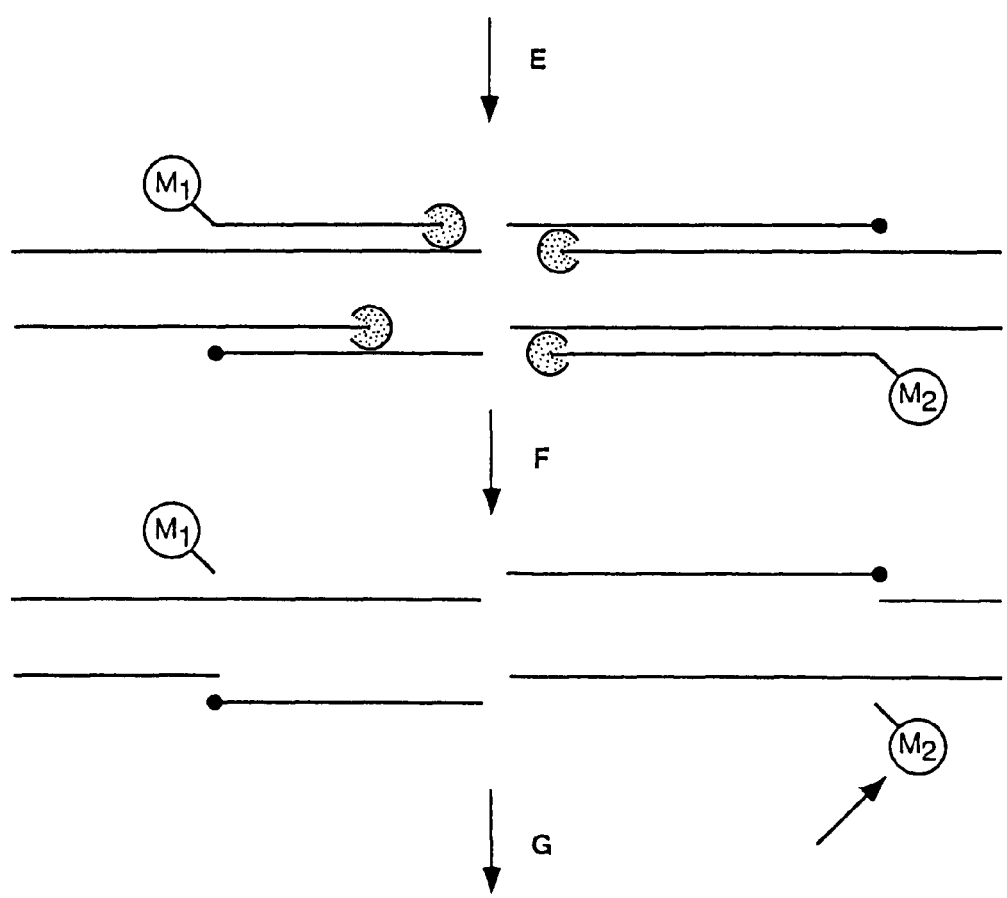

FIG. 5A and FIG. 5B illustrate schemes for detecting mutations using mismatch specific techniques with enzymatically synthesized mass-labeled probes. Generally the methodology requires the cross hybridization of normal and mutant or polymorphic nucleic acid to form a double-stranded product containing a mismatch; enzymatic or chemical cleavage at the site of the mismatch; and cleavage induced digestion of the probe to release one or more mass labels. In the example shown in FIG. 5A and continued in FIG. 5B, a double-stranded mass-labeled nucleic acid probe is synthesized using PCR (A), the 3' ends of the product are blocked from exonuclease digestion (B), the PCR probe is hybridized to mutation carrying DNA (C) which leads to the formation of a base-pair mismatch, the mismatches are cleaved (D), the cleaved products are digested with a 3' to 5' exonuclease (E), the mass labels are released (F) and analyzed by mass spectrometry (G). Examples of 3' exonuclease blocking groups include nucleotide mimics incorporated near the 3' end, such as nucleotides' contains boranophosphates or phosphorothioates, or the use of 3' overhangs created during nested-set PCR or by template independent extension by terminal transferase in combination with a double-strand-specific 3' to 5' exonuclease, such as exonuclease III, that does not recognize or digest 3' overhangs. Examples of mismatch specific cleavage agents for use in (D) include the chemical $OsO_4$, $KMnO_4$, and $HONH_2$, and enzymes, such as mutHLS, T4 endonuclease VII, mutY DNA glycosylase, thymine mismatch DNA glycosylase, or endonuclease V. Methods using RNA or RNA/DNA hybrids are also possible.

Figure 6A:
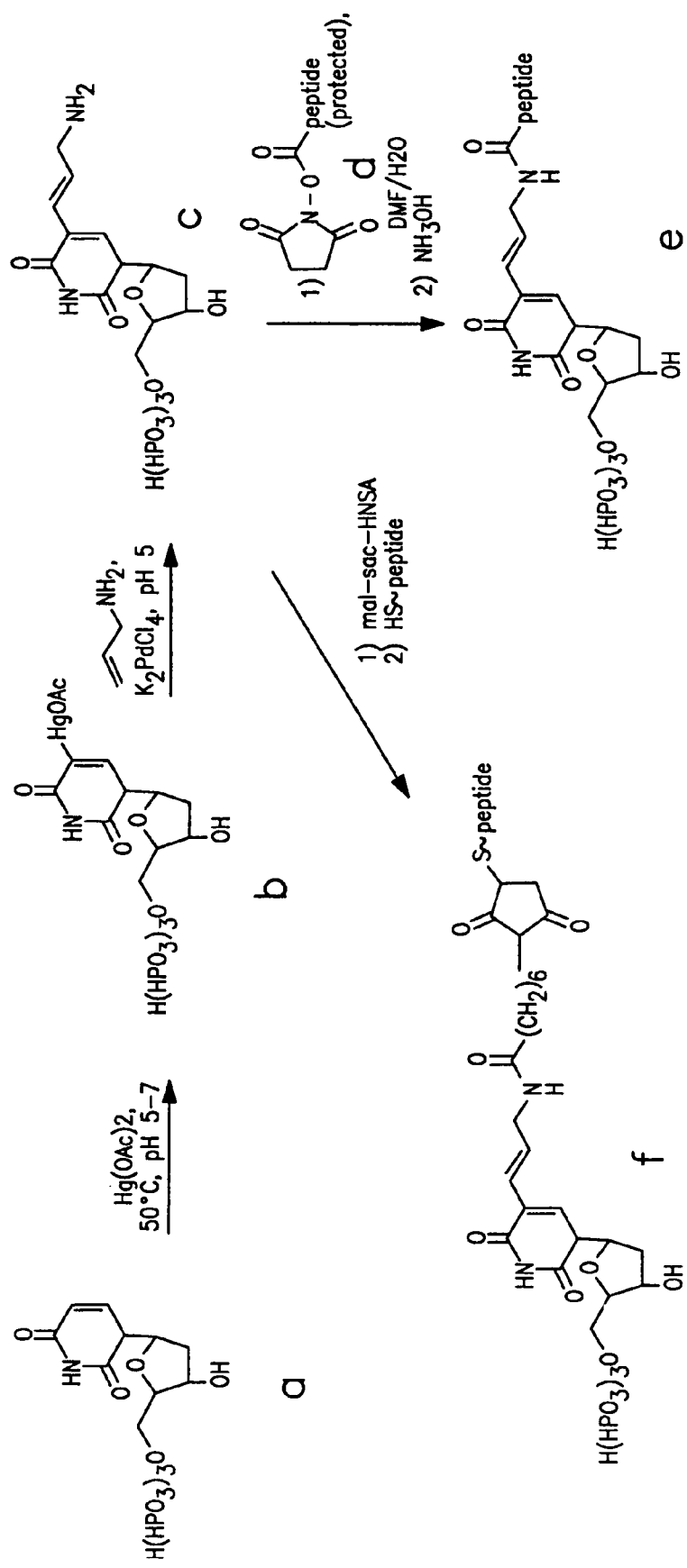

FIG. 6A, FIG. 6B and FIG. 6C illustrate schemes for the synthesis of peptide-linked nucleoside triphosphates (FIG. 6A), an oligonucleotide with a linker molecule that contains a release group, a disulfide, and a terminal amino-modification for coupling a peptide of some other mass label component to the end (FIG. 6B), and a scheme for the synthesis of a peptide-linked nucleoside phosphoramidite (FIG. 6C).

FIG. 7A and FIG. 7B. show the mass spectra of the unconjugated oligonucleotide (FIG. 7A) and the oligonucleotide-peptide conjugate (FIG. 7B) of Example 1D. The spectrum of FIG. 7A contains in addition to the signal for the desired oligonucleotide at m/z 7052, signals showing the presence of two significant synthesis failure that correspond to one base and three bases less, and also signals of doubly charged ions for each of these. The spectrum of FIG. 7B shows that the purified conjugate is of similar purity to the starting oligonucleotide.

Figure 8A:
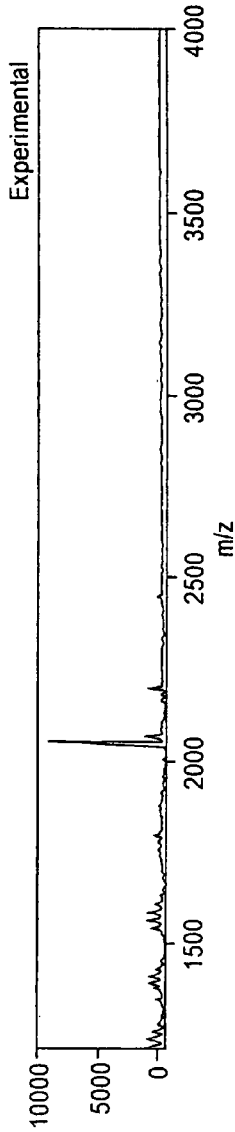
Figure 8B:
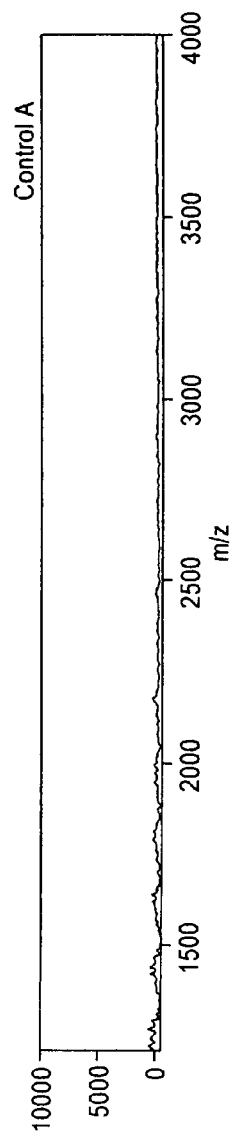
Figure 8C:
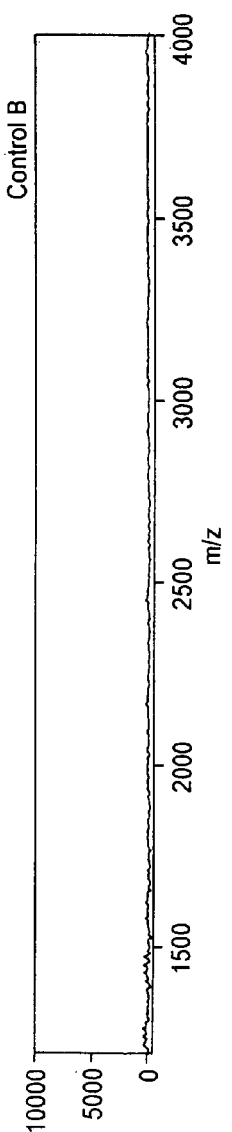
Figure 8D:
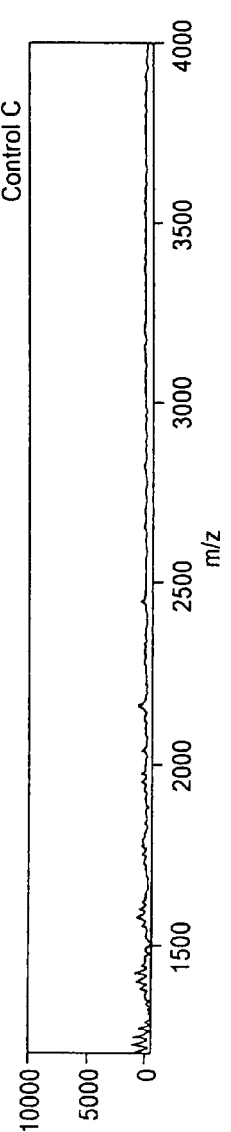

FIG. 8A, FIG. 8B, FIG. 8C, and FIG. 8D show the mass spectra of a hybridized, mass-labeled probe and target in a buffer after Exonuclease III digestion (FIG. 8A), a hybridized, mass-labeled probe and target incubated with no Exonuclease III (FIG. 8B), of a mass-labeled probe in buffer incubated with Exonuclease III (FIG. 8C), of a mass-labeled probe incubated with Exonuclease III buffer in the presence of a non-complementary 36-mer target (FIG. 8D). As shown in these FIGS., the mass label is released only in the presence of the exonuclease and a complementary target strand.

Figure 9A:
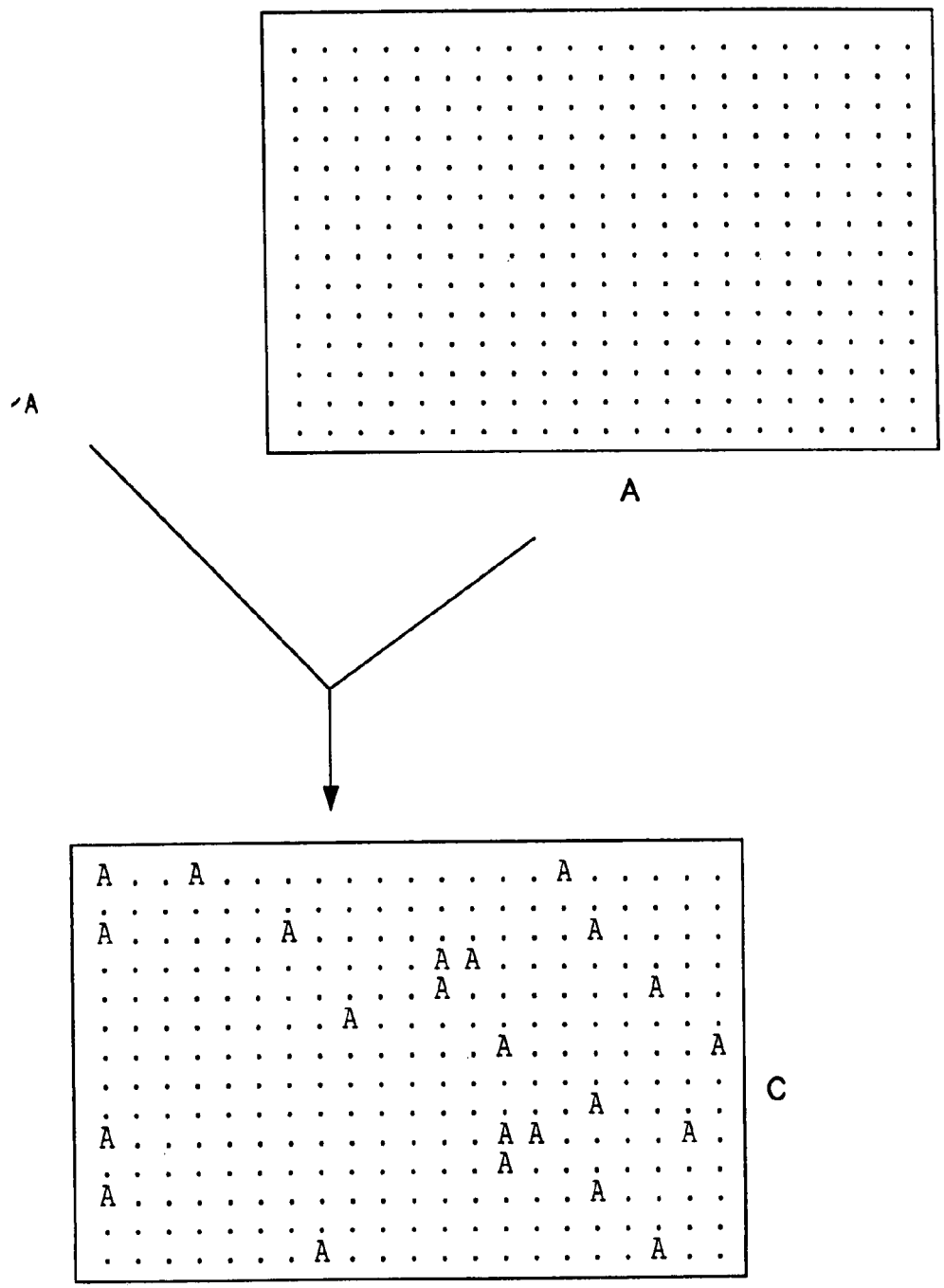
Figure 9B:
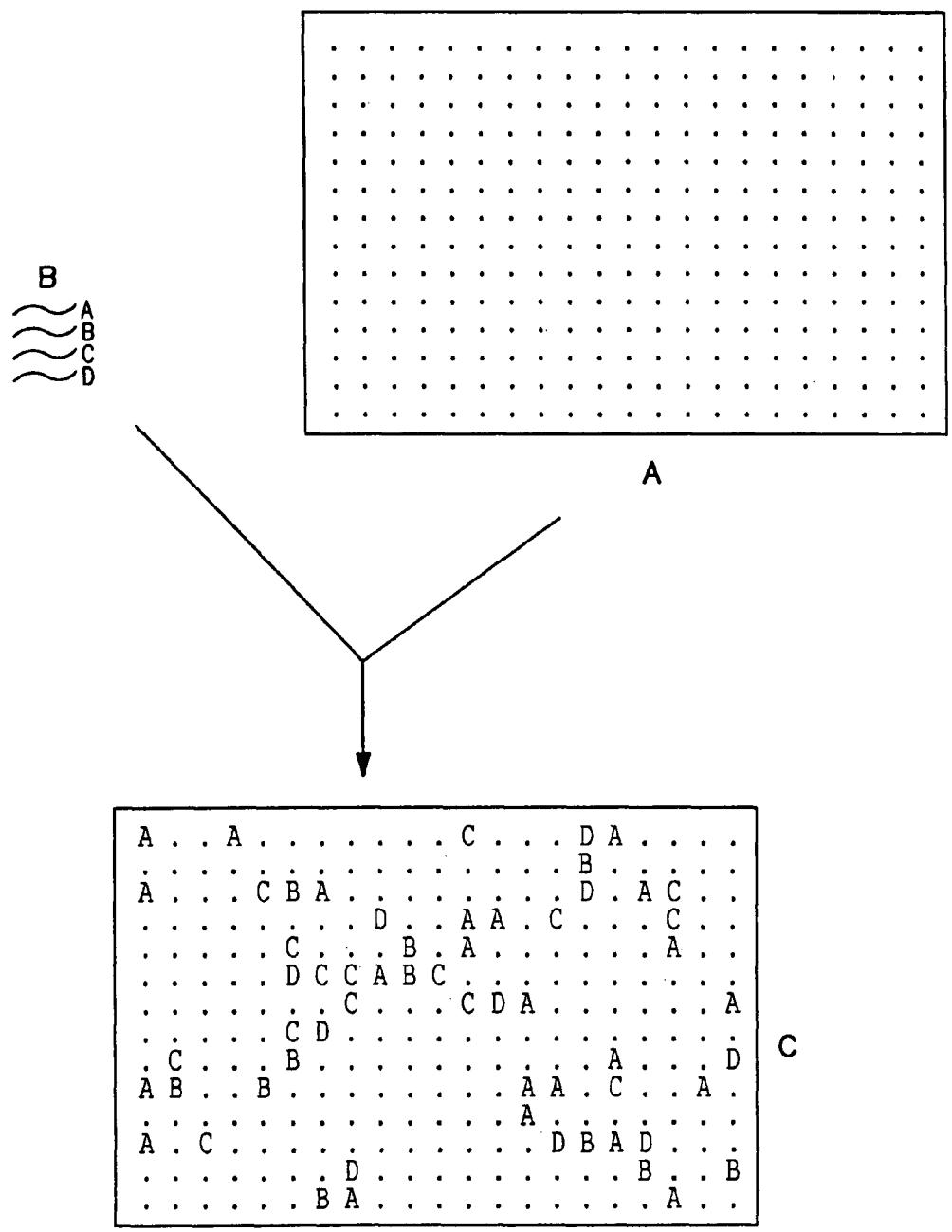
Figure 9C:
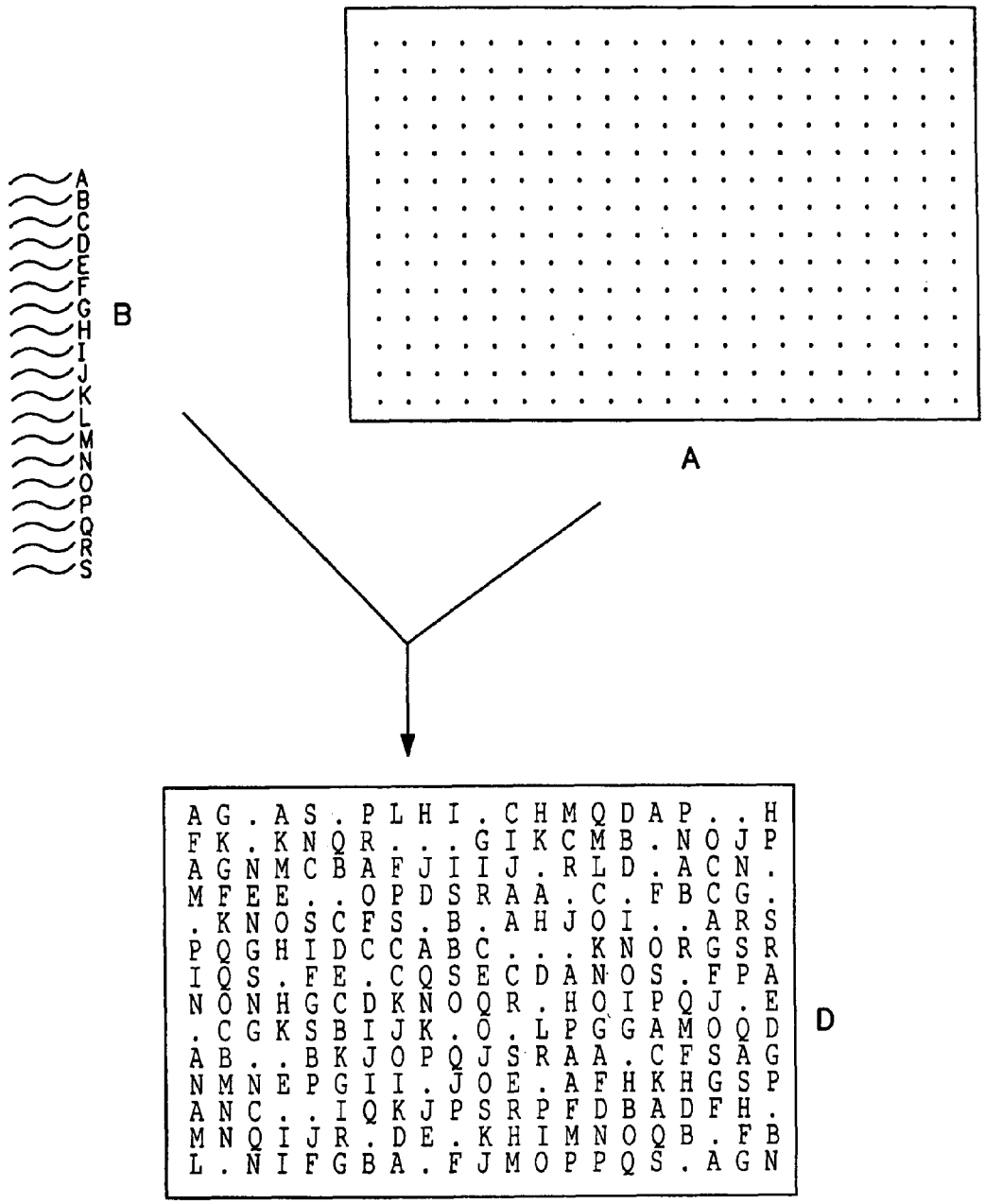

FIG. 9A, FIG. 9B and FIG. 9C compare solid support grid assays using a radioactively-labeled probe (FIG. 9A), fluorescently-labeled probes (FIG. 9B) and mass-labeled probes (FIG. 9C).

FIG. 9A describes the classical approach to probing nucleic acid samples arrayed on a spaced grid. Commonly nucleic acid samples representing MRNA isolates, CDNA clones, genomic clones are arrayed on a nylon membrane or filter grid (A). Following a photocrosslinking process to covalently attach the samples to the membrane, a radioactive probe (B) (labeled A), in solution, is added and incubated with the grid (C). The probe hybridizes to positions in the grid where the nucleic acid samples contain a length of sequence complementary to the probe. After wash step the grid is exposed to X-ray film and the hybridization positions are identified (indicated by the A positions in the grid) (D).

FIG. 9B illustrates the extension of the process in FIG. 9A, to the use of fluorescently-labeled probes (B). Because of the different emission spectra of different fluorescent labels it is possible to multiplex a small number, e.g. 4 (labeled A, B, C, D), of differently labeled fluorescent probes and cross hybridize them to the grid (C). In the case where fluorescence is used, the grid may be composed on a glass plate, rather than a filter or membrane, to enable fluorescence scanning techniques.

FIG. 9C illustrates the use of mass-labeled probes (B) (labeled A-S) foi hybridization against a gridded array of nucleic acid samples. Either single or combinatorial labeling techniques may be used to create a few to millions of different probes, all simultaneously hybridized against the array. The grid (D), which may be a nylon membrane or some other conductive material may be scanned directly in the mass spectrometer following hybridization, wash, mass-label release, and matrix addition steps (C). Scanning each position of the grid in the mass spectrometer reveals one of the many possible mass-label signatures associated with each unique probe. Typical examples of assays that would use this technology include the use of known gene-specific probes against gridded CDNA clones, MRNA, CDNA or amplified cDNA pools. Genomic probes, both known or unknown against gridded genomic clones. mRNA, cDNA, amplified cDNA against known gridded genes.

Figure 10B:
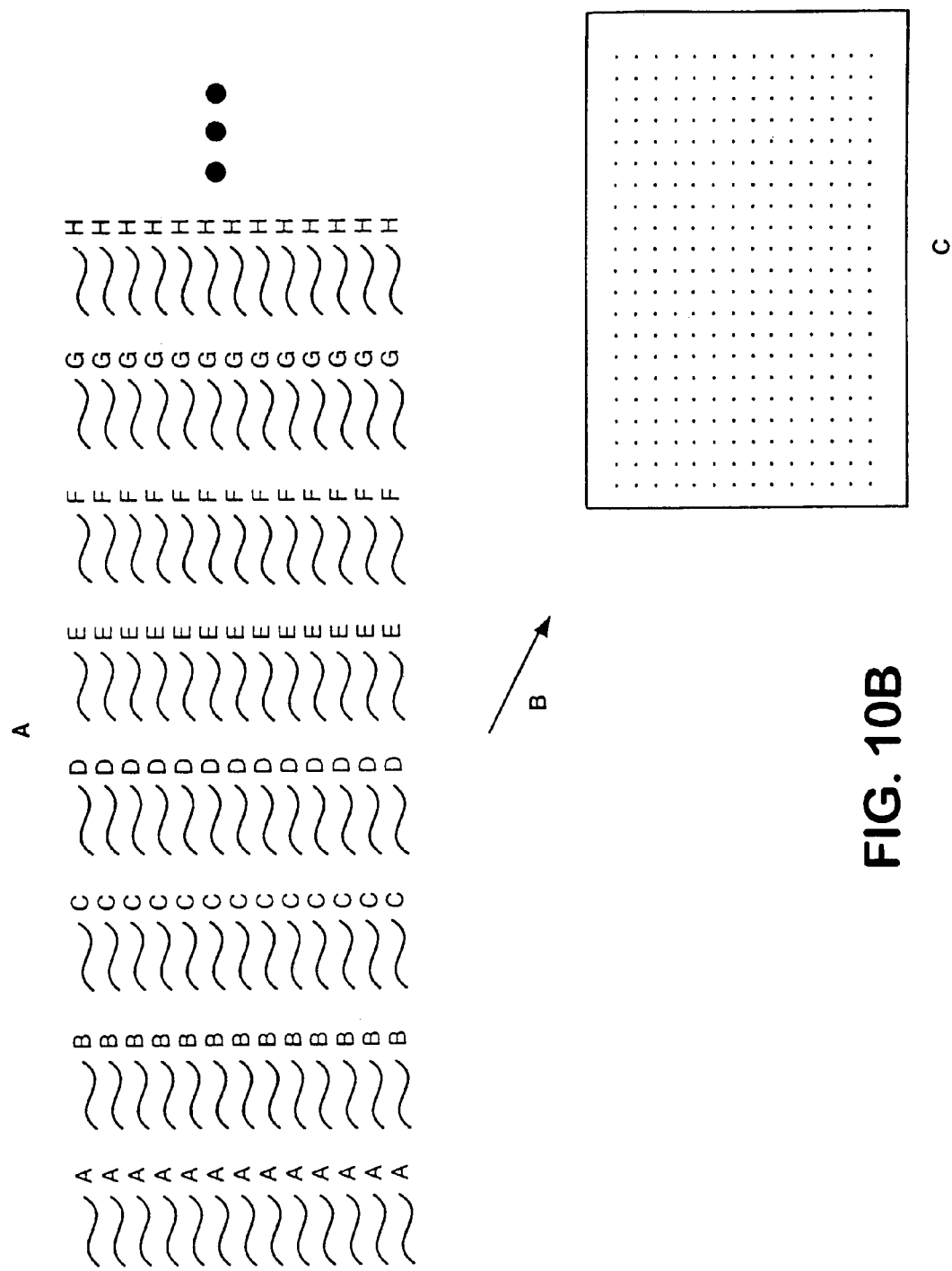

FIG. 10A and FIG. 10B compare library expression analysis using a fluorescence based system (FIG. 10A) and a mass-labeled system (FIG. 10B). Fluorescence labeling of pairs of cDNA pools derived from mRNA is used to cross compare the gene expression patterns between two different biological samples.

In FIG. 10A, one cDNA pool is labeled with fluorescent tag A while the other pool is labeled with fluorescent tag B (A). These pools have their concentrations normalized and are mixed (B). The mixture of the pools is then hybridized against a gridded, reference array of known genes, typically arrayed as cDNA clones. Following hybridization the array is scanning fluorimetrically and the ratio of the two tags is measured for each location. For a given location if tag A is twice the intensity of tag B, it is determined that the gene, which is gridded to that location, is expressed as mRNA at twice the concentration for sample A than for sample B.

FIG. 10B, expands the concept of competitively hybridizing cDNA pools beyond the 2 pool level. The use of releasable mass labels provide the means for the preparation of many more pools (A) (labeled A-H), cross-competitive hybridization (B), and detection (C) of many more pools of expressed message all simultaneously.

Figure 11:
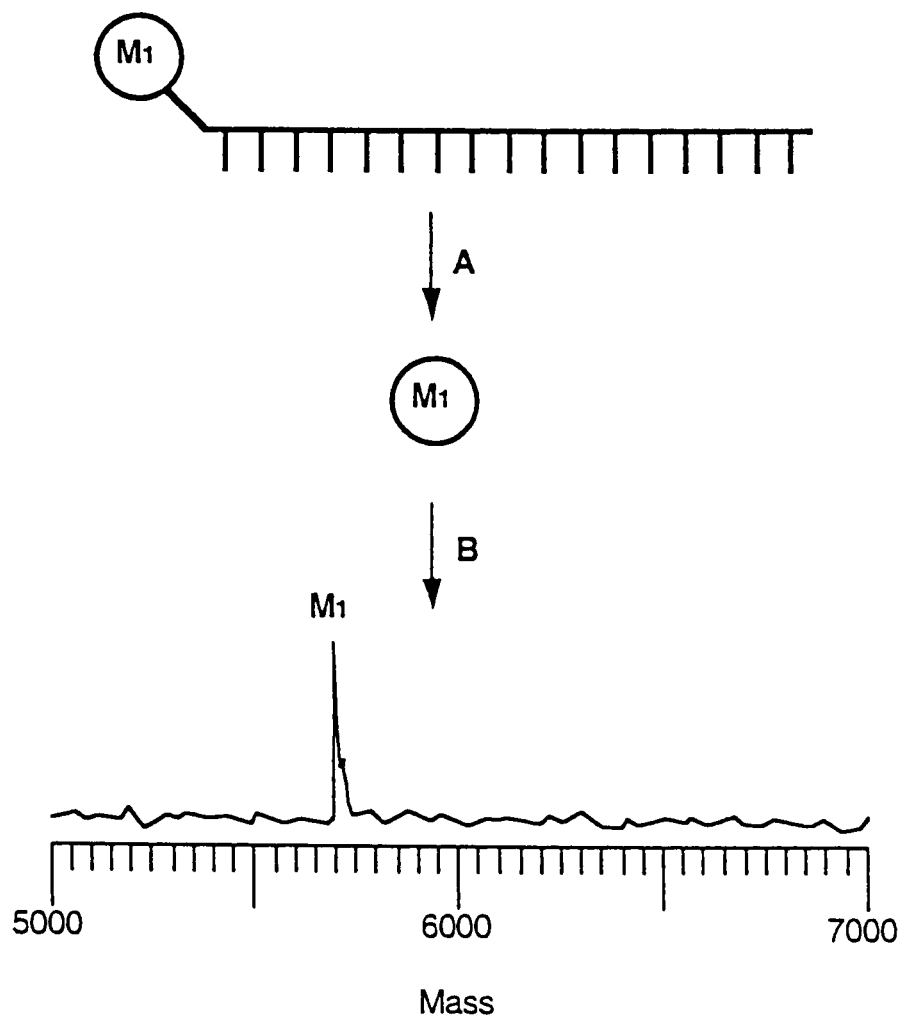

FIG. 11 illustrates the basic principal of release of a mass label from a nucleic acid probe for analysis by mass spectrometry. The mass label, M1, is released either chemically or enzymatically (A) and detected by mass spectrometry (B).

Figure 12:
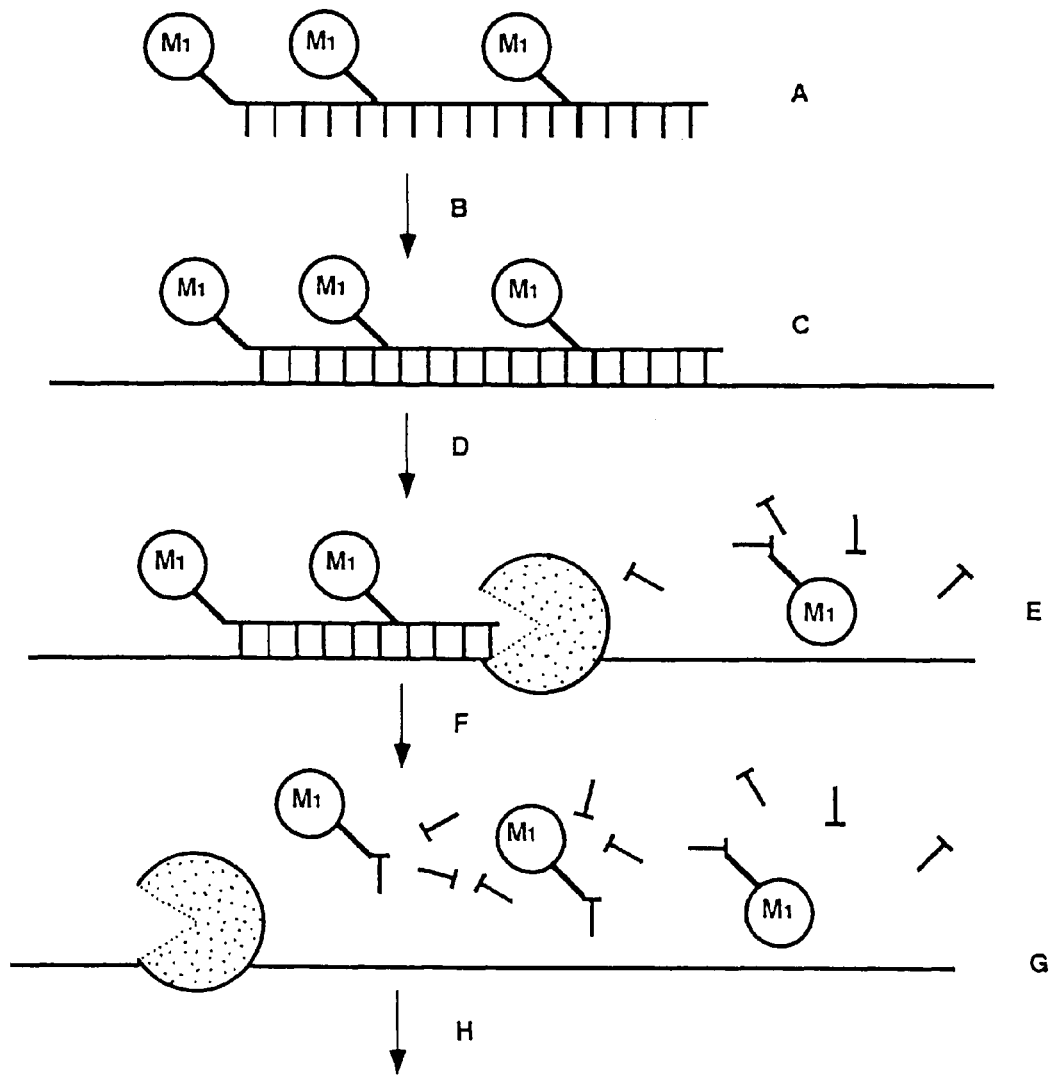

FIG. 12 illustrates selective release of mass labels following hybridization of a nucleic acid probe to a target DNA sequence. Mass-labeled nucleic acid probes (A), that may contain more than one label (as shown), and having different masses of mass label (not shown), are hybridized to a complementary nucleic acid target (B) to form a double-stranded complex (C). This complex is recognized by a double-strand-specific exonuclease and the probe is digested (D), releasing mass labels from the probe (E). For processive exonucleases the process will continue (F) until the entire probe is digested (G). The digestion is then analyzed by mass spectrometry and the released mass labels are detected (H). Mass labels comprise at least one nucleotide when digested by an exonuclease.

Figure 13:
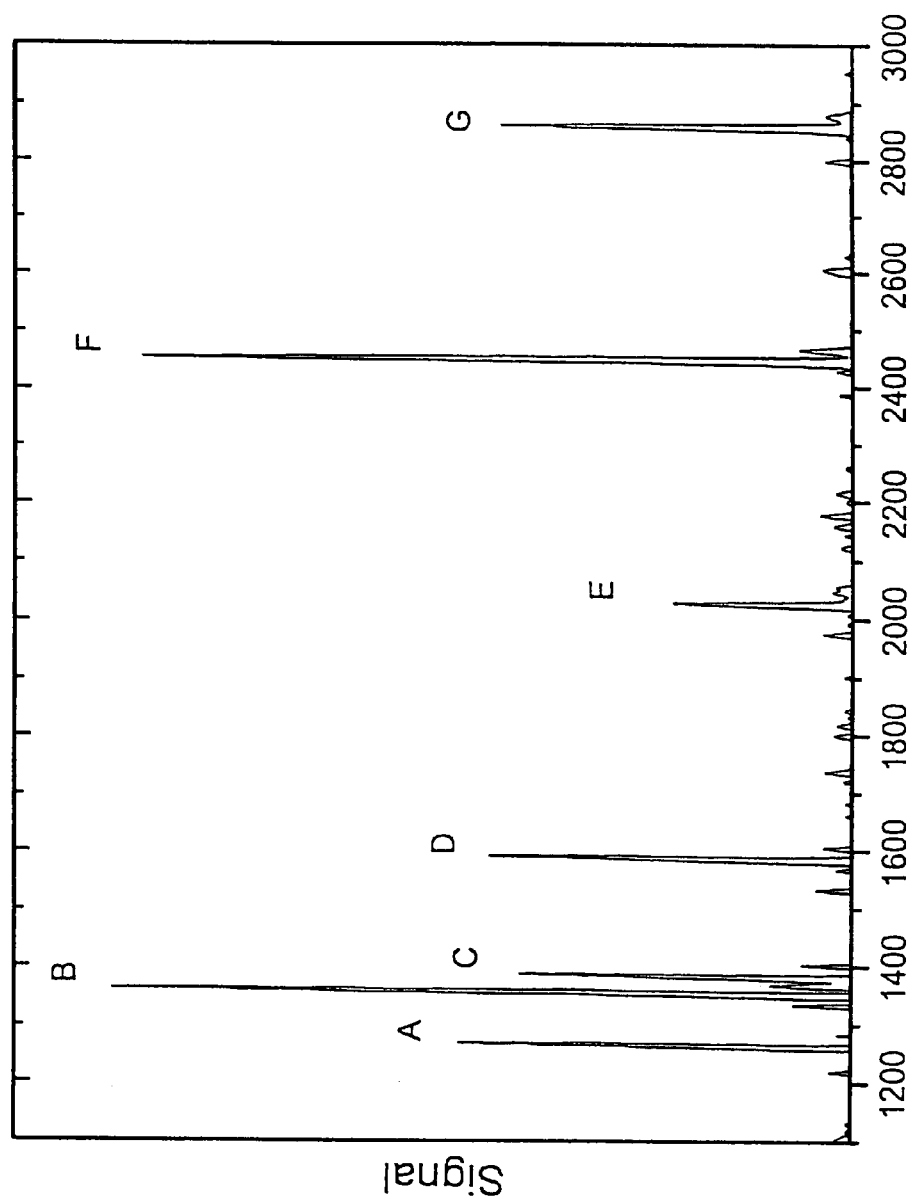

FIG. 13 illustrates the separation of peptides A-G by MALDI mass spectrometry where A is angiotensin I, B is substance P, C is CGYGPKKKRKVGG (SEQ ID NO:2), D is TCVEWLRRYLKN (SEQ ID NO:7), E is CSRARKQAASIKVSADR (SEQ ID NO:8), F is oxidized A-chain insulin and G is melittin.

Figure 14:
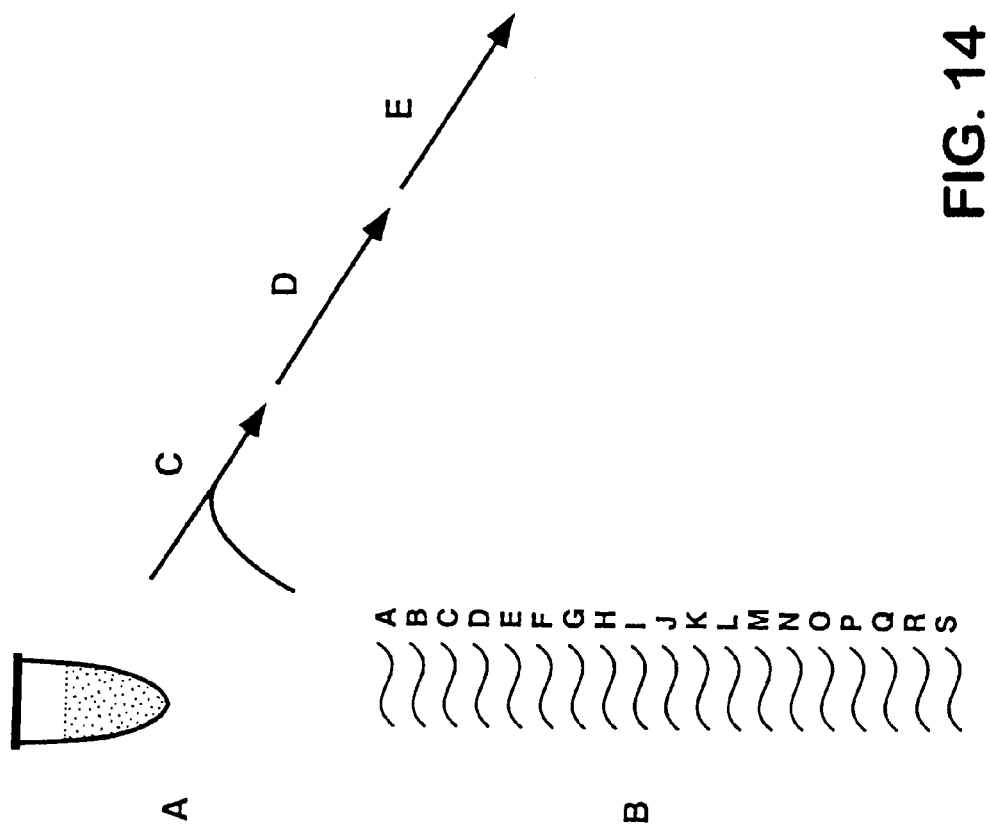

FIG. 14 illustrates a schematic representation of a process by which a series of gene-specific mass-labeled nucleic acid probes are used to detect and quantify the amount of different targeted mRNAs within a given sample. A starting pool of nucleic acid (A) that is the mRNA, cDNA copy of the mRNA, or some amplified multiplex of nucleic acid derived from the mRNA, is mixed with a set of message-specific mass-labeled nucleic acid probes (B) (probes with different mass labels labeled A-S). The mixture is allowed to hybridize (C) wherein probes that find complementary messages in the pool form double-stranded complexes, wherein the concentrations of the gene-specific double-stranded complexes is proportional to the levels of mRNA present in the starting material. Following the formation of double-stranded complexes, the mixture is treated with a double-strand-specific nuclease, e.g. exonuclease III treatment, selectively releasing mass labels from probes that had hybridized (D). The released mass labels (labeled A-s) are then analyzed by mass spectrometry (E), wherein the quantity of each mass label detected is proportional to the levels of mRNA present in the starting material. The selective release step may optionally use double-stranded chemical release probes as well as solid phase capture methods to differentiate double-stranded probes from unhybridized single-stranded probes.

Figure 15:
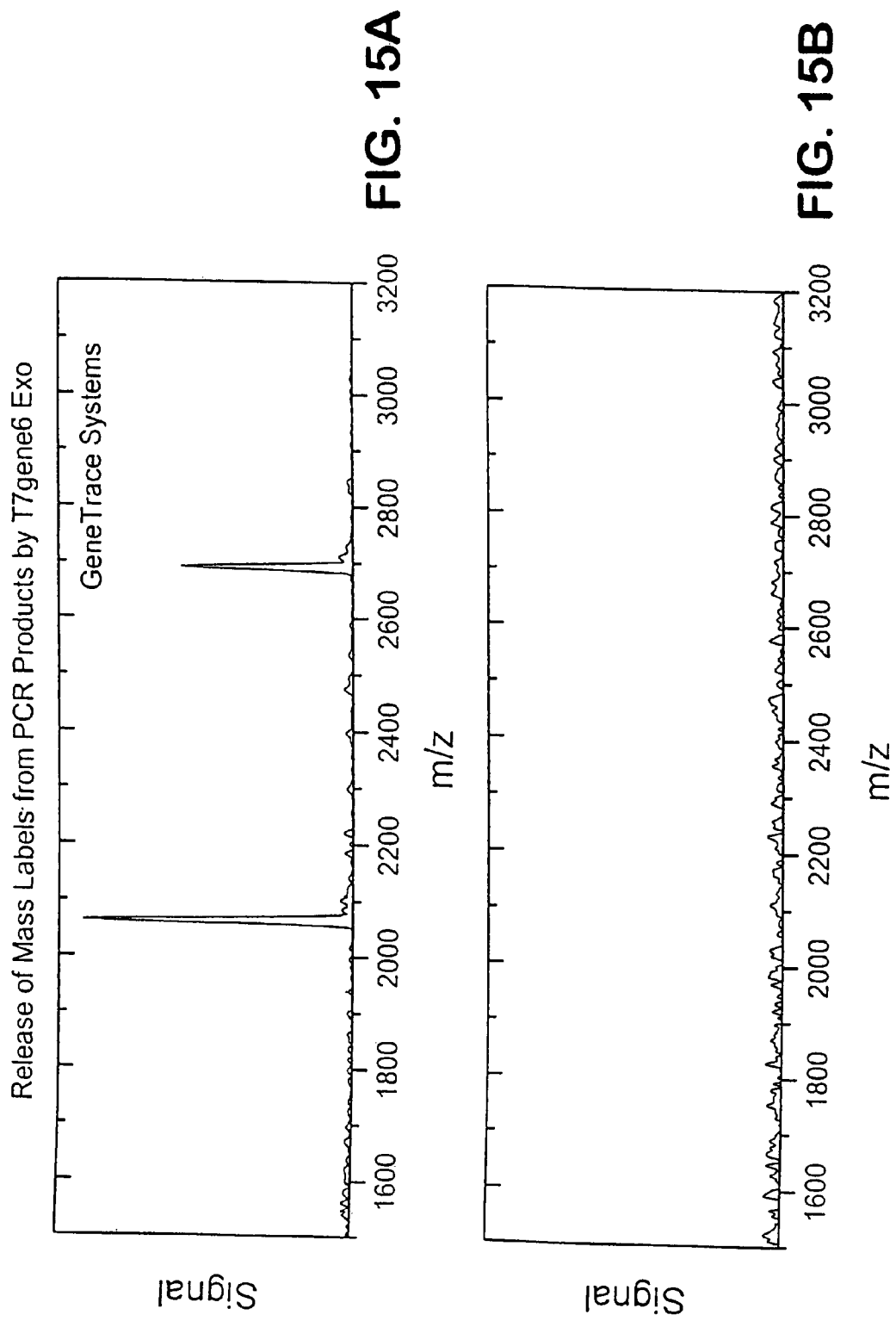

FIG. 15A and FIG. 15B shows two mass spectra. For FIG. 15A, an rtPCR™ reaction was performed using a pair of mass-labeled primers targeted at the mRNA for ribosomal protein L7. Following the PCR™, the reaction mix was treated with the double-strand-specific exonuclease T7 gene 6 exonuclease. Only when a double-stranded PCR™ product is formed does the exonuclease digest the product and release the two mass labels, as indicated by two peaks in the spectrum. In FIG. 15B, a control was performed where a single-stranded, mass-labeled primer was incubated with T7 gene 7 exonuclease. No digestion occurred.

Figure 16:
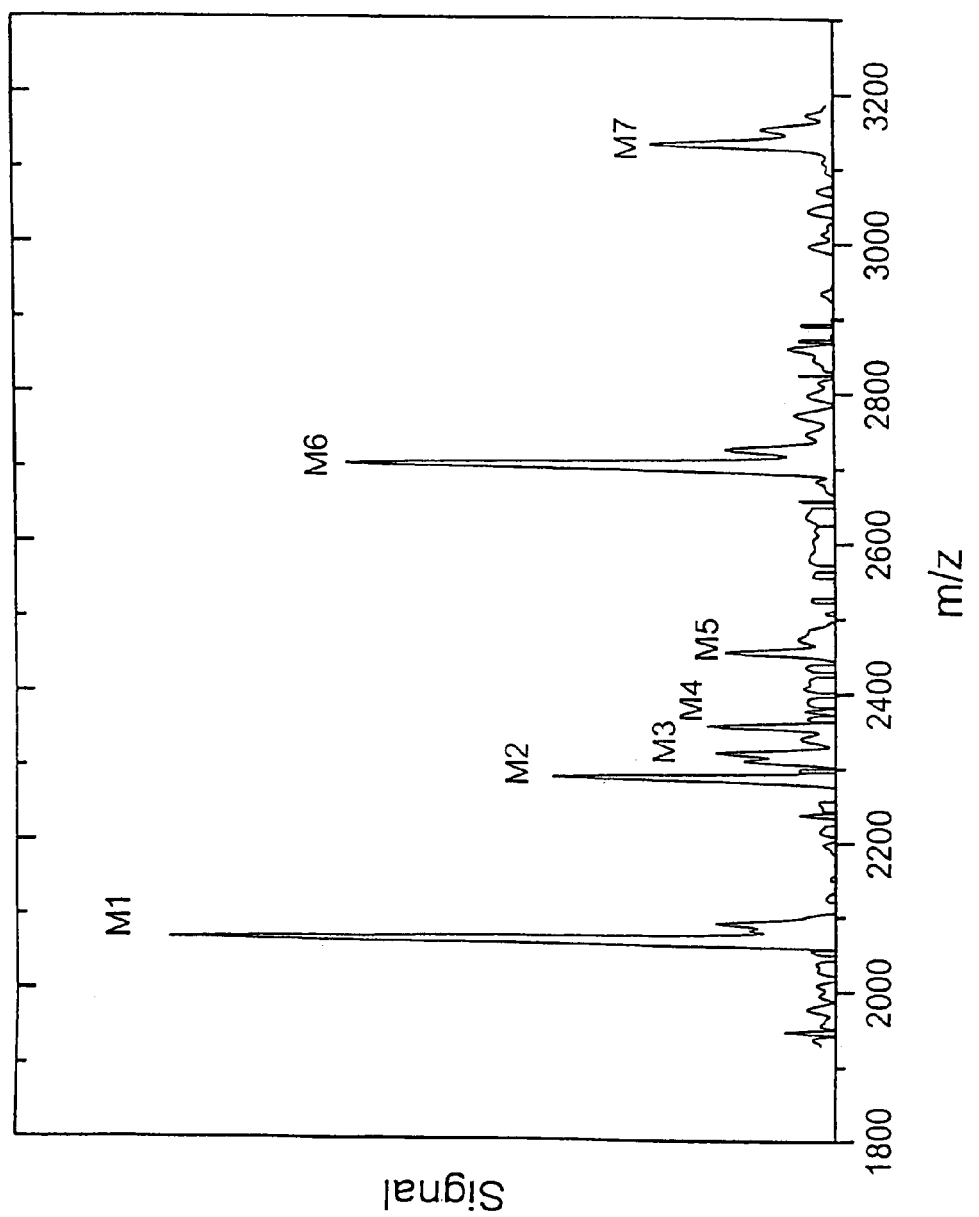

FIG. 16 illustrates the release of a series of seven different mass-labeled probes which were hybridized to seven different cDNA plasmids and then treated with exonuclease III. An aliquot of the double-strand-specific digestion was taken and analyzed by mass spectrometry. The mass spectrum is shown with the peaks corresponding to each mass label signal labeled A-G.

FIG. 17A and FIG. 17B shows two mass spectra from a SNP analysis using a mass-labeled primer and a biotinylated dideoxynucleoside triphosphate. In FIG. 17A a complementary match is made between the polymorphic base on the template and the biotinylated dideoxynucleoside triphosphate. The mass-labeled primer has been extended and therefore biotinylated, which allows it to be captured to a streptavidin-coated surface, washed and subsequently cleaved from the surface. FIG. 17B shows a mass spectrum from a reaction in which the base at the polymorphic site is not a complementary match to the biotinylated dideoxynucleoside triphosphate present in the reaction. No extension of the primer occurred as evidenced by the absence of a mass spectrometric signal for the primer mass label. The unextended primer is not captured on the streptavidin-coated surface and is removed in the subsequent washes.

Figure 18:
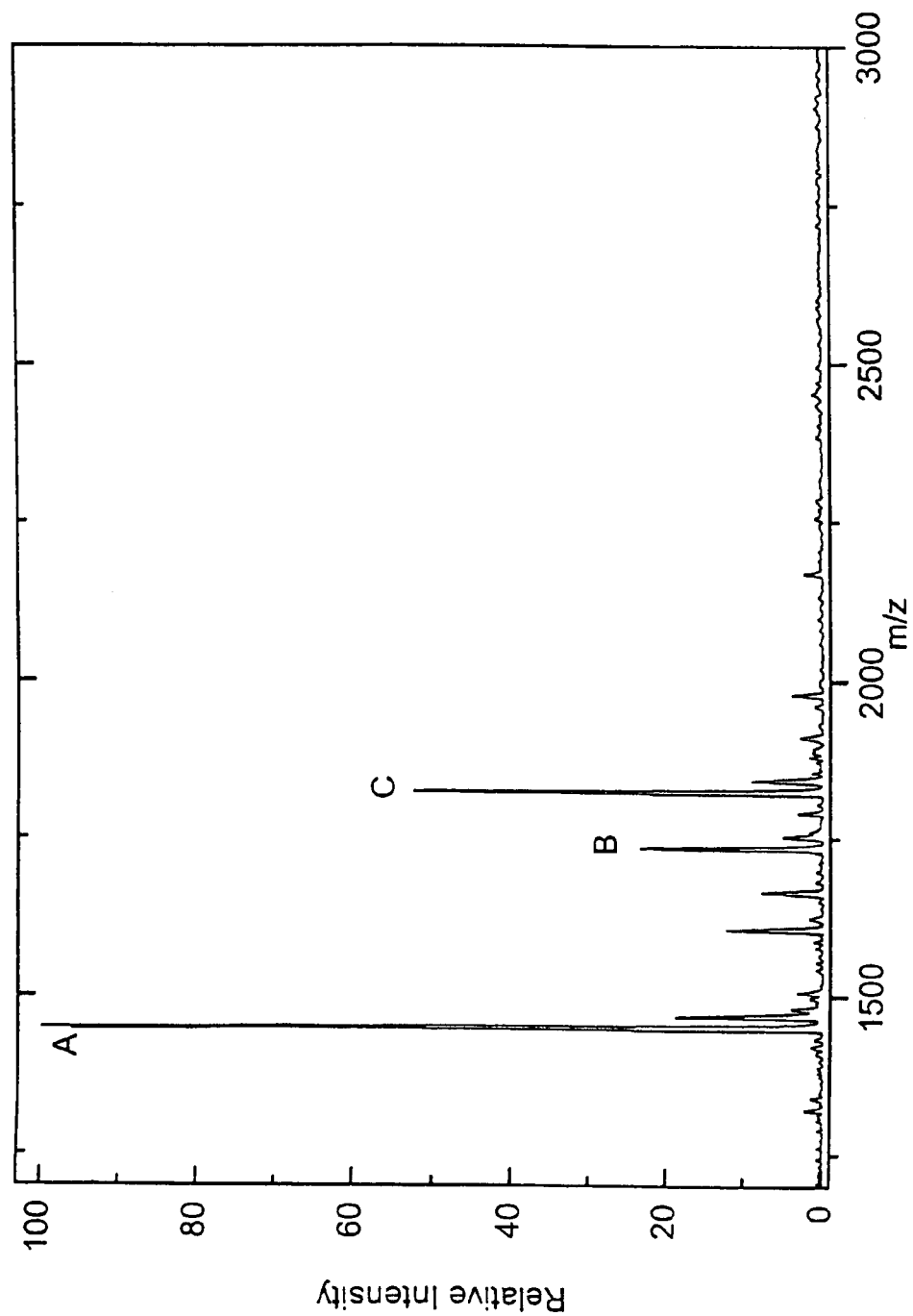

FIG. 18 shows a mass spectrum from a multiplex SNP analysis in which three differently mass-labeled primers for three different polymorphic sites are all simultaneously extended with a biotinylated dideoxynucleoside triphosphate. The three extended primers are all capable of being captured on a streptavidin-coated surface, washed to remove unextended primers and then cleaved from the surface.

Figure 19A:
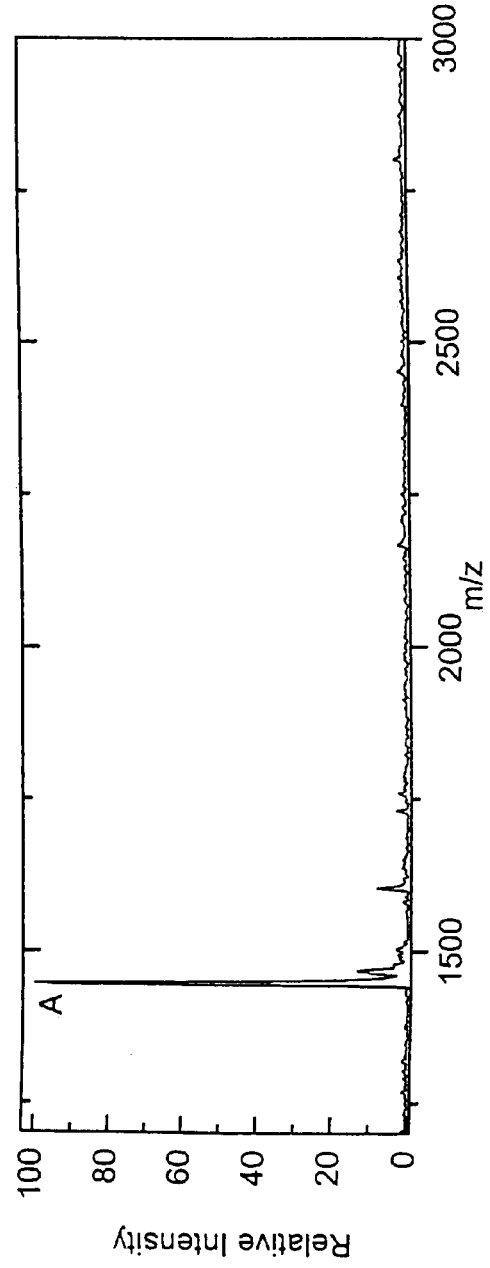
Figure 19B:
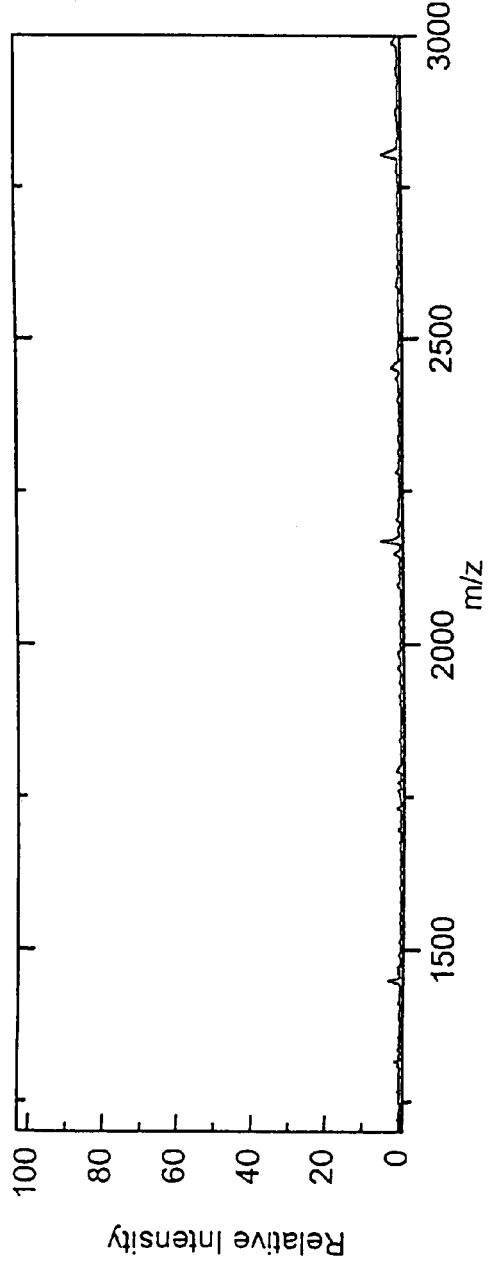

FIG. 19A and FIG. 19B shows two mass spectra from a SNP analysis in which the extension is carried out a few bases past the polymorphic site and for which biotin is incorporated through a biotinylated deoxynucleoside triphosphate. The mixture of triphosphates in the reactions consists of deoxy-ATP, biotinylated-deoxy-CTP, and dideoxy-TTP.

In FIG. 19A the spectrum is from a reaction in which the polymorphic site on the template, located one base past the 3'-end of the primer, is a T. Since the polymorphic site is a complementary match to one of the deoxynucleoside triphosphates in the reaction, the primer is extended past the polymorphic site, and subsequently incorporates a biotinylated-dCTP before terminating chain extension with the dideoxynucleoside triphosphate.

The reaction whose spectrum is shown in FIG. 19B is one in which the polymorphic site on the template is A. Therefore a dideoxy-TTP is incorporated at the first base past the primer, and chain extension is terminated prior to incorporation of the biotinylated-dCTP, which results in a lack of signal in the mass spectrum.

FIG. 20A and FIG. 20B show two mass spectra from primer extension analyses in which a mixture of three primers, differing only in their 3'-end-bases and each containing unique mass labels, is extended with biotinylated dideoxynucleoside triphosphate. In FIG. 20A the mass spectrum shows signal predominantly for the primer whose 3'-end base (primer A) is a perfect match for the template used in the reaction. The spectrum in FIG. 20B is from a reaction in which the template is changed from the reaction in FIG. 20A in such a way that the 3'-end base matches to a different primer and gives predominantly signal from extension of primer E.

FIG. 21A and FIG. 21B show two mass spectra comparing the chemical cleavage rates for double-stranded versus single-stranded DNA. A cleavable oligonucleotide containing a 5'-S—P bond is cleavable by AgNO3. Two cleavage reactions are run. In the first reaction the cleavable oligonucleotide is hybridized to a complementary oligonucleotide to make it double-stranded prior to adding cleavage reagent. The second reaction is performed on single-stranded oligonucleotide. The mass spectrum in FIG. 21A shows the products from cleavage of double-stranded DNA. The cleavage products are expected at masses of 6560 Da and 1470 Da, while the uncleaved oligonucleotide is seen at 8012 Da. The spectrum of FIG. 21A indicates that only about 5% cleavage has occurred. The spectrum in FIG. 21B, which is from cleavage of single-stranded oligonucleotide demonstrates that under the same conditions, cleavage is about 90% complete.

FIG. 22A and FIG. 22B show two mass spectra from a probe assay of a gene-specific RNA transcript. Two exonuclease III digestions reactions are run. In both reactions a mixture of two probes is present and the template consists of either RNA transcript or the DNA PCR-product template from which the RNA is transcribed. Only one of the probes is complementary to the RNA transcript the other probe is complementary to the opposite strand. Therefore is mass label signal is obtained from the DNA PCR product, signals for both probes are seen, while if the signal is obtained from RNA transcript, only one signal is seen.

In FIG. 22A the mass spectrum shows the resulting released mass label for the reaction in which RNA transcript is present. Since only one signal is seen, the signal must come from digestion of the probe hybridized to the RNA transcript. The second reaction contains a 100-fold greater amount of DNA PCR product than is present in the first reaction, and no RNA transcript.

FIG. 22B shows the mass spectrum resulting from the second reaction. The presence of signals from both probes confirms the fact that the signal in FIG. 22A comes from RNA-hybridized probe.

FIG. 23A, FIG. 23B, FIG. 23C, and FIG. 23D show a set of four mass spectra which compare the analyte selectivity of two different matrices for MALDI. The samples used for the comparison are equimolar mixtures of a nucleotidylated peptide and an oligonucleotide obtained by a selective chemical cleavage of an oligonucleotide-peptide conjugate. FIGS. 23A and 23B compare spectra of the same sample obtained with 2,5-dihydroxybenzoic acid matrix (FIG. 23A) and with 3-HPA matrix (FIG. 23B). The peptide signal predominates in FIG. 23A while the oligonucleotide predominates in spectrum FIG. 23B due to differing desorption selectivities or efficiencies of the matrices for the peptide and the oligopeptide. The spectra in FIGS. 23C and 23B make the same comparison with a different sample showing that the ionization selectivity is general.

Figure 24:
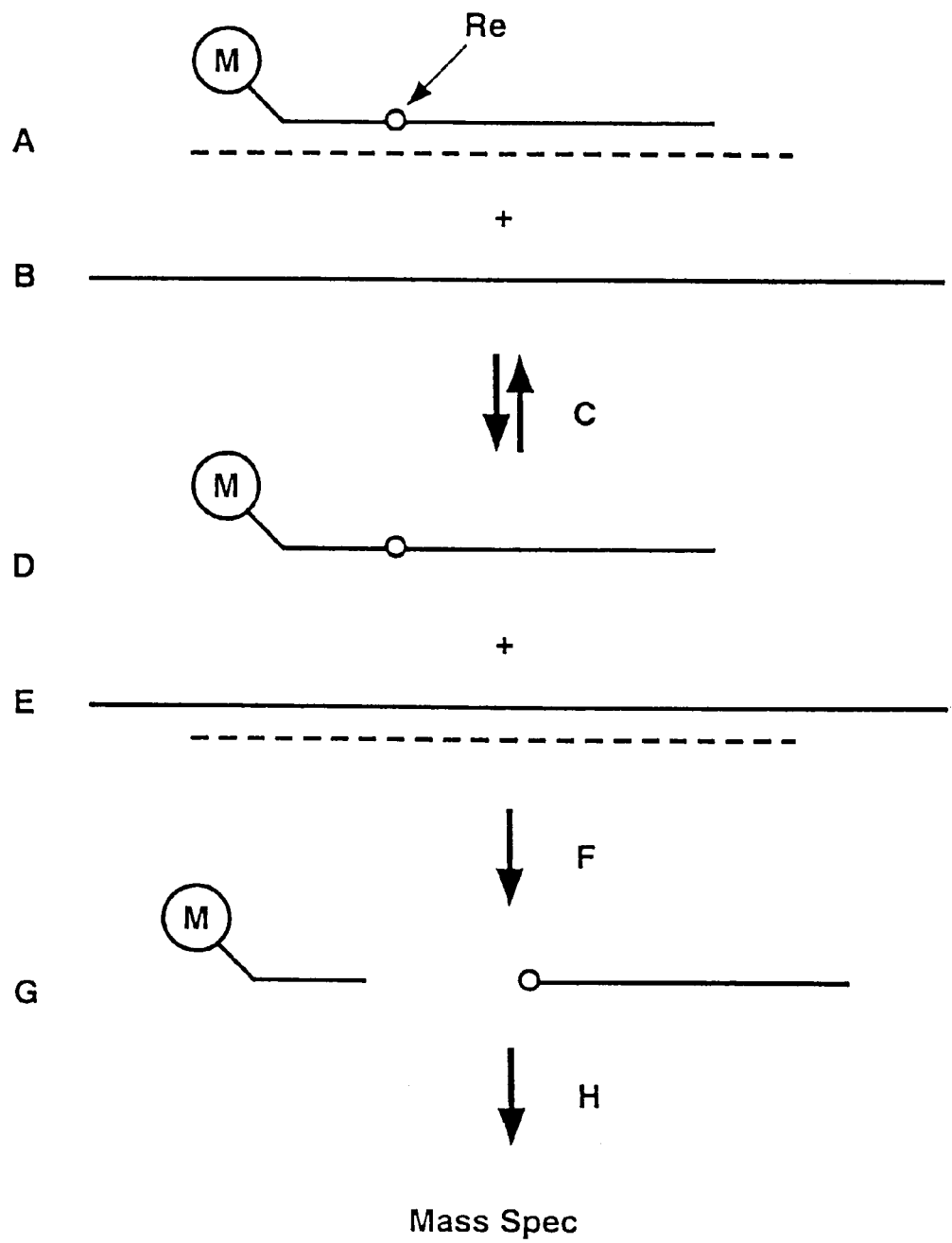

FIG. 24 illustrates the use of a double-stranded, mass-labeled nucleic acid probe for detecting and quantifying the presence of a nucleic acid target sequence. Contained within the double-stranded probe is a chemical cleavage group that, under proper conditions, only cleaves when the nucleic acid probe is single-stranded. Examples of chemical cleavage groups that demonstrate enhanced cleavage rates when single stranded include chemically labile nucleic acid backbone modifications such as 5'-(S)-phosphorothioate, 3'-(S)-phosphorothioate, 5'-(N)-phosphoramidate, 3'-(N)-phosphoramidate, and ribose. Probing of a nucleic acid target sequence involves combining the double-stranded probe (A) with the single-stranded target (B) and allowing them to denature and anneal under equilibrium conditions (C). The probe strand containing the mass label and single-strand-specific release group (labeled Re) is homologous to the target nucleic acid; the complementary strand is also complementary to the target. The other products of this equilibrium event are the mass-labeled, cleavable strand in single-stranded form (D), and the complementary strand annealed to the target (E). The amount of complementary strand released from the mass-labeled strand and annealed to the target is proportional to the concentration of the target nucleic acid. Following the annealing process the probes are treated with a single-strand-specific chemical cleaving agent (F) yielding cleaved single-stranded probe (G) and detected and quantitated by mass spectrometry (H). As with other mass-labeled probes described here, the mass label may be wholely or only partially contained within the nucleic acid probe or reactive group and may include the use of nucleic acid mimics.

Figure 25:
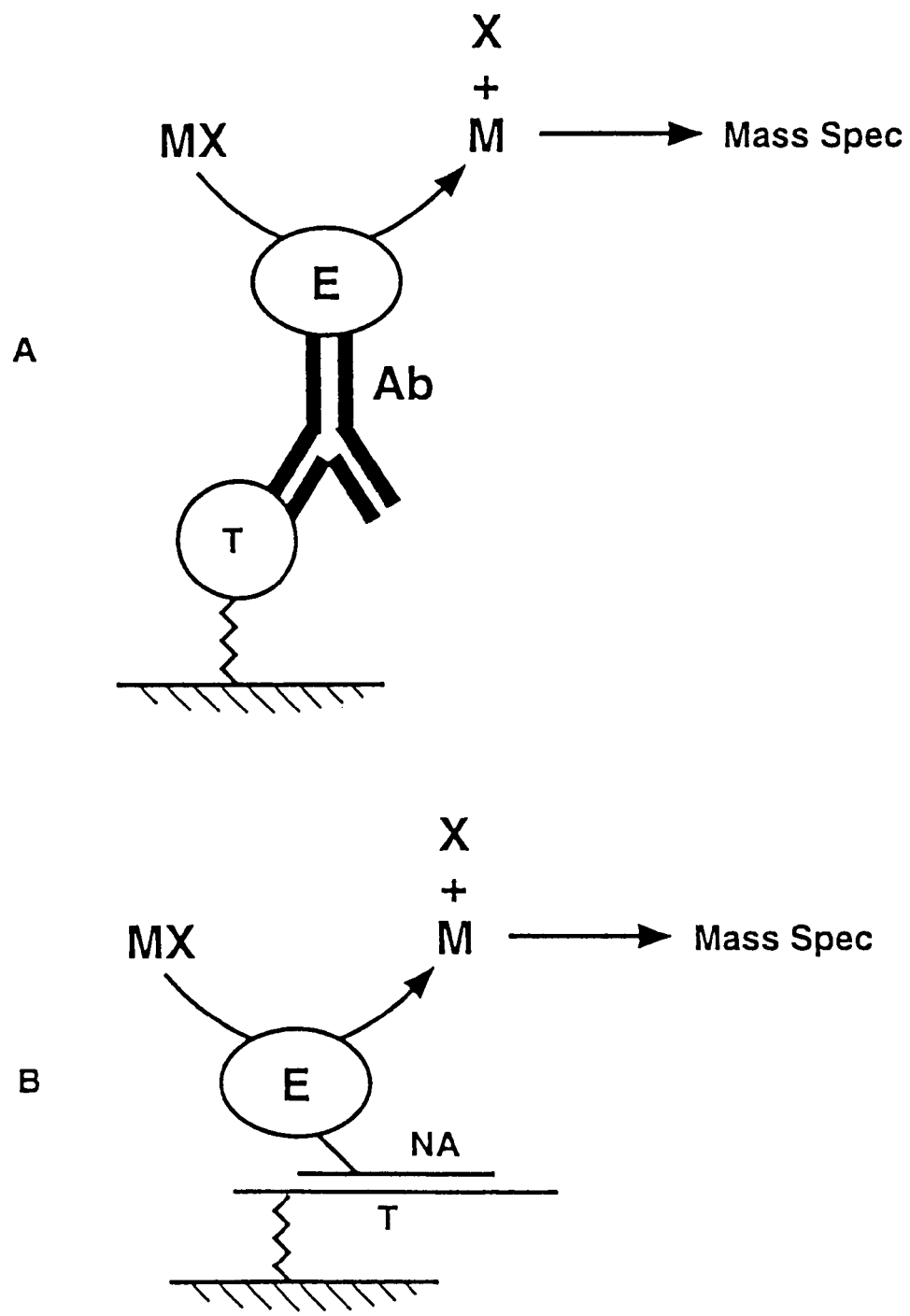

FIG. 25 illustrates the use of mass-labeled substrates in enzyme-linked affinity assays. Specifically illustrated are the cases where the target molecule (labeled T) is a protein (A) and a nucleic acid (B). In illustration (A), an antibody (labeled Ab) is used to recognize the solid-phase bound target. The antibody is conjugated to the enzyme (labeled E) used to produce signal. In this particular affinity assay, the enzyme recognizes a mass-label substrate (labeled MX) and converts it to product which in this example is a cleavage event to form two products (labeled M and X) which are then analyzed by mass spectrometry. Regarding the mass label substrates, the primary requirement is that the enzyme modify the mass of the substrate when it is converted to product by either adding or removing chemical moieties from the substrate. In illustration (B), the antibody has been replaced by a nucleic acid probe that is then conjugated to the signal producing enzyme. The assay is extremely generalizable and one skilled in the art would be able to identify a variety of combinations of probe and target, as well as enzymes and mass-label substrates that may be used.

FIG. 26 illustrates two examples of mass-label substrates for use in enzyme-linked affinity assays. Specifically illustrated are two examples, (A) a double-stranded oligonucleotide containing a restriction endonuclease site (labeled R), and (B) a polypeptide containing a specific proteolytic linkage. In both examples it is possible to develop a repertoire of enzymes and mass-label substrates, since a variety of restriction endonucleases and proteases exist that exhibit either sequence-specific or monomer-specific cleavage activity. Use of these classes of enzymes allow a plurality of affinity assays to take place simultaneous within the same reaction vial. All producing mass-differentiable mass-label products. As with other mass-labeled probes described here, the mass label may be wholely or only partially contained within the nucleic acid or polypeptide substrate and may include the use of nucleic acid mimics or non-natural amino acids.

DESCRIPTION OF ILLUSTRATIVE EMBODIMENTS

The present invention is directed to the composition and use of releasable, nonvolatile mass labels for chemical analysis. The mass labels will be detectable by mass spectrometry. The present invention also describes novel methods utilizing mass labels of any form. The term nonvolatile as used herein refers to a molecule which when present in its pure, neat form and heated, does not sublimate intact to any significant extent. Also included in the definition of nonvolatile compounds are compounds which when present in their pure, neat form cannot be practically analyzed by mass spectrometry when conventional gas chromatography is employed in the sampling process. An advantage of using nonvolatile mass labels versus volatile mass labels is that the sample mixtures are thereby easily physically stable after release. The mass labels described may be attached to a probe molecule that can specifically interact with the intended target. In some cases, a special release group may be included to chemically link the mass label to the probe.

It is also possible to use mass labels which have negligible vapor pressure at room temperature but can be considered volatile by the above definition. In the present work, the novel mass labels released from the probe molecule evaporate insignificantly if at all at room temperature and are not efficient electrophores. Molecules belonging to this category are termed involatile mass labels.

The compounds of the present invention are useful for detecting a wide variety of biomolecular interactions. Representative examples include identification of gene sequences, identification of non-coding nucleotide sequences, identification of mutations within a gene or protein sequence, detection of metals, detection of toxins, detection of receptors on an organism or a cell, characterization of antibody-antigen interactions, enzyme-substrate interactions and characterization of ligand interactions.

A. Mass Labels

Mass label is a term that can be used synonymously with tag or signal. Examples of the types of mass labels for the present invention include a repertoire of compounds, preferably ones that share similar mass spectrometric desorption properties and have similar or identical coupling chemistries in order to streamline synthesis of multiple mass label variants. A mass label of the present invention is detectable by mass spectrometry. Representative types of mass spectrometric techniques include matrix-assisted laser desorption ionization, direct laser-desorption, electrospray ionization, secondary neutral, and secondary ion mass spectrometry, with laser-desorption ionization being preferred. The dynamic range of mass spectral measurements can generally be extended by use of a logarithmic amplifier and/or variable attenuation in the processing and analysis of the signal. An example of a peptide mixture separated by mass spectrometry is shown in FIG. 13.

Mass labels may include a vast array of different types of compounds including biopolymers and synthetic polymers. Representative biological monomer units that may be used as mass labels, either singly or in polymeric form, include amino acids, non-natural amino acids, nucleic acids, saccharides, carbohydrates, peptide mimics and nucleic acid mimics. Preferred amino acids include those with simple aliphatic side chains (e.g., glycine, alanine, valine, leucine and isoleucine), amino acids with aromatic side chains (e.g., phenylalanine, tryptophan, tyrosine, and histidine), amino acids with oxygen and sulfur containing side chains (e.g., serine, threonine, methionine and cysteine), amino acids with side chains containing carboxylic or amide groups (e.g., aspartic acid, glutamic acid, asparagine and glutamine), and amino acids with side chains containing strongly basic groups (e.g., lysine and arginine), and proline. Derivatives of the above described amino acids are also contemplated as monomer units. An amino acid derivative as used herein is any compound that contains within its structure the basic amino acid core of an a amino-substituted carboxylic acid, with representative examples including but not limited to azaserine, fluoroalanine, GABA, ornithine, norleucine and cycloserine. Peptides derived from the above described amino acids can also be used as monomer units. Representative examples include both naturally occurring and synthetic peptides with molecular weight above about 500 Daltons, with peptides from about 500-5000 Daltons being preferred. Representative examples of saccharides include ribose, arabinose, xylose, glucose, galactose and other sugar derivatives composed of chains from 2-7 carbons. Representative polysaccharides include combinations of the saccharide units listed above linked via a glycosidic bond. The sequence of the polymeric units within any one mass label is not critical; the total mass is the key feature of the label.

The monomer units according to the present invention also may be composed of nucleobase compounds. As used herein, the term nucleobase refers to any moiety that includes within its structure a purine, a pyrimidine, a nucleic acid; nucleoside, nucleotide or derivative of any of these, such as a protected nucleobase, purine analog, pyrimidine analog, folinic acid analog, methyl phosphonate derivatives, phosphotriester derivatives, borano phosphate derivatives or phosphorothioate derivatives.

Mass labels according to the present invention may also include any organic or inorganic polymer that has a defined mass value, remains water soluble during bioassays and is detectable by mass spectrometry. Representative synthetic monomer units that may be used as mass units in polymeric form include polyethylene glycols, polyvinyl phenols, polymethyl methacrylates, polypropylene glycol, polypyroles, and derivatives thereof. A wide variety of polymers would be readily available to one of skill in the art based on references such as Allcock et al. (1981) which describes the properties of many additional polymers contemplated for use in the present invention. The polymers may be composed of a single type of monomer unit or combinations of monomer units to create a mixed polymer. The sequence of the polymeric units within any one mass label is not critical; the total mass is the key feature of the label.

For nonvolatile mass labels having mass below about 500 Da, usually significant ionic character is required; representative examples include polyethylene glycol oligomers of quaternary ammonium salts (e.g., $R-(O-CH_2-CH_2)n-N(CH_3)_3^+.Cl^-$) and polyethylene glycol oligomers of carboxylic acids and salts (e.g., $R-(O-CH_2-CH_2)_n-CO_2^-.Na^+$).

Examples of involatile mass labels typically include small oligomers of polyethylene glycol and small peptides (natural or modified) less than about 500 Da in molecular weight. In these instances, as for all of the cases considered herein, mass analysis is not by electron attachment.

Mass labels of the present invention may also include a variety of nonvolatile and involatile organic compounds which are nonpolymeric. Representative examples of non-volatile organic compounds include heme groups, dyes, organometallic compounds, steroids, fullerenes, retinoids, carotenoids and polyaromatic hydrocarbons.

In addition to the polymer or mixed polymer mass labels described, mass-labels or the present invention also include mixed mass labels containing a mass-variable polymeric component and a nonpolymeric mass static component. A representative example includes a set of mass labels with a polymeric component where the number of repeat units within the set is a range from about 10 to 100, and on each polymer is a compound with a fixed large mass. In a preferred embodiment, the mass labels within a set all contain the same mass static component. In this preferred set of compounds only the length of the polymer is changed to provide a set of mass labels with incremental increases in mass and a relatively uniform signal between mass labels. These compounds provide a means for using mass labels with desirable spectral properties but are not available in a large repertoire of different masses.

It is preferable when using multiple mass labels on a probe, to avoid signal overlap. In addition to presenting a large, primary signal for a mass label with a single charge, there is also the potential for multiply charged versions of a mass label to present a signal as well as dimerized versions of a mass label. The presence of multiple signals for a single mass label can potentially overlap with and obscure the signal for the primary peak of a second mass label. Thus typically the range of mass labels used for a given analysis may have a mass range where no multiply charged or dimer species can interfere with the detection of all mass labels, for example, the mass labels may have a range of masses wherein the smallest mass-label is more than half the mass of the largest mass label.

B. Reactive Groups

The mass label is typically attached to a reactive group. The reactive groups of the present invention may be any biomolecule capable of specific molecular recognition. In particular, the reactive group may form a specific interaction with the target molecule. This interaction may be noncovalent, for example, hybridization of an oligonucleotide to a DNA target, or covalent such as crosslinking. Representative reactive groups of the present invention include polypeptides, antibodies, enzymes, polynucleic acids, lipids, steroids, carbohydrates, antibiotics and compounds such as neocarzinostatin which have a preference for certain DNA sequences, with polynucleic acids preferred and oligonucleotides being more preferred. Representative steroid hormones include estrogens, progestins and androgens.

Representative reactive group-target molecule interactions include oligonucleotide-oligonucleotide hybridization, polynucleotide-polynucleotide interactions, enzyme-substrate or substrate analog/intermediate interactions, polypeptide-nucleic acid interactions, protein-ligand interactions, receptor-ligand interactions, lipid-lipid interactions, carbohydrate-carbohydrate interactions, polypeptide-metal interactions, nucleic acid-metal interactions or antigen-antibody interactions.

In certain embodiments the probe may be a synthetic oligonucleotide or enzymatically synthesized oligonucleotide that may be a DNA molecule, an RNA molecule, or some variant of those molecules, such as a peptide nucleic acid. The oligonucleotide will typically be able to selectively bind a substantially complementary sequence. As used herein a substantially complementary sequence is one in which the nucleotides generally base pair with the complementary nucleotide and in which there are very few base pair mismatches. The polynucleotide may be relatively small, such as a 10-mer, or larger, such as a kilobase insert in a plasmid or a kilobase amplified nucleic acid ("amplicon") or a long RNA transcript. The polynucleotide can be bigger, smaller or the same size as the target. The probe is distinguished from the target by the fact that the probe contains a mass label.

Representative examples of a covalent interaction between a reactive group and a target include proteins as reactive groups activated with crosslinkers to form conjugates with the target molecule, such as antibody-antigen interactions, enzyme-substrate interactions, receptor-ligand interactions, receptor-membrane interactions or a protein-nucleic acid interaction. Representative crosslinking reagents include chemically activated crosslinkers such as EDC or MBS and photoreactive crosslinkers such as SADP or PNP-DTP.

C. Methods for Releasing the Mass Label

In some embodiments, it may be important to release the mass label from all or most of the reactive group prior to spectrometric analysis, as represented in FIG. 11 for a mass-labeled nucleic acid probe. For this reason, a release group is desirable. A number of means may effectuate the release, including a labile chemical linkage between the mass label and the reactive group. A labile chemical linkage as used herein is any moiety which upon treatment with a second chemical agent, light, enzyme or heat will cleave the moiety and release the mass label. These linkages may include chemically cleavable groups incorporated within the phosphate backbone linkage (e.g. replacement of phosphate with a phosphoramidate) or as a substituent on or replacement of one of the bases or sugars of the oligonucleotide primer (e.g., a modified base or sugar, such as a more labile glycosidic linkage). Such chemically cleavable groups would be apparent to one of skill in the art in light of the present disclosure and include, for example, dialkoxysilane, 3'-(S)-phosphorothioate, 5'-(S)-phosphorothioate, 3'-(N)-phosphoroamidate, 5'-(N)-phosphoroamidate, and ribose. It has also been found experimentally that such groups cleave much more rapidly when the probe is in single-stranded form than when hybridized to a complementary strand. An example of this kinetic selectivity is presented in Example 9. The chemically cleavable site should generally be stable under the amplification, hybridization and washing conditions to be employed. Other examples of labile chemical, linkers consist of groups cleavable by oxidation such as dialkyl tartrate, base cleavable groups such as bis[2(alkoxy-carbonyloxy)ethyl]sulfone, silyl ethers and ketals which will cleave upon treatment with fluoride ion or acid, ortho-nitrobenzyl ethers which will cleave upon irradiation with light, and groups cleavable by reduction such as dialkyl disulfides.

A preferred labile chemical linkage includes a disulfide bond which upon treatment with a sulfhydryl reagent, such as 2-mercaptoethanol, reduces the disulfide bond into two —SH groups. For mass labels that are chemically cleaved from probes, it may be preferable to remove or wash away any unincorporated reactive group monomers so that they are not visualized in the mass spectrometer.

In other embodiments of the invention, however, no additional linkage group will be needed, as the release group may be contained within the reactive group. Released mass labels therefore, may contain none, a portion, or the whole of the reactive group still attached to the specific mass label. Representative examples of release groups contained within a reactive group include the endogenous peptide linkages between amino acids in a polypeptide and the endogenous phosphodiester bond linkages between bases in a polynucleotide. When the reactive group is a polynucleotide, the mass label may be released during enzymatic (nuclease) digestion of the probe nucleotide backbone, or an acid-induced digestion of the probe nucleotide backbone. These endogenous linkages may also be modified to target a specific sequence within the reactive group. Examples include modified phosphodiester bonds such as phosphorothioates, phosphoramidates and dialkylsilyl ketals. Nucleotide sequences may also be introduced for recognition by an endonuclease (restriction enzyme) such as Type II or Type IIS restriction endonucleases. In certain embodiments a phosphodiester bond will be the release group as recognized by an exonuclease enzyme. Temperature labile release is also contemplated. Representative examples include thermal melting of a hybridized oligonucleotide from a DNA target or temperature dependent denaturation of a protein to release a bound molecule.

Specific peptide linkages may also be introduced within a polypeptide reactive group. Examples include peptide linkages which are specifically cleaved by chemicals such as a methionine recognized by CNBr, or tryptophan which can be cleaved by either iodosobenzoic acid or BNPS-skatole. Peptide linkages may also be introduced for recognition by an enzyme such as trypsin.

A further example of endogenous bonds as release groups include chemical or enzymatic cleavage at a glycosidic bond. One skilled in the art would recognize that a wide variety of release approaches would be within the scope of the present invention.

D. Selective Release of Mass Labels

In some of the embodiments described herein, involving the use of one or more different nucleic acid probes, use of mass-labeled nucleic acid probes may depend on the selective release of certain mass-labels correlating to the occurrence of a particular event. For instance, release of a mass-label may indicate that a hybridization event has occurred between a particular mass-labeled nucleic acid probe and a nucleic acid target sequence. An approach to selective release can involve targeted nuclease digestion of only hybridized probes existing in a double-stranded form as shown in FIG. 12. A number of nucleases, for example restriction endonucleases and DNase 1, only digest double-stranded nucleic acids. Consequently treatment with such enzymes will only release mass-labels from nucleic acid probes that have successfully hybridized to a target sequence. As an alternative, a nuclease that only recognizes a nucleic acid sequence present in single-stranded form, including S1 nuclease, could be used to yield signal and identity data for probes that do not undergo hybridization.

The use of a hybridization probe of at least about 10-14 nucleotides in length allows the formation of a duplex molecule that is both stable and selective. Molecules having contiguous complementary sequences over stretches greater than 10 bases in length may be employed to increase the stability and selectivity of the hybrid. One may generally prefer to design nucleic acid molecules having complementary stretches of about 15 to about 20 contiguous nucleotides, or even longer where desired. For example, one may prefer to design nucleic acid molecules of about 25, about 30, about 35, about 40, about 45, or about 50 contiguous nucleotides and so on. In this context, the term "about" indicates that the nucleic acid molecule may vary from the stated length by from 1 to 4 nucleotides. For example, "about 25" may be understood to include 21, 22, 23 and 24; "about 30" may be understood to include 26, 27, 28 and 29; "about 35 may be understood to include 31, 32, 33 and 34; and so on.

Hybridization probes may be selected from any portion of a target sequence. The choice of probe and primer sequences may be governed by various factors, such as, by way of exemplification and not limitation, one may employ primers from regions near the termini of the total sequence, or from the ends of the functional domain-encoding sequences or one may employ probes corresponding to the entire DNA. Probes may be designed to identify homologous genes between species including human or one may employ wild-type and mutant probes or primers with sequences designed to identify human or other non-human subjects that carry a certain mutation and thus may be susceptible to disease or a pharmaceutical agent.

Variable parameters for hybridization include temperature, time, salt concentration and formamide concentration. Hybridization is understood to mean the formation of stable, anti-parallel duplex molecules based on the specific hydrogen bonding of complementary nucleotide bases of the nucleic acid molecules The tendency for two complementary strands of nucleic acid in solution to anneal or hybridize by forming hydrogen bonds between their complementary bases, is critically dependent on the concentration of monovalent or divalent cations in the solution. Sodium ($Na^+$), has been the cation of choice for determining the effects of salt concentration on the stability of duplex nucleic acids. Above the threshold $Na^+$ concentration, two complementary single strands (either DNA or RNA) of nucleic acid will hydrogen bond through interaction of the bases in each strand, to form a double-stranded molecule of DNA, RNA, or even a DNA-RNA heteroduplex. Complementary bases are adenosine (A) and thymidine (T) (in DNA), or adenosine and uridine (U) (in RNA), and cytosine (C) and guanine (G) in both DNA and RNA. Two hydrogen bonds are formed between paired A and T or A and U residues, while C-G base pairing results in the formation of three hydrogen bonds. The G-C base pair is therefore a stronger interaction than the A-U or A-T base pair. In general, hydrogen bonding (leading to duplex formation) does not occur between non-complementary bases. The ability of two single strands to form a stable double-stranded duplex depends on the sequence of bases in each strand being complementary to the other, such that when the strands are aligned in an antiparallel orientation, sequential juxtaposed bases are able to form hydrogen bonds. Although hydrogen bonding between any two complementary bases provides only a weak binding energy, the cumulative binding energy between many sequential paired bases provides sufficient attractive forces to hold the strands together in a stable duplex. Cations enhance the tendency for complementary strands to form hydrogen bonds, by masking the negative charges of the phosphate groups in the phosphodiester linkages which form the "backbone" of the nucleic acid strands. At low concentrations of positively charged ions, repulsive forces between negatively charged strands favor their single-stranded or denatured conformation; as cation concentration is raised, the negative charges are masked, complementary bases pair through hydrogen bonding, and a duplex nucleic acid molecule is formed. In a duplex containing a mismatched (non-complementary) base pair, the single unpaired position in the two otherwise complementary strands provides the target for the single-strand specific RNase in the RNase protection assay.

Other parameters besides cation concentration affect the tendency of complementary strands to exist in the alternative double-stranded or single-stranded conformations. Temperature is a critical variable; as the temperature of a solution of duplex nucleic acid molecules is raised, hydrogen bonds are broken first in A-U rich regions and finally in G-C rich regions, until above a critical temperature, the complementary strands come apart. The composition of the two strands, i.e., their % GC content, determines the critical temperature for duplex denaturation at a given ionic strength. As a corollary, the % GC also determines the threshold concentration of $Na^+$ needed to maintain duplex stability at a given temperature. Stability of duplex nucleic acid molecules in solution is also affected by the nature of the solvent. For example, duplexes are much less stable in formamide (which destabilizes hydrogen bonds) than in aqueous solution, a fact exploited by molecular biologists to achieve nucleic acid hybridization at lower temperatures than would otherwise be required.

Equations have been derived to relate duplex formation to the major variables of temperature, salt concentration, nucleic acid strand length and composition, and formamide concentration.

Eg:

$$Tm = 81.5 - 16.6(\log [Na^+]) + 0.41(\% GC) - 600/N \quad \quad 1.$$
(Tm=temperature for duplex to half denature;
N=chain length $$Tm = 81.5 - 16.6(\log [Na^+]) + 0.41(\% GC) - 0.63(\% \text{formamide}) - 600/N \quad \quad 2.$$

One can thus predict whether complementary strands will exist in double-stranded or single-stranded form under a given set of conditions. If conditions are chosen such that complementary strands form a stable duplex, the duplex will in theory be resistant to the nucleolytic action of enzymes (DNases and RNases) which are specific for cleavage of phosphodiester bonds in single-stranded molecules. Many different types of nucleases exist, which vary widely in their substrate specificities. The RNases commonly used in RNase protection assays are specific for cleavage after particular bases in single-stranded RNA molecules. Below the threshold $Na^+$ concentration needed t maintain duplex stability, the complementary RNA strands denature into single strands, which are then substrates for degradation by the RNases. Susceptibility to digestion by RNase A is therefore a functional assay for whether complementary strands exist as single-stranded or double-stranded molecules.

Hybridization

Standard annealing or hybridization procedures are described by Sambrook et al. (1989). Generally they entail two or more nucleic acids, for example probe and test sample nucleic acids, to be mixed together, denatured and then subjected to conditions in which complementary strands anneal, or base pair by hydrogen bonding to form double strands. The annealed strands are said to be hybridized. For example, the mixture may be heated to from about 90° C. to about 95° C. for about three minutes and then gradually cooled to a lower temperature, 42° C. for example, for a period of time sufficient to allow hydrogen bonding of the complementary strands. The time required for annealing of complementary strands depends on the concentration of each strand and will vary from a few minutes (for reactions where both probe an test nucleic acids are present at high concentrations), to several hours or overnight for reactions having at least one species present at low concentration. It is therefore advantageous to use high concentrations of probe and test sample nucleic acids, such as may be generated by PCR amplification and/or transcription of PCR amplified sequences.

Depending on the application envisioned, one may employ varying conditions of hybridization to achieve varying degrees of selectivity of the probe towards the target sequence. For applications requiring high selectivity, one may typically employ relatively stringent conditions to form the hybrids, e.g., relatively low salt and/or high temperature conditions, such as provided by 0.02M-0.15M NaCl at temperatures of 50° C. to 70° C. Such selective conditions tolerate little, if any, mismatch between the probe and the template or target strand.

Of course, for some applications, for example, where one desires to identify mutants employing a mutant primer strand hybridized to an underlying template or where one seeks to isolate protein-encoding sequences from related species, functional equivalents, or the like, less stringent hybridization conditions may typically be employed to form the heteroduplex. In these circumstances, one may employ milder hybridization conditions, such as 0.15M-0.9M salt, at temperatures ranging from 20° C. to 55° C. Cross-hybridizing species can thereby be readily identified as positively hybridizing signals with respect to control hybridizations. Additionally, conditions may be rendered more stringent by the addition of increasing amounts of formamide, which serves to destabilize the hybrid duplex in the same manner as increased temperature. Thus, hybridization conditions may be readily manipulated to achieve the desired results.

Release Methods

The use of nucleases that selectively digest mass-labeled nucleic acid probes hybridized to a target nucleic acid allows for linear amplification of signal. For example, one may employ a nuclease capable of digesting only the nucleic acid probe and not the target, e.g., a double-strand specific exonuclease to digest a short, linear probe in the presence of a circular target having no end to enable the initiation of exonuclease digestion. Long linear targets may also be used in cases where the exonuclease requires a recessed or blunt double-stranded end. As a probe hybridizes to the target, it is digested, and the digested fragments release from the target and make room for a second copy of the probe to hybridize. The second probe is then digested, and, once again, the target is free for the next hybridization. The repeated cycles of hybridization and digestion leads to a linear amplification of the amount of released mass label in solution, consequently increasing the mass spectrometric signal. It is possible to achieve a many hundred-fold amplification of signal using such a system. See Okano and Kambara, 1995 (exonuclease III); Copley and Boot, 1992 (lambda exonuclease).

Nonselective release events may also be employed with the methods disclosed herein. For example, nonselective cleavage of a disulfide releasing group using a chemical agent such as a phosphine or a mercaptan may be used.

In certain embodiments, detection of the desired label may depend on specific partitioning of the population of reactive groups or targets. Reactive groups that recognize and bind to a particular target may, for example, be immobilized to a specific location. For instance, a target sequence or sequences of nucleic acids may be attached to gridded positions on a solid support such as a filter, glass, gold or to a bead or a group of beads. Mass-labeled oligonucleotides (probes) that do not hybridize to the target sequence may then be separated from probes hybridized to immobilized targets simply by washing the filter or beads. Such approaches may be especially preferred for removal of unhybridized probes where a subsequent nonspecific release mechanism is to be employed. The reverse case may also be employed, in which the labeled probes are immobilized, and the targets are hybridized to them.

Methods described herein may involve the use of a nucleic acid amplification event, such as polymerase chain reaction (referred to as PCR™), to link a mass-labeled nucleic acid probe, used specifically as a primer, to a second primer that is capable of or presently is bound to a solid support. An example of a second primer is one that contains a biotin moiety. Similarly to the embodiment described above, binding of the amplification product to the solid phase affords a mechanism to wash away unused primers and then to nonselectively release the remaining mass labels.

A nucleic acid amplification event, involving the use of one or more different nucleic acid probes, may also be used to convert mass-labeled nucleic acid probes, used specifically as a primers, from single-stranded form to double-stranded form. This conversion allows the use of a double-strand-specific nuclease to selectively release only those mass labels that were attached to primers involved in amplification events. Unused primers remain single stranded and will not release their attached mass labels.

Other methods described herein as part of the present invention, involving the use of one or more different nucleic acid probes, may involve the modification of a select population of probes following their hybridization to a target which would allow for the partitioning of the probe population. Such methods include double-strand dependent addition of biotinylated nucleotides or oligonucleotides to the end of mass-labeled probes using polymerase or ligase, followed by direct capture of the biotinylated probes to a streptavidin modified surface.

As another option, analysis of mass-labeled nucleic acid probes by MALDI mass spectrometry may be performed using a matrix that selectively desorbs and efficiently ionizes intact released mass labels but not mass labels still coupled to their respective nucleic acid probes. Nucleic acid molecules often do not desorb well in many matrices which are yet effective for the desorption of released mass labels, and this difference can be accentuated by the presence of impurities such as salts. Mass-labeled nucleic acid probes may typically be analyzed by direct laser-desorption mass spectrometry without further purification if, for example, the released mass label(s) are detected much more efficiently than unreleased labels. The same holds true for other forms of mass spectrometry. Thus, in a preferred embodiment using laser-desorption mass spectrometry, physical partitioning of the released and unreleased mass labels may not be required. One skilled in the art in light of the present disclosure can envision the use of a variety of other techniques for selectively partitioning probes involving probe-label synthesis, label release, and label mass spectral detection, in various combinations.

E. Synthetic Techniques

Figure 1A:
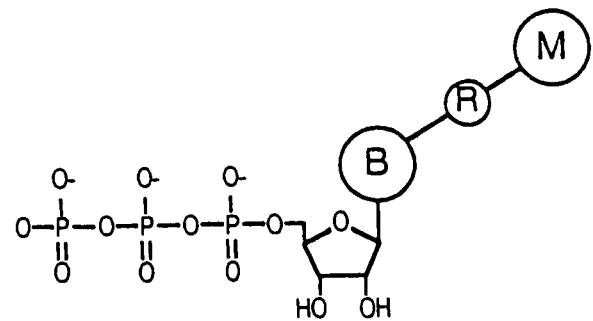
FIG. 1A and FIG. 1B show generalized examples of two mass-labeled building blocks for the preparation of mass-labeled polynucleotides, a mass-labeled nucleoside triphosphate (FIG. 1A) and a mass-labeled nucleoside phosphoramidite (FIG. 1B). In these FIGS., B refers to a base, R to an optional releasing linkage, and M to a mass label. Mass labels may also be added after polynucleotide synthesis via linker reagents.

Mass labels may be added to the reactive group during synthesis, or the reactive group may be modified after synthesis. For example, the modification of nucleic acid or amino acid building blocks provides a convenient route for developing generalized methods of mass-labeling reactive groups during synthesis. For example, as the polypeptide or polynucleic acid is being synthesized, different mass-labeled nucleotides or amino acids may be added to the mixture and incorporated into the growing polymer. A generalized example of a mass-labeled nucleoside triphosphate is depicted in FIG. 1A. One skilled in the art would in light of the present disclosure envision a variety of attachment schemes and positions of attachment. Generally, the attachment of a mass label should not substantially inhibit the interaction between the reactive group and target molecule, such as the hydrogen-bonding of the mass-labeled base and the complementary target base, or disrupt the proper folding of a polypeptide to form an active protein. Furthermore, in the case of a mass-labeled nucleoside triphosphate, the label should typically not inhibit polymerization by a polymerase enzyme.

One synthesis approach of the present invention, involves the use of mass label modified nucleoside triphosphates that are incorporated by a polymerase to produce a mass-labeled polynucleotide. Using this method, it is easy to load a nucleic acid probe with many copies of a mass label. Polymerase-based methods allow for the inexpensive synthesis of very long probes hundreds to tens of thousands of bases in length by incorporation into an RNA transcript of PCR™ amplicon.

Where the reactive group is a protein, the mass label may be a length of amino acids forming a peptide attached to either the carboxyl or amino terminus of the protein. The composition of the mass label may be coded directly into the DNA sequence immediately adjacent to the coding region of the protein that represents the reactive group. Subsequent transcription and translation of this DNA sequence yields a product whereby the peptide mass label is fused to the protein.

F. Enzymatic Amplification Techniques

Nucleic acid amplification methods may be used to prepare mass-labeled probes or to detect the presence of a target sequence. One of the best known amplification methods is the PCR™ which is described in detail in U.S. Pat. No. 4,683,195, U.S. Pat. No. 4,683,202 and U.S. Pat. No. 4,800,159, each incorporated herein by reference, and in Innus et al. (1990, incorporated herein by reference).

In PCR™, two primer sequences are typically prepared which are complementary to regions on opposite complementary strands of the target sequence. The primers may hybridize to form a nucleic acid:primer complex if the target sequence is present in a sample. An excess of deoxynucleoside triphosphates are also added to a reaction mixture along with a DNA polymerase, e.g., Taq polymerase, that facilitates template-dependent nucleic acid synthesis.

If the marker sequence:primer complex has been formed, the polymerase will cause the primers to be extended along the marker sequence by the addition of nucleotides. By raising and lowering the temperature of the reaction mixture, the extended primers will dissociate from the marker to form reaction products, excess primers will bind to the marker and to the reaction products and the process is repeated. These multiple rounds of amplification, referred to as "cycles", are conducted until a sufficient amount of amplification product is produced.

A reverse transcriptase PCR™ ("rtPCR™") amplification procedure may be performed in order to quantify the amount of mRNA amplified. Methods of reverse transcribing RNA into cDNA are well known and described in Sambrook et al., 1989.

Another method for amplification is the ligase chain reaction ("LCR"), disclosed in European Patent Application No. 320,308, incorporated herein by reference. In LCR, two complementary robe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference, describes a method similar to LCR for binding probe pairs to a target sequence.

Qbeta Replicase, described in PCT Patent application No. PCT/US87/00880, may also be used as still another amplification method in the present invention. In this method, a replicative sequence of RNA which has a region complementary to that of a target is added to a sample in the presence of an RNA polymerase. The polymerase will copy the replicative sequence.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention. Such an amplification method is described by Walker et al. (1992, incorporated herein by reference).

Strand Displacement Amplification ("SDA") is another method of carrying out isothermal amplification of nucleic acids which involves multiple rounds of strand displacement and synthesis. A similar method, called Repair Chain Reaction (RCR), involves annealing several probes throughout a region targeted for amplification; followed by a repair reaction in which only two of the four bases are present. The other two bases can be added as biotinylated derivatives for easy detection. A similar approach is used in SDA.

Target specific sequences may also be generated using a cyclic probe reaction ("CPR"). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

Other nucleic acid amplification procedures include transcription-based amplification systems ("TAS"), including nucleic acid sequence based amplification ("NASBA") and 3SR (Kwoh et al., 1989; PCT Patent Application WO 88/10315, each incorporated herein by reference).

In NASBA, the nucleic acids may be prepared for amplification by standard phenol/chloroform extraction, heat denaturation of a clinical sample, treatment with lysis buffer and minispin columns for isolation of DNA and RNA or guanidinium chloride target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once again with a polymerase such as T7 or SP6. The resulting products, whether truncated or complete, indicate target specific sequences.

European Patent Application No. 329,822 (incorporated herein by reference) disclose a nucleic acid amplification process involving cyclically synthesizing single-stranded RNA ("ssRNA"), single-stranded DNA ("ssDNA"), and double-stranded DNA ("dsDNA"), which may be used in accordance with the present invention.

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

Separation may also be achieved using biologically based interactions such as biotin-streptavidin or antibody-antigen interactions.

In embodiments where the mass labels have been incorporated into the product, detection of the mass labels may be used to confirm amplification. When the mass label is to be added later, amplification products should typically be visualized in order to confirm amplification of the sequences. One typical visualization method involves staining of a get with ethidium bromide and visualization under UV light. Alternatively, if the amplification products are integrally labeled with radio- or fluorometrically-labeled nucleotides, the amplification products may typically be exposed to x-ray film or visualized under the appropriate stimulating spectra, following separation.

G. Chemical Synthesis Techniques

Figure 1B:
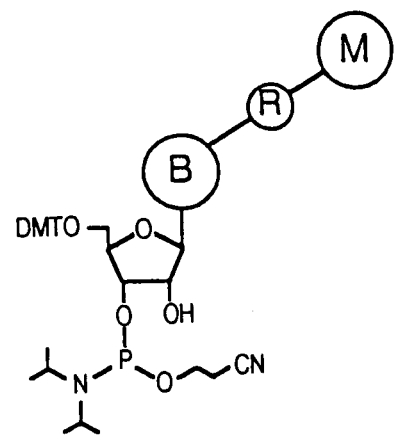

If the probe is chemically synthesized, the mass label may be place at one or more locations within the reactive group. For example, polypeptide compounds of the present invention may be synthesized using known methods for peptide synthesis (Atherton & Shepard, 1989). The preferred method for synthesis is standard solid phase methodology, such as that based on the 9-fluorenylmethyloxycarbonyl ("FMOC") protecting group (Barlos et al., 1989), with glycine-functionalized o-chlorotrityl polystyrene resin. Solid phase peptide synthesis allows for strategic placement of a mass label within the compound. Similarly, an oligonucleotide probe, for example, may be specifically labeled by introducing a modified mass-labeled phosphoramidite at a particular location within the sequence. Chemical synthesis methods also permit the placement of mass labels at the termini of the probe or within an internal linker wherein the mass label is not directly attached to the base of a nucleotide. A generalized example of a mass-labeled phcisphoramidite is shown in FIG. 1B. Chemical synthesis methods for DNA are well known within the art (Agrawal, 1993)

The use of combinations of different mass labels can greatly enlarge the number of unique mass signatures that are available when making a library of nucleic acid probes, while needing only a modest set of different mass label components. As an example, using polymerase-based methods and a repertoire of 40 different mass-labeled thymidine triphosphate nucleotides each with a unique mass label, one may synthesize an enormous array of differentially labeled probes. If combinations of two different mass labels out of the 40 are used for each probe then a total of 780 probes may be made each with a unique, two-mass signature $[=40!/(2!.38!)=780]$. If three different labels are used per probe then 9,880 different combinations are possible $[=40!/(3!.37!)=9,880]$. The trend continues using the example of combination of sets of mass labels from a pool of 40 label molecules as follows: a set of four labels yields 91,390 possible combinations, five labels yields 658,008 possible combinations, six labels yields 3,838,380 possible combinations and so on. Conceivably probes may be made with a unique mass label signature for every gene within humans, and any other organism for that matter. Examples of enzymatic probe synthesis are shown in FIG. 4C and FIG. 4D.

An alternative to the use of mixtures of mass-labeled nucleotides, is the use of mixtures of mass-labeled primers. Nucleic acid probes prepared by an amplification method, such as PCR™, may utilize mixtures of primers whereby each primer contains a different mass label and the same DNA sequence. As with the mass-labeled nucleoside triphosphates, a repertoire of mass labeled primers may be used to prepare many different mass signatures. In addition to using mixtures of primers with a single type of mass label, primers may be prepared containing several different mass labels within a single molecule.

A particular advantage to the solid phase method of synthesis is the modification of these compounds using combinatorial synthesis techniques. Combinatorial synthesis techniques are defined as those techniques producing large collections or libraries of compounds simultaneously, by sequentially linking different building blocks. Libraries can be constructed using compounds free in solution, but preferably the compound is linked to a solid support such as a bead, solid particle or even displayed on the surface of a microorganism. Several methods exist for combinatorial synthesis (Holmes et al., 1995; Burbaum et al., 1995; Martin et al., 1995; Freier et al., 1995; Pei et al., 1991; Bruce et al., 1995; Ohlmeyer et al., 1993); including split synthesis or parallel synthesis. Split synthesis may be used to produce small amounts of a relatively large number of compounds, while parallel synthesis may produce larger amounts of a relatively small number of compounds. In general terms, using split synthesis, compounds are synthesized on the surface of a microparticle. At each step, the particles are partitioned into several groups for the addition of the next component. The different groups are then recombined and partitioned to form new groups. The process is repeated until the compound is completed. Each particle holds several copies of the same compound allowing for facile separation and purification. Split synthesis can only be conducted using a solid support.

An alternative technique known as parallel synthesis may be conducted either in solid phase or solution. Using parallel synthesis, different compounds are synthesized in separate receptacles, often using automation. Parallel synthesis may be conducted in microliter plate where different reagents can be added to each well in a predefined manner to produce a combinatorial library. Parallel synthesis is the preferred approach for use with enzymatic techniques. It is well understood that many modifications of this technique exist and can be adapted for use with the present invention. Using combinatorial methods, a large number of unique mass-labeled probes may be synthesized.

One embodiment is an approach to synthesizing all possible combinations of sequence simultaneously in such a way that each unique sequence within the pool will possess a unique mass signature. The synthetic approach involves the use of a unique set of four mass-labeled nucleotides for each position within an oligonucleotide probe, i.e., a set of four mass labels are used exclusively at position 1, while a different set of four is used exclusively at position 2, and so on. The primary method of synthesizing said probes is chemical using phosphoramidite chemistry though other chemical and enzymatic methods including single base addition by polymerase may also be employed. As an example, synthesis of the combinatorial set of all oligonucleotides 10 bases long would require 40 different phosphoramidites, 10 different A's with unique mass labels, 10 different C's with unique mass labels, 10 different G's with unique mass-labels, and 10 different T's with unique mass labels. The scheme is illustrated in FIG. 4A.

Utility for the complete probe set is diverse. Applications include hybridization assays for identity of cDNAs of other sequences present in a solid phase bound array or some other format, mapping applications, and other diagnostic applications. It is also possible to use the set for random PCR™ amplification assays where the products are separated by electrophoresis and the primers that paired to form the different PCR™ products are identified. These applications also apply to the methods used to identify short sequence reads.

The combinatorial synthesis of probes can be performed as a single reaction in a single receptacle, or it may be performed using the split synthesis technique previously described. If the combinatorial synthesis does not utilize split synthesis techniques, there may be difficulties identifying sequence in cases where multiple probes hybridize. In cases where the full set of probes are used it may be difficult to uniquely identify the sequences of the probes if more than one probe is present at a significant level. One possible approach to limiting the number of probes that hybridize to a particular target is by attaching a unique anchoring sequence to the probe set limiting the locations where the probe can hybridize. This anchoring is similar to the methods used to identify short sequence reads. As described previously, it may also be possible to add extra bases to the end of the probe to lengthen the sequence determination and improve discrimination, if necessary.

A specific example of using the anchored, combinatorially synthesized probes is shown in FIG. 4B. In the case of screening genomic or cDNA clone inserts, the anchored, invariant sequence may be used to hybridize to the know vector sequence immediately adjacent to the insert or in the specific case of a cDNA insert to the poly A/T region of the insert.

For addition of labels to an already synthesized probe, herein referred to as post-modification, various chemically active sites on the probe may be utilized. For example, a proper functionality of a label could be reacted with a primary amine on 5 propargyl amino deoxyuridine, a terminal amino or carboxyl linker, or an endogenous moiety, such as the exocyclic amine in cytosine, guanine, or adenine. Potential linker groups include the heterobifunctional cross-linking agent mal-sac-HNSA (Bachem Inc., Torrence, Calif.), or any of a variety of cross-linking agents available from Pierce Chemical Company (Rockford, Ill.). One skilled in the art could in light of the present disclosure supply other examples. Post modification also allows for the addition of multiple mass labels.

I. Assays with Nonvolatile, Releasable Mass-Labeled Probes

The described mass-labeled nucleic acid probes have a variety of uses. Labeled polypeptides may be used to detect interaction of a reactive group with a specific target. Representative examples include a mass-labeled antibody to detect an antigen either in solution or on a solid support or a mass-labeled enzyme to detect a substrate. One of skill in the art would recognize there are many such interactions detectable using labeled polypeptides to detect interactions with a target molecule.

One preferred embodiment of the invention relates to the simple detection of a specific target nucleic acid.

There are a variety of reasons for detecting a particular nucleic acid sequence. These reasons include, but are not limited to, detection of infectious agents within a clinical sample, detection of an amplification product derived from genomic DNA or RNA or message, RNA, or detection of a gene (cDNA) insert within a clone. Simple detection may employ any combination of the methods described herein for the preparation of the nucleic acid probe and the release and detection of the mass label. One may also quantify the amount detected. Most of these methods involve the use of a hybridization-specific event to trigger the release of a mass label, and in cases where only small amounts of target material are present, the use of an amplification technique.

An advantage to using mass-labeled compounds that are detectable by mass spectrometry methods is the ability to simultaneously detect many target compounds at the same time. Due to broad overlapping spectrums produced by existing fluorescent chromophores, an upper limit for fluorescence multiplexing is most likely to be about ten different labels. With a matrix-assisted laser desorption/ionization time-of-flight ("MALDI-TOF") mass spectrometer or direct laser-desorption mass spectrometer or an electrospray mass spectrometer, multiplexing of tens of hundreds and perhaps even thousands of different mass labels is possible. A nonvolatile pool of labels may provide a wider range of masses and structures. Due to this multiplexing ability, not only can many labeled probes be used at the same time, any individual probe can be labeled with many different labels.

J. Single Nucleotide Polymorphism Detection

Further embodiments involve the detection of single base variations. These applications will generally require a great deal of sensitivity. These applications include detection of "hot spot" point mutations and identification of the base at single nucleotide polymorphism ("SNP") sites. Mass-labeled probes may be prepared that hybridize immediately adjacent to a polymorphic site and a polymerase may then be used to add one base at the site of the polymorphism. The particular base may be added to the probe by many ways. For example, in a preferred embodiment where a single probe is used, a mixture of the four chain terminating triphosphates may be added, each with a unique mass label attached. In the homozygous SNP case only one of the four chain-terminating nucleotides may add to the end of the probe coupling the associated mass label to the probe. Several approaches may be taken in releasing the mass label from the probe. These approaches include, but are not limited to, the use of chemically labile functional groups linking the mass label to the terminating nucleotide, chemically labile functional groups within the backbone of the extended primer or the chain-termination nucleotide, or the use of an enzyme to cleave at one or more of the phosphodiester or glycosidic linkages within the primer extension product. In cases where the mass label release point is within the backbone of the extension product, the released mass label may include the terminal nucleotide or some mass-modified version thereof. In another version where the release point is internal to the primer extension product, the native chain-terminating nucleotides themselves may serve as all or a portion of the mass labels since each base possesses a unique mass. In cases where the mass label is chemically cleaved from the probe, any unincorporated nucleotides may first be removed or washed away so that they are not visualized by the mass spectrometer.

Partitioning of the hybridized mass-labeled chain-terminating triphosphate may be done on the basis of mass differences, as labeled triphosphate hybridized to a target-hybridized probe will have a higher molecular weight than a labeled triphosphate that is not. The probe or target may also be attached to a solid-phase via a number of means including biotin/streptavidin or chemical coupling or UV cross-linking. An alternative is the use of a nuclease to digest the mass-labeled probe. Using a nuclease the mass labeled chain-terminating nucleotide will be released as a monophosphate. The unincorporated mass-labeled chain-terminating nucleotides will remain as triphosphates, and the resulting mass shift to monophosphate will indicate which nucleotide was incorporated. This nuclease method relieves the necessity to remove unincorporated nucleotides prior to analysis.

Another embodiment encompasses the multiplexing of a large number of probes so as to detect many SNPs simultaneously. Preferably mass labels may be present to uniquely tag each of the probes that comprise the pool. The addition of a biotinylated chain-terminating nucleotide at the site of the point polymorphism may also be used to segregate the probe population depending on which probes incorporate a specific biotinylated chain-terminating nucleotide and which do not. As an example, the pool of mass-labeled probes with target may be divided into four reactions. The first reaction would contain only biotinylated dideoxy adenosine triphosphate, the second would contain only biotinylated dideoxy cytidine triphosphate, the third only biotinylated dideoxy guanidine triphosphate, and the fourth only biotinylated dideoxy thymidine triphosphate. Following a single base extension polymerase-dependent reaction in the presence of the proper nucleotide, the extended products are captured, washed and the mass labels are released for mass spectrometric analysis. In the first reaction only those mass-labeled probes that incorporate an A will be visualized. In the second reaction only those mass-labeled probes that incorporated a C will be visualized. For the third and fourth reactions probes that incorporated, respectively a G or a T will be visualized. It is expected that hundreds of probes could be multiplexed in this way.

A person skilled in the art could identify a number of variations of the single or multiplexed probe approach for reading out the SNP based on either the absence or appearance of the mass label or mass change occurring in the mass label. Another example of mass change within a mass label is the case where the mass label is present at the 3' end of the probe. Following polymerase-dependent base extension, the mass label may be released, including the chain terminating base addition as well as the penultimate base. A possible structure for this type of probe is shown in FIG. 2. Placement of the mass label and the release site may be at other bases with a preference of placement near the 3' end. In all cases the mass label should preferably be placed between the release group and the 3' end. In other embodiments it may be preferred to perform what is effectively a short chain terminated sequencing reaction, where, in addition to dideoxy nucleotides, some amount of normal deoxy nucleotides are present. Extension of the primer will result in a nested set of products, each being chain terminated by a dideoxynucleotide correlating to its complementary base on the template strand. In the preferred form, the mass label may be located within the primer near the 3' end which contains a chemical release group. Such a method offers a separate embodiment for short sequence reads as well as detection of one or more SNPs. All of the SNP detection methods described above may involve the use of mass modified forms of the different nucleotides in order to enhance the mass difference between the different possible products.

An alternative preferred embodiment to single base addition for detecting an SNP is the performance of a discriminating exonuclease event in the presence of matching and mismatching oligonucleotide probes. One example of this approach is to combine the use of releasable mass labels with nick translation PCR™. In addition to its polymerase activity, Taq DNA polymerase has both 5' to 3' exonuclease and endonuclease activities. If a fully complementary oligonucleotide probe is placed in the path of polymerization, for example during PCR™ amplification, the polymerase will attack the 5' end of the probe with its exonuclease activity, digesting the molecule until it is too small to remain hybridized. However, if the oligonucleotide is not perfectly complementary near the 5' end, e.g., a mismatch is present nearby, then the end of the probe will fray and be attacked by the endonucleolytic activity of the polymerase rather than the exonuclease activity. The nucleolytically cleaved product, preferably containing the mass label, will have a different final mass depending on whether or not a mismatch was present and how the nuclease cut in response to this mismatch. It has been demonstrated that the initiation of endonucleolytic activity can be influenced by the presence and placement of a mismatch within the hybridization probe (Holland et al., 1991; Lee et al., 1993). Selective placement of a mass label within the oligonucleotide probe relative to the expected mismatch site can be used to yield a differential signal depending on whether or not an actual mismatch is present.

By taking advantage of the high multiplexing capability of mass-labeled probes, one can extend this assay to the simultaneous detection of multiple SNPs. Each of the probes targeting a particular SNP contains one of the four possible bases to complement the site of polymorphism. The placement of the mass label is such that if the probe contains a perfect match to the template, the mass label will be released by the exonuclease activity of Taq polymerase, primarily in a form that includes a single nucleotide. The other probes will create a mismatch and the endonuclease activity of the polymerase will initiate cutting of the probe in such a way that the mass label remains bound to a larger segment of the probe that includes more than one nucleotide. The shift in mass of the mass label cleavage product is diagnostic of whether or not a mismatch has occurred.

When the detection by mass spectrometry is performed using MALDI it may be possible to select a matrix that can visibly discriminate between the smaller product that results from the matching probe and the larger product that results from the mismatched probes such that the smaller product is desorbed more efficiently or selectively. Utilizing a matrix such as 2,5-dihydroxybenzoic acid, sinapinic acid, or α-cyano-4-hydroxycinammic acid, the signal strength decreases as more nucleotides are attached to the probe (Jensen, et al., 1996).

By using a set of 50 mass-labeled probes, as many as 25 biallelic SNPs may be detected in a single tube. As is the case with any PCR™ based detection scheme, the limit of SNPs to be detected will more likely be the result of the limits of multiplexing PCR™. The process, when coupled to high throughput mass spectrometric analysis, can be especially cost efficient when analyzing a small set of polymorphic sites, e.g., in a cluster of exons, as part of a population study where thousands to tens of thousands of samples need to be analyzed.

Nick translation PCR™ combined with mass-labeled probes can also be used as a generalized method for the detection and monitoring of a PCR™ amplification reaction. In this case, only matching probes are present and the mass label is released only if PCR™ of the particular region targeted by a particular probe is amplified.

While the preferred embodiment for these assays is to use nonvolatile releasable mass labels or involatile releasable mass labels, other types of labels can be used as well, such as isotopic mass labels, volatile mass labels (including electrophores), fluorescent labels, and chemiluminescent labels.

K. Short Sequence Reads

In another preferred embodiment of the invention, the mass-labeled probes may be used to identify short sequences. In particular, combinations of hybridization and enzymatic (polymerase or ligase) extension can be employed with the labeled probes to identify short sequence runs adjacent to a "priming" or anchoring region. There are three optimal methods for doing this. The first method is illustrated in FIG. 3A. A mixture of probes are synthesized containing two domains, a fixed sequence recognition domain, typically comprised of only one or a few sequences, and a randomized domain, comprising the full set (or some subset) of all possible sequences. The fixed sequence of the probe is used to target hybridization of the probe to a single site within a particular target nucleic acid. This target site is typically invariant. The sequence adjacent to the invariant sequence is variable and, depending on the particular target, can have any one of the total combinations of sequence. In order to probe for all possibilities it is necessary to synthesize probes containing all the possible secondary domain sequence combinations. If the second probe region is four bases in length, then 256 different probes need to be synthesized. If the second probe region is five bases in length, then 1024 different probes need to be synthesized. Six bases required 4096, and so on. The probes can be synthesized individually, each possessing a unique combination of mass labels as a releasable mass signature. Alternatively, the probes can be synthesized with unique mass signatures using a combinatorial synthesis method of the type described previously. In particular embodiments regarding diagnostic probes, it may be desirable to generate only a small number of probes, for example less than 20.

The two domain probes are useful for identifying the end sequence within clone inserts. As an example, the fixed sequence domain would hybridize to the cloning vector sequence immediately adjacent to the insert sequence. The variable sequence is then available to hybridize to the cloned insert. Only the probe that is complimentary to the cloned insert sequence adjacent to the cloning vector sequence will form a perfect hybrid. The remaining two domain probes will not. Detection of the mass label signature for the probe that has hybridized using one of the methods described will identify the probe sequence and the clone insert sequence. Other applications include targeting hypervariable sequence regions or mutation/polymorphism analysis at targeted sites. In all cases the fixed sequence of the probe directs the probe to a unique region within the target, essentially anchoring where the variable region will probe.

In order to increase the level of discrimination and extend the read length for the short sequence read it is possible to use an enzyme, such as polymerase or ligase, to add a single nucleotide or oligonucleotide to the end of the variable region of the anchored probe, optionally including mass labels on the added nucleotide or oligonucleotide that can identify the sequence for these additions. Addition of bases by either enzyme places stricter requirements on the variable region being a perfect hybrid to enable enzymatic action. Examples of how these probe additions work are shown in FIG. 3B. Note that for polymerase the addition needs to be to the 3' end of the probe while ligation can occur at either the 3' end of 5' end. As with the variable region within the probe increasing size of the addition will necessitate a larger and larger pool to represent all possible sequences. Oligonucleotide additions don't necessarily need to be entirely variable. There may be cases where the variable region will contain an invariant region. Such extensions will increase the thermodynamic stability of the oligonucleotide addition and allow ligation to occur at higher temperatures. It is also possible to envision cases where invariant nucleotide sequence would be intermingled with the variable sequences described.

Combinatorial libraries may also be used to detect short sequences. In cases where the full set of probes are used, though, it may not be possible to uniquely identify the sequences of the probes if more than one probe is present after hybridization at a significant level. One possible approach to limiting the number of probes that hybridize to a particular target is attaching a unique anchoring sequence to the probe set limiting the locations where the probe can hybridize. This anchoring is similar to that previously described for analysis of short sequence reads. As previously described, it is also possible that extra bases could be added to the end of the probe to lengthen the sequence determination and improve discrimination, if necessary.

A specific example of using the anchored, combinatorially synthesized probes is shown in FIG. 4B. In the case of screening genomic or cDNA clone inserts the anchored, invariant sequence is used to hybridize to the known vector sequence immediately adjacent to the insert or in the specific case of a cDNA insert to the poly A/T region of the insert.

While the preferred embodiment for these assays is to use nonvolatile releasable mass labels or involatile releasable mass labels, other types of labels can be used as well, such as isotopic mass labels, volatile mass labels (including electrophores), fluorescent labels, and chemiluminescent labels.

L. Targeted Cleavage Mismatch Detection

It is of interest to detect the presence of a mutation within a given sequence in cases where one does not have prior knowledge of exactly where the particular mutation might occur. Oligonucleotide probes may be used for hybridization to a target DNA containing a single mutation within a region of interest, leading to the formation of a mismatch. In one embodiment of the invention, enzymatically synthesized mass-labeled probes blocked from double-strand-specific enzymatic digestion at the 3' end are used. The 3' ends of the probes can be blocked by chemical modification or enzymatically. For example, blocking can be achieved by making the 3' terminus inaccessible to enzymatic digestion. After hybridization of the probe to the target sequence, treatment with a mismatch specific chemical or enzymatic cleaving reagent would cleave the hybridized pair at the mismatch site. Representative cleaving regents include KMNO$_4$ and T4 endonuclease VII. Subsequent treatment of the cleaved pair with a double-strand-specific 3'-5' exonuclease, such as exonuclease III, would lead to digestion of probe from the cleavage site to the 5' labeled end, thereby releasing the mass label. This method is illustrated in FIG. 5A and FIG. 5B. As an alternative, the polarity of the system can be reversed by placement of the mass label at the 3' end of the probe and by using a double-strand-specific 5'-3' exonuclease, such as T7 gene 6 exonuclease.

Another example of mismatch detection involves the amplification of heterozygous target DNA using two different mass-labeled probes. The difference can be a single base mutation, for example A:T to G:C. Four products are produced by the PCR™ reaction, two fully homogenous products representing the original sequences, while the other two products contain a mismatch at the mutation site. Treatment with terminal transferase adds long 3' overhangs to all of the products. Chemical or enzymatic mismatch specific cleavage is used, affecting only the two heterogeneous pairs. Exonuclease III digestion also affects only the cleaved heterogeneous pairs, releasing the mass labels without digesting the sequences blocked by the 3' overhangs. This method is shown in FIG. 5C and FIG. 5D. These mismatch methods could also be combined with other labeling methods such as fluorescent tags or radiolabels.

While the preferred embodiment for these assays is to use nonvolatile releasable mass labels or involatile releasable mass labels, other types of labels can be used as well, such as isotopic mass labels, volatile mass labels (including electrophores), fluorescent labels, and chemiluminescent labels.

M. Highly Multiplexed Probe Screening Assays

A number of novel applications become possible with multiplexed, mass-labeled probes where the preferred mode is to be able to screen a large number of targets simultaneously. Multiplexed applications include multiple pathogen diagnostics, multigene genetic polymorphism screening, SNP genotyping, clone and gene mapping, and gene expression analysis.

Highly multiplexed analysis by hybridization can be categorized into one of three approaches: (A) hybridization of a library of probes with known sequence against a library of targets of unknown sequence, (B) hybridization of a library of probes with unknown sequence against a library of targets of know sequence, and (C) hybridization of a library of probes with unknown sequence against a library of targets of unknown sequence.

Approach (A) is beneficial for applications such as diagnostics, genotyping, expression analysis and probe mapping where it has been predetermined what sequences are to be screened. Many of the methods described above may be used in approach (A). Combinatorially synthesized probes can be used with approach (A) where the sequences of the probes (and target to which the probe is hybridized) are postdetermined, i.e. probe and then determine the sequence of which probe has hybridized. The limits as previously described for combinatorial probes apply. Use of repertoire sets of mass labeled probes, as opposed to combinatorial probes, can be used in multiplexed mixtures to detect the presence of short sequences for purposes of sequencing by hybridization or producing a probe signature for a particular target sequence.

Approach (B) provides a path for a number of applications where a library of different known DNA sequences, such as oligonucleotides, PCR™ products, RNA transcripts or DNA clones, have been arranged and are available for partitioning the unknown probe set. These methods often, but not always, include the use of solid phase arrays to physically partition the known sequences prior to probing. Applications include competitive hybridization for differential expression analysis and fast mapping of genes, subclones or short sequence tags (SSTs) against a master genomic clone library, multiplexed infectious agent detection or any other set of samples that need to be probed in a multiplexed fashion.

Approach (C) is useful in cases where it is not necessary to know sequence but only to determine trends. As an example, one might want to determine the degree of homology or complementarity between two or more species or two or more expressed gene sets. Random or semirandom probes against random or semi random target can provide percentage values for homology. In these cases probes or targets that exhibit different properties, e.g., fall into the nonhomologous category, may be taken on for further analysis to determine their sequences. Such a method could be used for gene discovery.

A practical example employing these approaches is in measuring gene expression profiles. The most basic way to measure a gene expression profile is statistically, to count the number of message RNAs (mRNAs) produced for each particular gene within a particular cellular sample. The more mRNA copies of a particular gene, the higher its level of expression. The approach commonly taken is to separate out a representative number of mRNAs through a process of copying the mRNA to complementary DNA (cDNA), and then growing up the individual clone colonies of each cDNA on culture plates. Typically, cDNAs are cloned by insertion into either a plasmid or a phagemid cloning vector, and then transformed into bacterial or encapsidated into phage respectively. Each clone represents an individual mRNA derived from the total population. The set of clones comprises a gene expression library.

currently, the common approach used in genomic research to screen the clones and to identify which mRNA/gene correlates to which clone is to sequence the DNA: A portion of each cDNA clone sequence is read creating an expressed sequence tag (EST) that uniquely identifies the message/gene sequence. Identity is made by comparing the EST to genomic data bases containing previously identified gene sequences. In several years, all human EST sequences will be placed into existing public and private databases.

When screening a particular clone library, possibly a library that includes 10.000 clones, any particular EST may appear multiple times. The more times a particular EST appears, the higher the expression level for the gene correlating to the EST. The more clones that can be read, the more statistically representative the EST data will be to actual expression. Screening larger numbers of clones also makes it more likely that genes expressed at low levels will be identified.

With this in mind, it would be ideal to be able to screen 100,000 or more clones per library. However, this level is costly and impractical using existing sequencing technology. Typical sequencing screens analyze 500-10,000 samples at a cost of $5,000 to $100,000. New DNA sequencing technology will be, able to lower this cost somewhat.

The mass-labeled hybridization probes of the present invention could simplify and lower the cost of gene expression analysis. The probe approach primarily utilizes knowledge of the genes to be analyzed. Since the vast majority of gene sequences will be known within a few years, it is not necessary to use a de novo technique. It is also possible to detect previously unknown genes with these hybridization procedures. Complete identification of new genes may require a separate DNA sequencing analysis, subsequent to a hybridization assay, to determine the sequence of any of these newly discovered genes.

As is the case for the sequencing-based approach to gene expression analysis, the hybridization approaches of the current invention will usually involve converting the mRNA population to cDNA, transforming the cDNA into bacteria and growing bacterial colonies on culture plates and screening bacterially derived plasmids. Following the process of approach (A), hybridization of a library of known probes against a library of unknown targets (the cDNA clones), the clones to be screened can be spotted in a regularly spaced array or grid on a surface such as a nylon filter, glass, silicon or gold. The typical process involving bacteria colonies involves lysing the bacteria cells on the grid and fixing the DNA to the surface. The grid of cDNAs represent the library of tens to hundreds of thousands of expressed messages to be probed.

In conventional methods, a grid can be probed with only one single probe sequence at a time, typically being radioactively labeled as shown in FIG. 9A. Following the gridding of the unknown cDNAs, the library cDNA array is wetted with a solution containing the labeled nucleic acid probe. The grid-probe solution is incubated to allow the probe to hybridize its complement at one or more positions within the grid. Following hybridization, the grid is imaged in order to locate the probe-hybridization positions. In order to use multiple probes representing multiple genes, the grid needs to be replicated and a different grid is used for each probe. Using fluorescent labels, four different chromophores can be multiplexed within a sample and individually detected with the aid of software deconvolution of the fluorescence emission spectrum as shown in FIG. 9B. However, the practical upper limit for fluorescence multiplexing is likely to be around 10 different labels due to the broad overlapping spectrum produced by existing fluorescent chromophores.

Use of releasable, nonvolatile mass labels to uniquely label individual probes provides a means of using a highly multiplexed set of probes to simultaneously screen a single grid of unknowns. The nucleic acid probes can be synthesized using individual cDNAs with known sequence as templates. In all cases the probes may use combinations of mass labels or single mass labels. Following synthesis and mass-labeling, the different probes can be combined and used to probe a single grid in a multiplex fashion. The probing procedure is identical to that used for a single radioactively labeled probe until the imaging step is reached. Instead of using a phosphorimager or x-ray film, the grid is scanned within the mass spectrometer after release of the labels, pausing briefly at each position to detect the mass label signal that may be present.

The number of probes used is only limited to the number of probes one is willing to make and to the number one is interested in. As an example, one may be interested in a set of 1000 genes that may play an important role in a particular disease or one may wish to look at 50.000 different genes. In either case the probes may be individually synthesized or produced in combinations in microliter plates using liquid handling robotics. Likely approaches include the performance of T7 RNA polymerase transcriptions of plasmids containing known cDNA inserts using mass-labeled nucleoside triphosphates to produce mass-labeled RNA probes, PCR™ reactions amplifying known cDNA inserts using either mass-labeled nucleoside triphosphates or mass-labeled DNA primers to produce mass-labeled DNA probes or chemically synthesized mass-labeled oligonucleotide probes. Examples of enzymatic probe synthesis are provided in FIG. 4C and FIG. 4D. Within each synthesis reaction a different single or unique combination of mass-labeled nucleoside triphosphates are added which thereby incorporate a unique mass signature within each newly synthesized probe. In the cases of mass-labeled oligonucleotide probes it is also possible to use chemically synthesized combinatorial probes. Following synthesis, the probe set is mixed together to create a master probe mix. A number of mater probe mixes can be prepared to perform multiplexing if desired, where each cDNA of each master probe mix has a unique combination mass label signature. The probe set or sets can then be used to probe a large number of different unknown complementary DNA gridded libraries as shown in FIG. 9C. Different libraries can be prepared from a variety of samples, for example exposed to different stressor conditions and/or different est pharmaceuticals, possibly with time as an additional variable.

An alternative method for gene expression analysis follows the process of approach (B), hybridization of a library of unkndwn probes against a library of known targets sequences. Rather than uniqUely labeling known gene probes to hybridize against unknown cDNAs, one can label libraries of unknown cDNAs and hybridize against known unlabeled gene probes arrayed on a grid. This method has been described for two libraries using fluorescently labeled unknown cDNA mixtures (Schena et al., 1995; incorporated herein by reference) as shown in FIG. 10A. In the fluorescent case, first strand cDNA is prepared form two separate cellular samples. Synthesis of the first mixture of cDNAs is performed in presence of one particular fluorescent nucleotide, and the synthesis of the second mixture in the presence of a different fluorescent nucleotide. The mixture of cDNAs, which reflect the relative abundance of different mRNAs from each sample, are then mixed and allowed to competitively hybridize to a gridded array of known genes present on a solid phase surface. After the cDNAs have hybridized to the grid, and unbound labeled cDNAs are washed away, the relative fluorescence intensity for the two dyes is measured at each position in the gridded array. If the fluorescence intensity for each dye is equivalent then the corresponding mRNAs from each sample were expressed at a similar level. If the fluorescence intensity is stronger for one dye than the other at a particular position/gene in the gridded array, then that gene was expressed at a higher level in the sample whose fluorescence was stronger.

By utilizing the mass labeling methods to prepare the cDNAs, rather than fluorescence, it is possible to prepare and simultaneously hybridize cDNAs from many different cellular sources to the gridded array of known genes. Instead of only two or three cDNA pools being compared simultaneously, the use of mass labels makes it possible to compare tens if not hundreds of cDNA pools simultaneously as shown in FIG. 10B. The mass labels can be released by any of the appropriate release mechanisms described and the grid can be scanned for the mass label signal. The intensity of the mass signals at a given grid position will be proportional to the level of mRNA in the original sample that corresponds to the detected cDNA on the grid. The relative ratios of the competing mass labels are determined providing information about the differences in gene expression between all of the different samples for all of the genes present on the gridded array.

This same multiplexed mass-labeled probe methodology can be used to quickly map genes to large genomic libraries. Gridded libraries of P1, PAC/BAC and YAC clones can be prepared in the same manner as cDNA filters. Multiple label studies provide a means for quickly mapping genes and identifying gene clusters. Probes generated from particular clone inserts or gene sequences are used to screen libraries of genomic or cDNA clones. Hybridization events indicate an overlap of insert sequence in the genomic case and the presence of a gene in the cDNA case. These libraries can also be used for intergenomic probing, e.g., probing a *C. elegans* library with human gene probes, and visa versa.

The technology for probing with and detecting mass labels within gridded arrays can also be applied to other solid phase systems where DNA probes are utilized, specifically Northern and Southern assays. In these two methods the initial phase is to run a polyacrylamide gel and then to transfer the DNA to a nylon membrane using a blotting procedure (Sambrook et al., 1989). As with other procedures described above, mass-labeled nucleic acid probes can be prepared to hybridize to the filters. In another embodiment mixtures of single or combinations of mass labels can be used in an effort to multiplex the detection. A scan of the filter after hybridization and washing within the mass spectrometer provides the means to detect, and where necessary quantify, the amount of mass label present in a particular location.

An additional embodiment of the technology is the use of mass labeled protein probes, in the form of antibodies, for hybridization against one and two-dimensional protein gels. One skilled in the art can also envision other combinations of mass labeled probe molecules hybridized against targets bound to a solid phase matrix. In all cases the mass label is released and either the solid phase surface analyzed using a scanning mass spectrometer, or a transfer to another surface takes place before mass analysis.

Attachment of the genetic target or other target to a filter or other form of grid is not necessary as part of the broadest embodiments of the invention. For example, a mass-labeled probe set may be directly hybridized to DNA or RNA targets in solution. In order to discriminate between the probes that hybridize and the probes that do not, one of two possible events needs to occur. Either the mass labels on hybridized probes need to be enzymatically released using a double-strand-specific nuclease, such as exonuclease III, lambda exonuclease, T7 gene 6 exonuclease or a restriction endonuclease, or some partitioning event needs to occur wherein unhybridized probes are separated from hybridized probes. One of skill in the art can envision several means for partitioning other than pre-binding of the target to a solid phase array as described in the methods above, such as hybridized probe extension by a polymerase using biotinylated nucleotides, or coupling the mass labeled probe to a biotinylated probe as part of an amplification event, such as PCR™ or LCR.

For both the nuclease case and the partitioning case, an amplification event can be used to produce a significant amount of mass label. Mass labels attached to a probe hybridizing downstream from one of the PCR™ primers can be released during PCR™ amplification using the nick translation 5'-3' exonuclease activity of the thermostable polymerase. Mass labels within primers can be released using a 5'3' exonuclease such as T7 gene 6 exonuclease after amplification. In embodiments where a mass labeled primer is coupled to a biotinylated primer during amplification, or biotin is incorporated through the use of biotinylated nucleotides, and the product is partitioned away from the unincorporated primers, it is possible to use nonspecific cleavage, such as chemical cleavage methods, to the release of the mass label.

In another embodiments, hybridization-specific nuclease digestion can also be used to cleave a probe containing both biotin and mass label, in an assay where solid-phase-bound steptavidin is used to remove uncleaved mass labels. Examples of such cleavage involve the use of a double-strand-specific nuclease such as those described above. Restriction endonucleases may be used to cleave a probe that contains a restriction site in the center and a mass label and biotin at opposing ends of the probe. Another example, where RNA is used as a probe, involves double-strand-specific cleavage using RNase H.

In another exemplary method for the detection of an amplified single-stranded target such as that produced by T7 RNA polymerase transcription, a double-stranded probe is prepared with the mass label being attached to the strand that is homologous in sequence to the target strand. The mass-labeled strand is then displaced by a competitive hybridization with target and the mass label is released by a single-strand specific exonuclease such as exonuclease VII, Mung Bean nuclease or nuclease S1. An alternate method would employ the use of single-strand specific chemical cleavage reagent to release the mass label from a chemically modified probe. Examples of chemical modifications that would provide single-strand specific release of mass label include cleavage of a ribonucleotide base by transesterification, a phosphoramidate cleavable by acid, and a 5'-P-S phosphorothioate cleavable by silver nitrate as described in Example 9.

PCR™ can also be combined with the use of a mass labeled primer and a restriction enzyme to enable release of a mass label only if amplification occurs. In this embodiment the mass labeled PCR™ primer contains the sequence for a restriction site that becomes double-stranded only as part of the amplification process. Once the site is double stranded, it is recognized by the restriction enzyme and cleaved. The cleavage event releases the mass label from bulk of the primer and PCR™ product allowing it to be uniquely detected.

An embodiment of the invention where mass-labeled probes can be used to measure mRNA levels in solution is shown schematically in FIG. 14. A series of gene-specific, mass-labeled probes (1-100 per study) are added to the mRNA pool (or more likely, first-strand cDNAs derived from the mRNA pool) and allowed to hybridize. Each gene-specific probe carries a unique mass label, and possibly multiple copies of that label to increase sensitivity. The hybridized mixture is treated with a double-strand-specific-exonuclease that releases the mass labels for the portion of the probe population that was hybridized to target genes. Only if the mRNA from a gene of interest is present will the corresponding mass label be released and detected. In addition, the signal intensity for the particular mass label will be proportional to the relative abundance of the particular mRNA within the pool. Comparisons of the relative intensities for the different mass labels reflect the relative mRNA expression levels. The relative gene expression pattern for as many as 38,400 genes could be probed for in a single 384 microliter plate if 100 different probes per will are used. Conversely, a set of 100 genes be examined for 384 different samples in a single microliter plate experiment.

There are examples where the mass spectrometric sensitivity levels may be found to be insufficient to directly monitor the mRNA levels, e.g., due to small numbers of cells as a result of poor cell growth, or in animal model samples derived from very small tissue biopsies. For such samples, it may be necessary to incorporate message amplification schemes into the methodology.

As described earlier, the use of nucleases that digest mass-labeled nucleic acid probes when they are hybridized to a target nucleic acid affords the possibility for linear amplification of signal. In cases where the target DNA is single stranded and significantly longer than the probe being used, it is possible to selectively digest only the probe. Digestion of the oligonucleotide probe makes the target strand repeatedly available for multiple rounds of hybridization and digestion. This type of amplification can readily achieve 2 to 3 orders magnitude of amplification.

Because any given study may only monitor a relatively small number of genes, e.g., 20 to 100, it may be possible to use one or a few multiplexed PCR™ reactions to amplify only the targets associated with the probe set. The use of PCR™ or other amplification methods may require the development of additional controls so as to reduce the influence of amplification artifacts. The multiplexing ability of mass-labeled probes makes it easy to include one or more controls. The use of redundant or semi-redundant primers, such as those used in differential display techniques, may also provide an effective amplification route. In all cases where a polymerase is used for amplification, such as Taq DNA polymerase, the 5' to 3' exonuclease activity can be used to digest the probe while amplification continues (Holland et al., 1991).

All of the solution phase methods, including methods that utilize partitioning, described above may be utilized as a means for coupling the release of a mass label to the presence of a particular mRNA sequence. Other methods that may be used in amplification, of the message population include ligase chain reaction, in vitro transcription of the cDNA population, and variants of methods for producing cDNA libraries, such as single-well polyclonal cDNA plasmid growth.

As the full gene set of an organism becomes available, it is conceivable to prepare beforehand the complete set of mass-labeled probes for gene expression analysis. With probes being enzymatically synthesized, a large stock of these probes can be made at a relatively inexpensive cost in less than a week of effort. It is also possible to quickly make a repertoire of mass-labeled probes through chemical means.

While the preferred embodiment for the assays described herein is to use nonvolatile releasable mass labels or involatile releasable mass labels, other types of labels can be used as well, such as isotopic mass labels, volatile mass labels (including electrophores), fluorescent labels, and chemiluminescent labels.

N. Multiplexed Mass Label Substrates in Affinity Assays.

The methods disclosed herein may also be employed in indirect schemes for identifying the presence of one or more target biomolecules. Indirect schemes, such as enzyme-linked immunosorbent assays (ELISAs), provide a method for utilizing substrate conversion to a product molecule via enzymatic turnover of the substrate. Enzymatic catalysis of a substrate leads to the linear amplification of the product's signal.

In an ELISA the target molecules, generally bound to the solid phase, are recognized by an antibody which noncovalently binds to the target. The recognition antibody is conjugated to an enzyme used to catalyze substrate conversion to product. Traditional ELISA techniques utilize small organic molecule substrates that when converted to product by an enzyme, such as alkaline phosphatase, horse-radish peroxidase, or urease, yield a molecule with changed optical qualities, e.g., the solution becomes colored or the product possesses strong fluorescence. In addition, the conversion of substrate to product often produces a change in mass, thus the product may act as a mass label that may be detected by mass spectrometry. The amount of product may be quantified either absolutely or relative to the substrate used, with knowledge of enzyme turnover rates and reaction conditions, and used to calculate the amount of a target molecule present in the assay.

Methods for traditional ELISA assays are well established (see Current Protocols in Molecular Biology Vol. 2, Chapter 11, incorporated as a reference herein). Multiple protocols exist, which include indirect, direct competitive, antibody-sandwich, double antibody-sandwich, direct cellular, and indirect cellular assays. The mass label modification envisioned in this application would be designed to measure unknown quantities of target biomolecules by adaptation of the traditional ELISA methods. In this modification, target biomolecules are covalently or noncovalently bound to a surface, such as on a bead or a plastic dish, either directly or through a small "capturing" molecule (ligand) or a protein (such as an antibody). The target biomolecule could also be a component of a cell that could be bound to the surface of the vessel. The solid-phase target biomolecules are incubated with a target recognition molecule (antibody, ligand, oligonucleotide, etc.) that has a specific affinity for the target biomolecule. This target recognition molecule is conjugated to an enzyme. Four multiplexed assays each target recognition molecule much be covalently linked to an enzyme with a unique catalytic activity for differentiation of the different targets (typical of the "direct" assay protocols). These conjugated target recognition molecules are allowed to bind to the substrate; unbound molecules are removed by washing, then the enzyme substrates are added under conditions in which bound enzyme reacts with its substrate to release a product with a unique mass that is detectable using mass spectrometry.

"Capture antibodies" with high specific binding affinity for the antigens may be needed for soluble antigens. Methods for preparation of specific antibodies for either capture or quantitation of antigens are well established in the literature. Methods for conjugating enzymes to antibodies are also well established and may include crosslinking agents such as glutaraldehyde or conjugation via perioxidate oxidation. Purified DNA restriction enzymes are commercially available. New enzymes with unique catalytic activity may also be engineered using established molecular procedures.

The ease of detection of a multiplex of mass labels offers the opportunity for the performance of a multiplex of immuno assays simultaneously within a single solution. Different enzymes, conjugated to antibodies or other target recognition molecules, used in combination with a set of enzyme-specific substrates may be used to yield enzymatic products that are unique in mass and therefore uniquely detectable and quantitatable by mass spectrometry.

In addition to multiplexing an unrelated set of enzymes and substrates, classes of enzymes that modify a class of substrates may also be multiplexed: For example, classes of enzymes all recognizing the same substrate but modifying it in different ways may be employed as may enzymes which recognize and modify particular chemically-related substrates, where the variations in structure alter the specificity of particular enzymes for the particular substrate.

A class of enzymes all recognizing the same or a few substrates is proteases. Proteases recognize different amino acids or amino acid sequence motifs and cleave the amide linkage yielding two or more fragments. Examples of proteases and their specificities include: trypsin, which cleaves at the C-terminal side of both arginine and lysine residues; thrombin, which cleaves at arginine; Glu-C, which cleaves at the C-terminal side of glutamic acid residues; Lys-C, which cleaves at the C-terminal side of lysines; and Asp-N, which cleaves at the N-terminal side of aspartic acid residues. Small polypeptides containing specific amino acids and/or amino acid sequence motifs may be used as substrates for proteolytic digestion. The use of one or a few polypeptides that are recognized and cleaved differently by different proteases sets a situation where there is a competition for substrate. The use of competitive substrates, and measurements of the relative ratios of different products derived from the same substrate, may provide a more accurate measure of the relative quantities of different target biomolecules.

One potential problem with the use of proteases is their possible digestion of antibodies and other proteins required for the bioassay. This problem may be overcome through a variety of means including, careful selection of proteases, selective chemical modification to block proteolysis, and use of protease inhibitors including those that can be competitively displaced by the reaction substrates. Alternatively, proteases may be used on other nonprotein-based assays such as probing for nucleic acid using oligonucleotide probes conjugated to the proteases. Other classes of enzymes that may be used instead of proteases include kinases which phosphorylate their substrates and nucleases:

Ribonucleases and deoxyribonucleases have varying specificity. Endonucleases such as RNas T1, Rnase U2, and Rnase CL3, target G, A, and C nucleotides, respectively. In a similar manner to the use of small polypeptides as substrate for proteases, small oligonucleotides may be used with nucleases. Nuclease resistant nucleotides, such as phosphorothioates, methylphosphonates, boranophosphates, and peptide nucleic acids can be incorporated into the substrates to direct the specificity of the different nucleases toward yielding unique products. Unlike peptides which can be simply and easily detected by mass spectrometry it may be preferred to modify the oligonucleotides with the addition of polypeptides or other molecules to improve and ease analysis in the mass spectrometer.

Another class of enzymes is restriction endonucleases. Use of restriction enzymes falls under the second case described above, where substrates may be chemically related but variations in structure alter their specificity as far as to which enzyme in the class will recognize and modify it. In this case the structural alterations are changes in the sequence of the substrates. The substrates themselves are small double-stranded oligonucleotides which contain one or more restriction endonuclease recognition and cleavage sites. Similar to the use of nucleases described above, and as is described in other sections of this invention, it is preferred to modify the oligonucleotides with the addition of polypeptides or other molecules to improve and ease analysis and selectivity in the mass spectrometer. Because many restriction endonucleases recognize palindromic sequences it is also possible to increase the level of signal two-fold by the use of palindromic oligonucleotide substrates which form dimers. Each cleavage event forms two identical products. Longer concatamers may also be produced creating larger, multi-mass-labeled substrate.

Antibodies are not the only possible target-recognition molecule that may be used in these assays. Polypeptides derived from methods such as phage display with target binding properties, as well as a variety of native proteins that demonstrate some binding activity of interest, may be used instead. Targets may also be something other than proteins and can include a variety of biologically relevant small molecules, including enzyme cofactors, hormones, neurotransmitters, and other biopolymers including polysaccharides and most importantly nucleic acids. Nucleic acid hybridization interactions may be used where both the target and the recognition molecule are comprised of nucleic acids. Nucleic acids and other nonpeptide recognition molecules may be bound to the enzyme involved in substrate conversion covalently via a variety of linkage chemistries, some of which have been described here in the XXX section, or noncovalently through a biotin/avidin linkage where the avidin is conjugated to the substrate conversion enzyme. One skilled in the art can identify other linking methods.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Peptide-Labeled Oligonucleotides
A. Preparation of Peptide-Linked Nucleoside 5' Triphosphates Preparation of peptide-linked nucleoside 5'-triphosphates involves synthesis and coupling of allylamino-substituted dNTPs. An example is shown in FIG. 6A. 5-(3-aminoallyl)-2'-deoxyuridine 5'-triphosphate (c) was prepared according to the procedure of Langer et al., 1981). Treatment of dUTP (a) with mercuric acetate at pH 5-7 provides the 5-mercurated derivative (b). Allylation in the presence of a palladium catalyst then provided c, which was coupled to the NHS-ester (d) of a suitably protected peptide (lysine and N-terminal amines blocked with FMOC groups). Base deprotection of the peptide resulted in formation of the desired product (e). Alternatively, the allylamino-nucleotide (c) was treated sequentially with the hetero-bifunctional crosslinking reagent mal-sac-HNSA (Bachem Bioscience Inc., King of Prussia, Pa.) and an N-terminal cysteine peptide to give the conjugate (f).

B. Preparation of Peptide-Labeled Phosphoramidites

Peptide nucleoside phosphoramidite conjugates were prepared from 5'-protected allylaminonucleosides as shown in FIG. 6B. Selective dimethoxytritylation of uridine (h) provided the 5'-DMT ether (i), that was allylated via the mercurinucleoside with palladium catalyst (Dale et al., 1973; Langer et al., 1981). Treatment of the NHS-ester of a suitably protected peptide and conversion of the conjugate to the phosphoramidite (Sproat et al., 1987) provided the desired compound (k).

C. Synthesis of a 5' Labeled Oligonucleotide-Peptide Conjugate

Oligonucleotide g (FIG. 6C) (SEQ ID NO:10) was prepared using standard solid-phase phosphoramidite chemistry. The 5'-amino-modification through a disulfide linkage was achieved by sequential addition of Thio-Modifier C6 S—S and Amino-Modifier C6 dT (Glen Research Inc., Sterling, Va.) to the 5'-end. The oligonucleotide was coupled to the heterobifunctional reagent mal-sac-HNSA (Bachem California Inc., Torrance, Calif.) through the terminal primary amino group, purified by exclusion chromatography, and covalently coupled to a peptide with the sequence CGR GSG K through the N-terminal cysteine thiol. The conjugate was purified by ion-exchange chromatography, and analyzed by MALDI-TOF mass spectrometry (FIG. 7X). The peck at m/z 8401 in FIG. 7X corresponds to the desired conjugate.

D. Synthesis of a 3' Labeled Oligonucleotide

A 3' phosphorylated oligonucleotide with the sequence 5'-TGAGGTGCGTGTTTGTGCCTGTp-3' (SEQ ID NO: 1) was synthesized by standard phosphoramidite chemistry. A MALDI mass spectrum of the unconjugated oligonucleotide is shown in FIG. 7A. The 3'-terminal T residue of the oligonucleotide was modified with a primary amino-group that was incorporated during the synthesis as the modified phosphoramidite (C6-amino modifier, Glen Research Inc., Sterling, Va.). The oligonucleotide was coupled through the active amino group to a peptide using the hetero-bifunctional coupling reagent mal-sac-HNSA (Bachem Inc., Torrance, Calif.). The sequence of the peptide used for coupling to the oligonucleotide was CGYGPKKKRKVGG (SEQ ID NO: 2) (Sigma Chemical Co., St. Louis, Mo.). The reaction to couple the peptide to the oligonucleotide occurs at the reactive thiol group on the N-terminal cysteine residue. After the coupling reaction, which is carried out according to standard procedure, the crude coupled product is purified by reversed phase HPLC. Fractions containing the desired coupled product were identified by MALDI-MS, and were combined and evaporated to dryness. The dried material was dissolved in a small amount of water and the concentration determined by UV absorbance at 260 nm. A MALDI mass spectrum of the oligonucleotide-peptide conjugate is shown in FIG. 7B. The major peak at m/z 8622.8 agrees well with desired product, while the peck at 7051.7 is due to a residual amount of unreacted oligonucleotide (ca. 20%).

E. Synthesis of an Internally-Labeled Oligonucleotide-Peptide Conjugate

An oligonucleotide of the sequence 5'-GGT TTA CAT GTT CCA A(aminoT)A TGA T-3' (SEQ ID NO: 11) was prepared by standard phosphoramidite chemistry using Amino-Modifier C6 dT (Glen Research Inc., Sterling, Va.) to incorporate the internal amino-modification. The oligonucleotide was coupled to the hetrobifunctional reagent mal-sac-HNSA (Bachem California Inc., Torrance, Calif.) through the internal primary amino group, purified by exclusion chromatography, and covalently coupled to a peptide with the sequence CGT RGS GKG TG through the N-terminal cysteine thiol. The conjugate was purified by ion-exchange chromatography, and analyzed by MALDI-TOF mass spectrometry (FIG. 7X). The peak at m/z 8075 in FIG. 7X corresponds to the desired conjugate.

Example 2

Detection of a Specific Target Sequence

As an example of the utility of the oligonucleotide-peptide conjugate as a probe in a hybridization study, a model system was designed using a synthetic complementary strand as target DNA. A 42-mer was synthesized as a model target, with the sequence 5'-CTCCCAGGACAGGCACAAACACG-CACCTCAAAGCTGTTCCGT-3' (SEQ ID NO: 3). Detection of the target was based on release of the peptide mass label (SEQ ID NO: 2) from the probe by a digestion with the 3'-5' double-strand-specific exonuclease III with analysis by MALDI-MS.

A mixture of 1 pmol of probe and 1 pmol of target in a 9 µL volume of 1× Exonuclease III buffer (66 mM Tris-HC1, pH 8.0; 5 mM DTT; 6.6 mM $MgCl_2$; 50 µg/mL BSA) was allowed to anneal by heating the solution for 2 minutes in a boiling water bath and then slowly cooling it to room temperature over the course of about 20 minutes. Exonuclease III (USB, Cleveland, Ohio) was diluted from its stock concentration of 17.5 U/µL in 1× buffer, and a 1 µL aliquot was added to the annealed target-probe solution. Four controls were included and run simultaneously with the test solution. Control sample a contained both target and probe but no exonuclease III, control sample B contained probe and Exonuclease III but no target, control sample C contained probe and Exonuclease III together with a random non-complementary 36-mer, and control sample D contained only Exonuclease III. The mixtures were allowed to incubate for 30 minutes at room temperature. A 1 µL aliquot of the solution was removed and added on top of a polycrystalline spot of 2.5-dihydroxybenzoic acid on a MALDI-MS sample plate. The resulting positive-ion mass spectra of the test and control samples A, B and C are shown in FIG. 8A, FIG. 8B, FIG. 8C, and FIG. 8D. Only the test sample in FIG. 8A showed a peak at 2045.3, the mass expected for the released peptide-nucleotide conjugate, demonstrating that in this model system the inventors were able to specifically detect the presence of the target sequence by a sensitive and rapid method.

Selective Enzymatic Cleavage of a Peptide.

Oxidized bovine insulin chain B (Sigma Chemical Company, St. Louis, Mo.) in Tris.HC1 (pH=7.8) was treated with Endoproteinase Glu-C (w/w ratio 20:1, Sigma Chemical Company, St. Louis, Mo.) at 37° C. for 2 hours, and examined by MALDI-TOF mass spectrometry. The analysis (FIG. XX) indicated that the insulin (SEQ ID NO: 12) was efficiently cleaved at the carboxyl, side of glutamyl residues into three fragments, m/z 1533 (FVNQHLC[$SO_3$H]GSHLVE) (SEQ ID NO: 13), m/z 1089 (RGFFYTPKA) (SEQ ID NO: 14), and m/z 919 (ALYLVC[$SO_3$H]GE) (SEQ ID NO: 15). The relative intensities of the three peaks in the mass spectrum reflect the number of basic (ionizable) functionalities in the three fragments. The largest molecular weight fragment contains two moderately basic histidine residues and is therefore only modestly visible in the spectrum. The middle fragment contains strongly basic lysine and arginine residues and therefore displays an intense peak. The smallest fragment has only the terminal amino-group available for protonation, and is therefore barely detectable in the spectrum.

Example 3

Detection of mRNA Using Mass-Labeled Primers and rtPCR™

A pair of PCR™ priers for the ribosomal protein L7 gene was synthesized by standard phosphoramidite chemistry with a modified amino-thymidine (Glen Research, Sterlin, Va.) incorporated near the 3'-end of each. The sequence of the forward primer was 5'-ATCTGAAGICAGTAAAT*GAAC-3' (SEQ ID NO: 4) and the sequence for the reverse primer was 5'-ATTTACCAGAGAT*CGAG-3' (SEQ ID NO: 5), where T* represents the amino-modified thymidine. Each primer was mass-labeled with a unique peptide by a standard coupling reaction between the amino group of the amino-modified thymidine and a sulfhydryl group on the peptide through the heterobifunctional linker mal-SAC-HNSA (Bachem Corp., Torrance, Calif.), and purified by ion-exchange HPLC. The peptide mass label used for the forward primer had the sequence CGYGPKKKRKVGG (SEQ ID NO: 2), and for the reverse primer the peptide was CKNLNKDKQVYRATHR (SEQ ID NO: 6).

A reverse transcription reaction was performed on 10 µg of total RNA isolated from a stable cancer cell line to generate first strand cDNA. The reaction was performed in a total volume of 20 µl and contained 0.5 mg of oligo $dT_{15}$ primer (SEQ ID NO: 9) and 25 units of AMV reverse transcriptase. A PCR™ reaction was performed on 1 µl of the first strand cDNA using 10 pmol each of the forward and reverse mass-labeled primers and 0.25 units of Taq DNA polymerase in a 10 µl reaction. The rtPCRT™ product was purified through a Microcon-30 ultrafiltration unit (Amicon, Inc., Beverly, Mass.) according to the manufacturer's directions. After collecting the DNA from the filter unit, it was evaporated to dryness in a vacuum centrifuge and resuspended in 3.5 µl $H_2O$.

A digestion reaction using the double-strand specific 5'-3' exonuclease of T7 gene 6 was then performed. To the 3.5 μl of purified PCR™ product was added o.5 μl of 10× buffer (660 mM Tris, pH 8, 6.6 mM $MgCl_2$) followed by 1 μl (5 units) of T7 gene 6 exonuclease (Amersham Inc.). A control digestion was performed at the same time and contained 5 units of enzyme, 5 pmol of free forward primer in an identical buffer. The digestion reactions were allowed to incubate at 37° C. for 60 minutes followed by a heat inactivation of the enzyme (85° C. for 15 minutes). A small portion of anion exchange resin (DEAE Sephadex A-25, Aldrich Chemical Co., Milwaukee, Wis.) was added to each digestion and a 1 μl portion of the supernatant was removed and analyzed by MALDI-TOF mass spectrometry (positive ions, 3.5-dihydroxy benzoic acid matrix). The resulting mass spectra of the digested PCR™ product and control are shown in FIG. 15A and FIG. 15B respectively.

Example 4

Detection of a Mixture of cDNA Plasmids

A mixture of 100 ng each of six and 50 ng of a seventh single-strand M13 plasmid clones, each containing unique inserts, was desalted and concentrated in a Microco-30 ultrafiltration unit according to the manufacturer's directions. The DNA, after collection, was evaporated to dryness and resuspended in 1 μl of $H_2O$. A mixture of seven mass-labeled probes containing 2.5 pmol each was added. Each probe was complementary to a portion of the insert for each clone in the mixture and was coupled to a unique peptide mass label. The probes were allowed to hybridize by heating the mixture to 95° C. for 30 seconds followed by a 1 minute incubation at 45° C. After cooling the mixture to 37° C., 0.35 units of Exonuclease III was added and the digestion was allowed to proceed for 60 minutes. The reaction was allowed to cool to room temperature and then a small portion of DEAE Sephadex A25 anion exchange resin (Aldrich Chemical Co., Milwaukee, Wis.) was added. A 1 μl portion of the supernatant was then removed and analyzed by MALDI-TOF mass spectrometry (positive ions, 2.5-dihydroxy benzoic acid marix). The resulting mass spectrum of the mixture of released mass labels is shown in FIG. 16.

Example 5

SNP Analysis with Mass-Labeled Primers and Biotinylated Dideoxyucleoside Triphosphates A primer ("Primer A") containing a chemically-releasable mass label is synthesized and purified according to the method described in Example 1C. Two synthetic template strands are also synthesized by standard solid phase synthesis techniques. The sequence of Primer A is 5'LTSS-GTGCT-CAAGAACTACATGG-3' (SEQ ID NO: 16) and the sequences for the template strands are 5'TACTACCAGTTC-CATGTAGTTCTTGAGCAC-3' (Template 1T) (SEQ ID NO: 17) and 5'-TACTCCAGTACCATGTAGTTCTTGAG-CAC-3' (Template 1A) (SEQ ID NO: 18), where LT indicates the mass label attached to an amino-modified thymidine, SS represents the chemically cleavable disulfide-containing group, and the boldface base designations in the template strands indicate the polymorphic sites adjacent to the 3'-end of the primer. The primer is mass-labeled with a synthetic peptide possessing the sequence CGRGSGK (SEQ ID NO: 19).

Two cycle-sequencing reactions are performed. Each reaction contains 2 pmol of mass-labeled Primer A, 100 fmol of either Template 1T or Template 1A, 200 pmol of Biotin-ddUTP (Boehringer-Mannheim, Inc.) and 2.4 units of the thermostable DNA polymerase AmpliTaq-FS (Perkin-Elmer Inc.) in a total volume of 20 μL. Both reactions are begun using typical hot-start conditions. The reactions are performed according to the following thermal cycling program: denaturing at 90° C. for 30 s, annealing at 50° C. for 10 s, extension at 65° C. for 10 s, for a total of 35 cycles. Upon completion, the sequencing reactions are purified by capturing the extended biotinylated products on streptavidin-coated magnetic beads. The beads are washed to remove unextended primer and then the mass label released by treatment of the bead-bound product with a mild reducing agent to cleave the disulfide bond and release the mass label into solution. A 1 μL portion of the supernatant is removed and analyzed by MALDI-TOF mass spectrometry (positive ions, 2,5-dihydroxy benzoic acid matrix). The resulting mass spectra of the reaction containing the correct template to extend with biotin-ddUTP and of the reaction containing the incorrect template are shown in FIG. 17A and FIG. 17B, respectively. Since signal can only be seen in the spectrum in FIG. 17A as expected for the proper nucleotide incorporation, these results demonstrate the possibility of performing an SNP analysis using a mass-labeled primer together with biotinylated dideoxynucleoside triphosphates.

Example 6

Multiplexed SNP Analysis with Mass-Labeled Primers and Biotinylated Dideoxynucleoside Triphosphates Two primers ("Primer B" and "Primer C") each containing a unique chemically-releasable mass label are synthesized and purified according to the method described in Example 1C. A synthetic template strand for each is also synthesized by standard solid phase synthesis techniques. The sequence of the Primer B is 5'-LTSS-TCGGAGTCAACGGATTTG-3' (SEQ ID NO: 20) and the sequence for the corresponding template strand is 5'-TCCAGTTCTCAAATCCGT-TGACTCCGA-3' ("Template 2T") (SEQ ID NO: 21). Primer C and its template strand ("Template 3T") have the sequences 5'-LTSS-GATGTCTGTATATGTTGCACTG-3' (SEQ ID NO: 22) and 5'-AAGTTGACTCTCAGTGCAACATATA-CAGACATC-3' (SEQ ID NO: 23), respectively, where IT, SS, and boldface have the same meanings as described in Example 5. Primer B is mass-labeled with the synthetic peptide CAGGRGGGKGGA (SEQ ID NO: 24) and Primer C with the synthetic peptide CASGRGSGKGSA (SEQ ID NO: 25).

A multiplexed cycle-sequencing reaction is performed with Primer A, Primer B, Primer C and each of the corresponding templates. The reaction contains 2 pmol of each mass-labeled primer, 100 fmol each of Template 1T, Template 2T and Template 3T, 200 pmol of Biotin-ddATP (Clonetech, Inc.) and 2.4 units of the thermostable DNA polymerase AmpliTaq-FS (Perkin-Elmer Inc.) in a total volume of 20 μL. The reaction is begun using typical hot-start conditions and is performed according to the following thermal cycling program: denaturing at 90° C. for 30 s, annealing at 50° C. for 10 s, extension at 65° C. for 10 s, for a total of 35 cycles. Upon completion, the sequencing reaction is purified by capturing the extended biotinylated products on streptavidin-coated magnetic beads. The beads are washed to remove unextended primer and then the mass labels released by treatment of the bead-bound products with a mild reducing agent to cleave the disulfide bonds and release the mass labels into solution. A 1 μL portion of the supernatant is removed and analyzed by MALDI-TOF mass spectrometry (positive ions, 2,5-dihydroxy benzoic acid matrix). The resulting mass spectrum showing signals for each of the expected mass-labels with peaks labeled as A, B and C referring to primers A, B and C respectively is shown in FIG. 18. This demonstrates the potential for performing multiplex SNP analyses utilizing mass-labeled primers.

Example 7

SNP Analysis with Mass-Labeled Primers and Biotinylated Nucleoside Triphosphates Plus Normal Dideoxynucleoside Triphosphates Two cycle-sequencing reactions are performed with primer a and one of either template 1T (SEQ ID NO: 17) or template 1A (SEQ ID NO: 18). Each reaction contains 2 pmol of mass-labeled primer and 100 fmol of template. The triphosphates in each reaction consist of 200 pmol each of Biotin-dCTP (Clonetech, Inc.), dATP and ddTTP. The reactions are performed with 2.4 units of the thermostable DNA polymerase AmpliTaq-FS (Perkin-Elmer Inc.) in a total volume of 20 mL. The reactions are begun using typical hot-start conditions and are performed according to the following thermal cycling program: denaturing at 90° C. for 30 s, annealing at 50° C. for 10 s, extension at 65° C. for 10 s, for a total of 35 cycles. Upon completion, the sequencing reactions are purified by capturing the extended biotinylated products on streptavidin-coated magnetic beads. The beads are washed to remove unextended primer and then the mass labels released by treatment of the bead-bound products with a mild reducing agent to cleave the disulfide bonds and release the mass labels into solution. A 1 mL portion of each supernatant is removed and analyzed by MALDI-TOF mass spectrometry (positive ions, 2.5-dihydroxy benzoic acid matrix). The resulting mass spectra for the reaction containing template 1T and the reaction containing template 1A are shown in FIG. 19A [XX3a] and FIG. 19B [XX3b), respectively.

Example 8

Mass Label Tagging of Degenerate Base Primers and the Identification of Sequence Variants by Extension with Biotinylated Dideoxynucleoside Triphosphates Two primers related to Primer a and differing only in the identity of the 3'-terminal base are synthesized and mass-labeled, according to the method described in Example 1C. The sequence of Primer D is 5'-LTSS-GTGCTCAAGAAC-TACATGA-3' (SEQ ID NO: 26) and the sequence of Primer E is 5'-LTSS-GTGCTCAAGAACTACATGT-3' (SEQ ID NO: 27), where LT and SS have the meanings described in Example 5. A synthetic template strand ("Template 4A") is also synthesized using standard solid phase synthesis techniques. The sequence of the template strand is 5'-TACTC-CAGTTACATGTAGTTCTTGAGCAC-3' (SEQ ID NO: 28), where the boldface indicates the base that varies from Template 1T. Primers D and E are mass-labeled with two unique synthetic peptide that differ from the peptide attached to Primer A. The peptide attached to Primer D is CAG-GRGGGKGGA (SEQ ID NO: 29), while the peptide attached to Primer E is CASGRGSGKGSA (SEQ ID NO: 30).

Two cycle-sequencing reactions are performed. Each reaction contains 2 pmol each of mass-labeled Primer A, Primer D, and Primer E, 100 fmol of either Template 1T or Template 4A, 200 pmol of Biotin-ddATP (Clonetech, Inc.) and 2.4 units f the thermostable DNA polymerase AmpliTaq-FS (Perkin-Elmer Inc.) in a total volume of 20 μL. Both reactions are begun using typical hot-start conditions. The reactions are performed according to the following thermal cycling program: denaturing at 90° C. for 30 s, annealing at 60° C. for 10 s, extension at 65° C. for 10 s, for a total of 35 cycles. Upon completion, the sequencing reactions are purified by capturing the extended biotinylated products on streptavidin-coated magnetic beads. The beads are washed to remove unextended primer and then the mass label released by treatment of the bead-bound product with a mild reducing agent to cleave the disulfide bound and release the mass label into solution. A 1 μL portion of the supernatant is removed and analyzed by MALDI-TOF mass spectrometry (positive ions, 2.5-dihydroxy benzoic acid matrix). The resulting mass spectra for the Primer E matched template and for the Primer A matched template are shown in FIG. 20A and FIG. 20B, respectively. When Primer E is perfectly matched to the template, the predominant mass label signal seen in the mass spectrum is that from Primer E. Likewise, when Primer a is perfectly matched to the template in the reaction, the predominant mass label signal seen in the mass spectrum is from Primer A. This example demonstrates the potential unity of using a mixture of degenerate, uniquely mass-labeled primers to determine a variable sequence that is adjacent to a fixed sequence.

Example 9

Single-Strand Selective Chemical Release of Mass Label

A chemically-cleavable oligonucleotide probe (SEQ ID NO: 31) containing a bridging 5'-S—P phosphodiester linkage in the backbone is synthesized by standard solid phase synthesis techniques incorporating a modified phosphoramidite reagent at the site of cleavage as described in PCT Patent Application WO 96/37630. The sequence of the 25-mer probe is 5'-CCTGGCAAACTCAACTAGGC(sT)GTCC-3' (SEQ ID NO: 31), where sT indicates the cleavage site. A complementary 35-mer oligonucleotide with the sequence 5'-GATCCGGACAGCCTAGTTGAGTTTGC-CAGGTAAGA-3' (SEQ ID NO: 32), is likewise synthesized.

The probe and complement are hybridized together to form a duplex DNA in 1M triethylammonium acetate buffer by heating a mixture of 10 pmol each at 95° C. for 3 min followed by a 10 min incubation at 70° C. and a subsequent 50° C. 10 min incubation. The mixture is allowed to come to room temperature and $AgNO_3$ is added to a final concentration of 0.14 mM. The silver promoted cleavage reaction is allowed to proceed for 60 min at room temperature (20° C.) after which the reaction is quenched by the addition of excess dithiothreitol. After evaporation of the sample, 3-HPA MALDI matrix solution is added to redissolve the DNA. The solution is spotted onto the mass spectrometer sample plate and analyzed. The resulting mass spectrum and a mass spectrum of a no-complement control cleavage are shown in FIG. 21A and FIG. 21B, respectively. The spectrum of the control reaction shows that under the conditions used, the single-stranded oligonucleotide goes to about 90% complete cleavage, while the spectrum of the double-stranded form shows that under identical conditions not more than about 5% cleavage occurs. This derrionstrates the potential use a chemical cleavage reagent to diminiscrate between hybridized and unhybridized probes for release of mass label.

Example 10

Release of Mass Label by Exonuclease III Digestion of DNA Probe Hybridized to an RNA Transcript A pair of PCR primers for the ribosomal protein L7 gene is synthesized by standard phosphoramidite chemistry. The forward primer contained at the 5'-end and extension which is the promoter region of T7 RNA polymerase. The sequence of the forward primer is 5'-TAATACGACTCACTATAGG- GAGACTGCTGAGGATTGTA-GAGC-3' (SEQ ID NO: 33) and the sequence for the reverse primer is 5'-TCCAACAG-TATAGATCTCATG-3' (SEQ ID NO: 34). A pair of probes is also synthesized, each containing unique mass labels. The probes are designed such that each hybridizes to a different strand of the PCR product while only one of them hybridizes to a strand of transcribed RNA. The peptide mass label used for the upper-strand probe had the sequence CGYGP-KKKRKVGG (SEQ ID NO: 35), and for the lower-strand (RNA-specific) probe the peptide was CKNLNKD-KQVYRATHRB (SEQ ID NO: 36). The synthesis of the mass-labeled probes is described in Example 1E.

A reverse transcription reaction was performed on 10 μg of total RNA isolated from a stable cancer cell line to generate first strand cDNA. The reaction was performed in a total volume of 20 and contained 0.5 μg of oligo dTO primer and 25 units of AMV reverse transcriptase. A PCR reaction was performed on 1 μL of the first strand cDNA using 10 pmol each of the T7-forward and reverse primers and 1 unit of Taq DNA polymerase in a 20 μL reaction.

A two microliter aliquot of the RT-PCR product is then used for a 20 microliter transcription reaction which contains 100 units of T7 RNA polymerase, 20 units of RNAsin inhibitor and 1 mM concentration of each rNTP. The transcription reaction is allowed to proceed at 37° C. for 2 h. One microliter of the transcription reaction product is then probed using 5 pmol each of the two strand specific probes above. As a control, one microliter of the RT-PCR product is used instead of the transcription reaction product. The probes and targets are hybridized in 1× exonuclease III buffer by heating the mixture to 95° C. for 3 min, then incubating at 65° C. for 1 min then cooling to 37° C. Exonuclease III is then added to the mixture and the digestion is allowed to proceed at 37° C. for 1 h. A 1 μL portion of the supernatant was removed and analyzed by MALDI-TOF mass spectrometry (positive ions, 2.5-dihydroxy benzoic acid matrix). The resulting mass spectra of the digested RNA transcription product and control are shown in FIG. 22A and FIG. 22B, respectively. Only the RNA-strand specific probe mass label signal is seen in the transcription reaction sample while both probe mass label signals are seen when the RT-PCR product is probed. The fact that only the RNA-strand specific probe produces a signal in the mass spectrum when RNA transcript is present, together with the fact that signals from both probes should be seen if the signal were resulting only from residual RT-PCR product, shows that the enzyme exonuclease III can be used to specifically digest a probe hybridized to an RNA transcript to release a mass label.

Example 11

Matrix Selectivity for Peptide Mass Label or DNA

A 2 pmol portion of each of the mass-labeled primers Primer a and Primer C is treated with a mild reducing agent to cleave the molecule at the disulfide bond to yield separate peptide and DNA fragments. For each primer, a 1 microliter portion is spotted onto the mass spectrometer sample plate with the matrix 2,5-dihydroxybenzoic acid, and a second 1 microliter portion is spotted with the matrix 3-HPA. The mass spectrum for Primer C obtained with 2.5-dihydroxybenzoic acid is shown in FIG. 23A and shows a strong peptide signal with only very weak, poorly resolved signal at the expected mass of the DNA fragment. In contrast, the mass spectrum obtained with 3-HPA (FIG. 23B) shows a strong, sharp signal for the DNA fragment and a weaker signal for the peptide fragment. The corresponding spectra obtained for primer A are shown in FIG. 23C (2,5-DHB) and FIG. 23D (3-HPA).

These results demonstrate that it is possible to selectively detect a released mass-labeled section of a probe in the presence of the much larger portion of the probe not carrying a mass label.

Example 12

Detection of a Specific Biomolecule (T) in a Restriction Enzyme-Linked Immunoadsorbent Assay As an example of the detection of a target biomolecule via release of mass labels, a model system based on ELISA technology was designed. This assay incorporates a DNA restriction enzyme for the digestion of a mass-labeled substrate that is ultimately detected by mass spectrometry. This example describes a antibody-sandwich ELISA to detect soluble antigens. ELISA are described in Ausubel et al., (1997), incorporated herein by reference. Synthesis of the probe (mass label bound to double-strand oligonucleotide containing an EcoRI restriction site) is described in Example 1. Double-stranded probe is prepared by hybridization of complementary oligonucleotides. Standard solutions of antigen T are prepared for calibration of the assay (1-1000 ng/mL, depending on the linear range of the assay). Specific capture antibodies (Anti-T) and a target recognition molecule crosslinked to the restriction enzyme EcoRI (Anti T-EcoRI) are also prepared (0.1 units of EcoRI per ng of specific antibody; 10 units per mL.).

Procedure

1. Coat wells of microwell dishes (Immulon or equivalent) with the capture antibody (10 ug/mL) which then is bound overnight according to the manufacturer's instructions. Block the residual binding capacity of the plate with blocking buffer (a buffered solution of 0.05% Tween 20 and 0.25% bovine serum albumin) by filling wells with the solution and incubating 30 min at room temperature. Rinse plates with water three times and remove residual water.

2. Bind solutions of known and unknown amounts of antigen T (in blocking buffer) to the wells, 50 μL/well and incubate at least 2 h. Wash plate three times with water, then treat with blocking buffer for 10 min. Rinse again with water three times.

3. Add 50 μL of anti T-EcoRI (containing 0.5 unit of EcoRI activity) to each well and incubate 2 h at room temperature. Wash plate 3 times using 1× ExoRI buffer containing 0.25% BSA.

4. For each 96-well dish, mix
   140 μL Double-strand probe (10 pmol of mass-labeled oligonucleotide, 7 μM stock)
   100 μL EcoRI buffer (10×)
   760 μL H$_2$O 5. Add 10 μL of the above mix to each well; incubate at 37° C. for the appropriate time to obtain a linear response with concentration of T (up to 1 h). Heat inactivate enzyme at 65° C. for 20 min then cool to 4° C. Spot 1 μl of the mixture with DHB, wash dried spots 2× with 2 μL of H$_2$O, and analyze for the released mass label.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Agrawal (ed.), *Protocols for oligonucleotides and Analogs.* Methods in Molecular Biology, Vol. 20, Humana Press, Totowa, N.J., 1993.
Allcock et al., *Contemporary Polymer Chemistry*, Prentice-Hall, Inc., Englewood Cliffs, N.J., 1981.
Arlinghaus et al., *Anal. Chem.,* 69:1510-1517 1999.
Atherton and Shepard, *SOLID PHASE PEPTIDE SYNTHESIS*, IRL, Oxford, 1989.
Ausubel et al., *CURRENT PROTOCOLS IN MOLECULAR BIOLOGY*, John Wiley & Sons, New York, 1997.
Barlos et al., *Tetrahedron Lett.,* 30:3943-3946, 1989.
Bruce et al., *Rapid communications in Mass Spectrometry,* 9:644-650, 1995.
Brummel et al., *Science,* 264:399-402, 1994.
Brummel et al., *Anal. Chem.,* 68:237-242, 1996.
Bueht et al., *Arch. Mal. Prof. Med. Tray.,* 35:395-402, 1974.
Burbaum et al., *Proc. Natl. Acad. Sci. USA.,* 92:6027-6031, 1995.
Copley and Boot, *Biotechniques,* 13:888-892, 1992.
Dale et al., *Proc. Natl. Acad. Sci. USA.,* 70:2238-2242, 1973.
Europeah Patent Application 320,308
European Patent Application 329-822
Freier et al., *J. Med. Chem.,* 38:344-352, 1995.
Freifelder, *Physical Biochemistry applications to Biochemistry and Molecular Biology,* 2nd ed. Wm. Freeman and Co., New York, N.Y., 1982.
Holland et al., *Proc. Natl. Acad. Sci. USA.,* 88:7276-7280, 1991.
Holmes et al., *Biopolymers (Peptide Science),* 37:199-211, 1995.
Ikano and Kambara, *Anal. Biochem.,* 228:101-108, 1995.
Innis et al., *PCR Protocols*, Academic Press, Inc., San Diego, Calif., 1990.
Jensen et al., *Nucleic Acids Research,* 24:3866-3872, 1996.
Kwoh et al., *Proc. Natl. Acad. Sci. USA.,* 86:1173, 1989.
Langer et al., *Proc. Natl. Acad. Sci. USA.,* 78:6633-6637, 1981.
Lee et al., *Nucleic Acids Research,* 21:3761-3766, 1993.
Martin et al., *J. Med. Chem.,* 38:1431-1436, 1995.
Ohlmeyer et al., *Proc. Natl. Acad. Sci. USA.,* 90:10922-10926, 1993.
PCT Patent Application PCT/US87/00880.
PCT Patent Application WO 88/10315.
PCT Patent Application WO 96/37630.
Pei et al., *Science,* 253:1408-1411, 1991.
Sambrook et al., *MOLECULAR CLONING: A LABORATORY MANUAL*, 2d Ed., Cold Spring Harbor Laboratory Press, Cold Spring Harbor, N.Y., 1989.
Saenger, *PRINCIPLES OF NUCLEIC ACID STRUCTURE*, Springer-Verlag, NY, 1983.
Schena et al., *Science,* 270:467-470, 1995.
Senft, J., *Chrom.,* 337:126-130, 1985.
Sproat et al., *Nucleic acids Research,* 15:6181-6196, 1987.
U.S. Pat. No. 4,629,689.
U.S. Pat. No. 4,650,750.
U.S. Pat. No. 4,683,195.
U.S. Pat. No. 4,683,202.
U.S. Pat. No. 4,709,016.
U.S. Pat. No. 4,800,159.
U.S. Pat. No. 4,883,750.
U.S. Pat. No. 5,174,962.
U.S. Pat. No. 5,360,819.
U.S. Pat. No. 5,516,931.
Walker et al., *Proc. Natl. Acad. Sci. USA.,* 89:392-396, 1992.
Wang et al., *Chromatography A,* 721:289-296, 1996.

What is claimed is:

1. A method for multiplexing the detection of a target molecule comprising:
   (a) obtaining a plurality of probes, each comprising a reactive group, a release group and a mass label comprising a biopolymer;
   (b) contacting the target molecule with the plurality of probes to produce probe:target molecule complexes, wherein the target molecule is attached to the reactive group of the probe;
   (c) releasing the mass labels from the probe:target molecule complexes to produce released mass labels; and
   (d) determining the mass of the released mass labels by mass spectrometry, wherein
   each reactive group in a probe:target molecule complex is associated with a unique set of mass labels.

2. The method of claim 1, wherein a plurality of target molecules is contacted with the plurality of probes.

3. The method of claim 1, wherein the set of mass labels are attached to the same probe.

4. The method of claim 1, wherein the set of mass labels are attached to different probes.

5. The method of claim 1, wherein the target molecule is immobilized onto a solid support.

6. The method of claim 4, wherein a plurality of target molecules are immobilized onto the solid support at spaced locations.

7. The method of claim 1, wherein the target molecule is selected from the group consisting essentially of a polynucleotide, an antigen, a ligand, a polypeptide, a carbohydrate, and a lipid.

8. The method of claim 7, wherein the target molecule comprises a polynucleotide.

9. The method of claim 7, wherein the target molecule comprises a polypeptide.

10. The method of claim 1, wherein the reactive group comprises a biomolecule capable of specific molecular recognition.

11. The method of claim 10, wherein the reactive group comprises a polypeptide.

12. The method of claim 11, wherein the polypeptide is selected from the group consisting essentially of an antibody, an enzyme, a receptor, a regulatory protein, a nucleic-acid binding protein, a hormone, or a protein product of a display methods.

13. The method of claim 12, wherein the polypeptide comprises an antibody.

14. The method of claim 12, wherein the polypeptide comprises a product of a phage display method or a bacterial display method.

15. The method of claim 10, wherein the reactive group comprises a polynucleotide or an oligonucleotide.

16. The method of claim 1, wherein the unique set of mass labels comprises a mass label that indicates the presence of a specified component within the reactive group.

17. The method of claim 16, wherein the mass label indicates the presence of the specified component at a specified location within the reactive group.

18. The method of claim 17, wherein a reactive group comprising n specified components is associated with a unique set of mass labels having n members.

19. The method of claim 18, wherein n is from 1 to 1000.

20. The method of claim 17, wherein a reactive group comprising n specified components is associated with a unique set of mass labels having y members wherein n is less than $y!/[x!(y-x)!]$; and wherein x comprises the number of mass labels used per reactive group.

21. The method of claim 17, wherein the plurality of probes each comprise a known reactive group having a known set of mass labels.

22. The method of claim 21, wherein the plurality of probes are prepared by combinatorial synthesis.

23. The method of claim 17, wherein the plurality of target molecules comprise a known chemical structure.

24. The method of claim 16, wherein the target molecule comprises an expressed gene product.

25. The method of claim 24, wherein the expressed gene product is derived from a cloned mRNA.

26. The method of claim 16, wherein the target molecule comprises a cloned genomic DNA.

27. The method of claim 1, wherein the biopolymer comprises one or more monomer units, wherein each monomer unit is separately and independently selected from the group consisting of an amino acid, a nucleic acid, and a saccharide.

* * * * *

SEQUENCE LISTING

```
<160> NUMBER OF SEQ ID NOS: 36

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: 23
<223> OTHER INFORMATION: n is amino-thymidine

<400> SEQUENCE: 1
tgaggtgcgt gtttgtgcct gtn                                              23

<210> SEQ ID NO 2
<211> LENGTH: 13
<212> TYPE: PRT
<213> ORGANISM: Artificial Sequence
<220> FEATURE:
<223> OTHER INFORMATION: Oligopeptide

<400> SEQUENCE: 2

Cys Gly Tyr Gly Pro Lys Lys Lys Arg Lys Val Gly Gly
1               5                   10
```

<210> SEQ ID NO 3
<211> LENGTH: 42
<212> TYPE: DNA
<213> ORGANISM: Artificial Sequence
<220> FEATURE:
<223> OTHER INFORMATION: Oligonucleotide

<400> SEQUENCE: 3
ctcccaggac aggcacaaac acgcacctca aagctgttcc gt         42

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: 17
<223> OTHER INFORMATION: n is amino-thymidine

<400> SEQUENCE: 4
atctgaagtc agtaaangaa c         21

<210> SEQ ID NO 5
<211> LENGTH: 17
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: 13
<223> OTHER INFORMATION: n is amino-thymidine

<400> SEQUENCE: 5
atttaccaga gancgag         17

<210> SEQ ID NO 6
<211> LENGTH: 16
<212> TYPE: PRT
<213> ORGANISM: Artificial Sequence
<220> FEATURE:
<223> OTHER INFORMATION: Oligopeptide

<400> SEQUENCE: 6

Cys Lys Asn Leu Asn Lys Asp Lys Gln Val Tyr Arg Ala Thr His Arg
 1               5                  10                  15

<210> SEQ ID NO 7
<211> LENGTH: 12
<212> TYPE: PRT
<213> ORGANISM: Artificial Sequence
<220> FEATURE:
<223> OTHER INFORMATION: Oligopeptide

<400> SEQUENCE: 7

Thr Cys Val Glu Trp Leu Arg Arg Tyr Leu Lys Asn
 1               5                  10

<210> SEQ ID NO 8
<211> LENGTH: 16
<212> TYPE: PRT
<213> ORGANISM: Artificial Sequence
<220> FEATURE:
<223> OTHER INFORMATION: Oligopeptide -continued

```
<400> SEQUENCE: 8

Cys Ser Arg Ala Arg Lys Gln Ala Ala Ser Ile Lys Val Ser Ala Asp
1               5                   10                  15

<210> SEQ ID NO 9
<211> LENGTH: 15
<212> TYPE: DNA
<213> ORGANISM: Artificial Sequence
<220> FEATURE:
<223> OTHER INFORMATION: Oligonucleotide

<400> SEQUENCE: 9
tttttttttt ttttt                                                    15

<210> SEQ ID NO 10
<211> LENGTH: 22
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: 17
<223> OTHER INFORMATION: n is amino-thymidine

<400> SEQUENCE: 10
ggtttacatg ttccaanatg at                                            22

<210> SEQ ID NO 11
<211> LENGTH: 11
<212> TYPE: PRT
<213> ORGANISM: Artificial Sequence
<220> FEATURE:
<223> OTHER INFORMATION: Oligopeptide

<400> SEQUENCE: 11

Cys Gly Thr Arg Gly Ser Gly Lys Gly Thr Gly
1               5                   10

<210> SEQ ID NO 12
<211> LENGTH: 30
<212> TYPE: PRT
<213> ORGANISM: Artificial Sequence
<220> FEATURE:
<223> OTHER INFORMATION: Oligopeptide
<220> FEATURE:
<221> NAME/KEY: MOD_RES
<222> LOCATION: 7, 19
<223> OTHER INFORMATION: Sulfonated Cysteine

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30

<210> SEQ ID NO 13
<211> LENGTH: 13
<212> TYPE: PRT
<213> ORGANISM: Artificial Sequence
<220> FEATURE:
<223> OTHER INFORMATION: Oligopeptide
<220> FEATURE:
<221> NAME/KEY: MOD_RES
<222> LOCATION: 7
<223> OTHER INFORMATION: Sulfonated Cysteine
```

```
<400> SEQUENCE: 13

Phe Val Asn Gln His Leu Cys Gly Ser His Leu Val Glu
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Oligopeptide

<400> SEQUENCE: 14

Arg Gly Phe Phe Tyr Thr Pro Lys Ala
1               5

<210> SEQ ID NO 15
<211> LENGTH: 8
<212> TYPE: PRT
<213> ORGANISM: Artificial Sequence
<220> FEATURE:
<223> OTHER INFORMATION: Oligopeptide
<220> FEATURE:
<221> NAME/KEY: MOD_RES
<222> LOCATION: 6
<223> OTHER INFORMATION: Sulfonated Cysteine

<400> SEQUENCE: 15

Ala Leu Tyr Leu Val Cys Gly Glu
1               5

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: 1
<223> OTHER INFORMATION: n is amino-thymidine with mass label attached;
      chemically cleavable disulfide-containing group
      between n and g

<400> SEQUENCE: 16
ngtgctcaag aactacatgg                                              20

<210> SEQ ID NO 17
<211> LENGTH: 29
<212> TYPE: DNA
<213> ORGANISM: Artificial Sequence
<220> FEATURE:
<223> OTHER INFORMATION: Oligonucleotide

<400> SEQUENCE: 17
tactccagtt ccatgtagtt cttgagcac                                    29

<210> SEQ ID NO 18
<211> LENGTH: 29
<212> TYPE: DNA
<213> ORGANISM: Artificial Sequence
<220> FEATURE:
<223> OTHER INFORMATION: Oligonucleotide

<400> SEQUENCE: 18
tactccagta ccatgtagtt cttgagcac                                    29
```

```
<210> SEQ ID NO 19
<211> LENGTH: 7
<212> TYPE: PRT
<213> ORGANISM: Artificial Sequence
<220> FEATURE:
<223> OTHER INFORMATION: Oligopeptide

<400> SEQUENCE: 19

Cys Gly Arg Gly Ser Gly Lys
 1               5

<210> SEQ ID NO 20
<211> LENGTH: 19
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: 1
<223> OTHER INFORMATION: n is amino-thymidine with mass label attached;
      chemically cleavable disulfide-containing group
      between n and g

<400> SEQUENCE: 20
ntcggagtca acggatttg                                               19

<210> SEQ ID NO 21
<211> LENGTH: 27
<212> TYPE: DNA
<213> ORGANISM: Artificial Sequence
<220> FEATURE:
<223> OTHER INFORMATION: Oligonucleotide

<400> SEQUENCE: 21
tccagttctc aaatccgttg actccga                                      27

<210> SEQ ID NO 22
<211> LENGTH: 23
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: 1
<223> OTHER INFORMATION: n is amino-thymidine with mass label attached;
      chemically cleavable disulfide-containing group
      between n and g

<400> SEQUENCE: 22
ngatgtctgt atatgttgca ctg                                          23

<210> SEQ ID NO 23
<211> LENGTH: 33
<212> TYPE: DNA
<213> ORGANISM: Artificial Sequence
<220> FEATURE:
<223> OTHER INFORMATION: Oligonucleotide

<400> SEQUENCE: 23
aagttgactc tcagtgcaac atatacagac atc                               33

<210> SEQ ID NO 24
<211> LENGTH: 12
<212> TYPE: PRT
<213> ORGANISM: Artificial Sequence
<220> FEATURE:
<223> OTHER INFORMATION: Oligopeptide
```

```
<400> SEQUENCE: 24

Cys Ala Gly Gly Arg Gly Gly Gly Lys Gly Gly Ala
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Oligopeptide

<400> SEQUENCE: 25

Cys Ala Ser Gly Arg Gly Ser Gly Lys Gly Ser Ala
1               5                   10

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: 1
<223> OTHER INFORMATION: n is amino-thymidine with mass label attached;
      chemically cleavable disulfide-containing group
      between n and g

<400> SEQUENCE: 26
ngtgctcaag aactacatga                                               20

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: 1
<223> OTHER INFORMATION: n is amino-thymidine with mass label attached;
      chemically cleavable disulfide-containing group
      between n and g

<400> SEQUENCE: 27
ngtgctcaag aactacatgt                                               20

<210> SEQ ID NO 28
<211> LENGTH: 29
<212> TYPE: DNA
<213> ORGANISM: Artificial Sequence
<220> FEATURE:
<223> OTHER INFORMATION: Oligonucleotide

<400> SEQUENCE: 28
tactccagtt acatgtagtt cttgagcac                                     29

<210> SEQ ID NO 29
<211> LENGTH: 12
<212> TYPE: PRT
<213> ORGANISM: Artificial Sequence
<220> FEATURE:
<223> OTHER INFORMATION: Oligopeptide

<400> SEQUENCE: 29

Cys Ala Gly Gly Arg Gly Gly Gly Lys Gly Gly Ala
1               5                   10
```

```
<210> SEQ ID NO 30
<211> LENGTH: 12
<212> TYPE: PRT
<213> ORGANISM: Artificial Sequence
<220> FEATURE:
<223> OTHER INFORMATION: Oligopeptide

<400> SEQUENCE: 30

Cys Ala Ser Gly Arg Gly Ser Gly Lys Gly Ser Ala
1               5                   10

<210> SEQ ID NO 31
<211> LENGTH: 25
<212> TYPE: DNA
<213> ORGANISM: Artificial Sequence
<220> FEATURE:
<223> OTHER INFORMATION: Oligonulceotide
<220> FEATURE:
<221> NAME/KEY: modified_base
<222> LOCATION: 21
<223> OTHER INFORMATION: n is a thymidine modified to contain a cleavage
      site

<400> SEQUENCE: 31
cctggcaaac tcaactaggc ngtcc                                              25

<210> SEQ ID NO 32
<211> LENGTH: 35
<212> TYPE: DNA
<213> ORGANISM: Artificial Sequence
<220> FEATURE:
<223> OTHER INFORMATION: Oligonulceotide

<400> SEQUENCE: 32
gatccggaca gcctagttga gtttgccagg taaga                                   35

<210> SEQ ID NO 33
<211> LENGTH: 42
<212> TYPE: DNA
<213> ORGANISM: Artificial Sequence
<220> FEATURE:
<223> OTHER INFORMATION: Oligonulceotide

<400> SEQUENCE: 33
taatacgact cactataggg agactgctga ggattgtaga gc                           42

<210> SEQ ID NO 34
<211> LENGTH: 21
<212> TYPE: DNA
<213> ORGANISM: Artificial Sequence
<220> FEATURE:
<223> OTHER INFORMATION: Oligonulceotide

<400> SEQUENCE: 34
tccaacagta tagatctcat g                                                  21

<210> SEQ ID NO 35
<211> LENGTH: 13
<212> TYPE: PRT
<213> ORGANISM: Artificial Sequence
<220> FEATURE:
<223> OTHER INFORMATION: Oligopeptide

<400> SEQUENCE: 35

Cys Gly Tyr Gly Pro Lys Lys Arg Lys Val Gly Gly
1               5                   10
```

```
<210> SEQ ID NO 36
<211> LENGTH: 16
<212> TYPE: PRT
<213> ORGANISM: Artificial Sequence
<220> FEATURE:
<223> OTHER INFORMATION: Oligopeptide

<400> SEQUENCE: 36

Cys Lys Asn Leu Asn Lys Asp Lys Gln Val Tyr Arg Ala Thr His Arg
 1               5                  10                  15
```